(12) United States Patent
Ferrari et al.

(10) Patent No.: US 8,685,755 B2
(45) Date of Patent: Apr. 1, 2014

(54) COMBINATORIAL MULTIDOMAIN MESOPOROUS CHIPS AND A METHOD FOR FRACTIONATION, STABILIZATION, AND STORAGE OF BIOMOLECULES

(75) Inventors: Mauro Ferrari, Houston, TX (US); Xuewu Liu, Sugar Land, TX (US); Ennio Tasciotti, Houston, TX (US); Ali Bouamrani, Grenoble (FR); Ye Hu, Austin, TX (US)

(73) Assignee: The Board of Regents of The University of Texas System, Austin, TX (US)

( * ) Notice: Subject to any disclaimer, the term of this patent is extended or adjusted under 35 U.S.C. 154(b) by 478 days.

(21) Appl. No.: 12/839,606

(22) Filed: Jul. 20, 2010

(65) Prior Publication Data

US 2011/0065207 A1 Mar. 17, 2011

Related U.S. Application Data

(60) Provisional application No. 61/227,016, filed on Jul. 20, 2009.

(51) Int. Cl.
 *G01N 33/552* (2006.01)
 *B32B 5/16* (2006.01)
 *B23H 3/00* (2006.01)
 *C03C 15/00* (2006.01)

(52) U.S. Cl.
 USPC ............. 436/527; 428/402; 205/640; 216/95

(58) Field of Classification Search
 None
 See application file for complete search history.

(56) References Cited

U.S. PATENT DOCUMENTS

| | | | | |
|---|---|---|---|---|
| 4,168,146 A * | 9/1979 | Grubb et al. | ............... | 435/7.92 |
| 5,470,532 A * | 11/1995 | Hagen et al. | ............... | 422/429 |
| 5,693,785 A * | 12/1997 | Woodard et al. | ............ | 536/25.4 |
| 6,536,604 B1 * | 3/2003 | Brinker et al. | ............... | 210/490 |
| 6,630,358 B1 * | 10/2003 | Wagner et al. | .................. | 506/9 |
| 7,270,850 B2 * | 9/2007 | Krotz et al. | ............. | 427/255.28 |
| 8,071,132 B2 * | 12/2011 | Adair et al. | ................. | 424/489 |
| 2003/0127393 A1 | 7/2003 | Tepper et al. | | |
| 2003/0232340 A1 | 12/2003 | Anderson | | |
| 2005/0227239 A1 | 10/2005 | Joyce | | |
| 2006/0159916 A1 * | 7/2006 | Dubrow et al. | ................ | 428/357 |
| 2008/0102030 A1 * | 5/2008 | Decuzzi et al. | ................ | 424/9.1 |
| 2008/0277578 A1 * | 11/2008 | Ferrari et al. | ................. | 250/288 |
| 2008/0280140 A1 * | 11/2008 | Ferrari et al. | ................. | 428/402 |

FOREIGN PATENT DOCUMENTS

WO WO 2005-045392 5/2005

OTHER PUBLICATIONS

Terracciano et al., "Selective binding and enrichment for low-molecular weight biomakrer molecules in human plasma after exposure to nanoporous silica particles", Proteomics (2006) 6:3243-3250.*
Geho et al., "Fractionation of serum components using nanoporous substrates", Bioconjugate Chemistry (2006) 17:654-661.*
Terracciano et al., "Derivatized mesoporous silica beads for MALDI-TOF MS profiling of human plasma and urine", Bioconjugate Chemistry (2009) 20:913-923.*
Hu et al., "Tailoring of the nanotexture of mesoporous silica films and their functionalized derivatives for selectively harvesting low molecular weight protein", ACS Nano (2010) 4(1):439-451.*
Gasparl et al., "Nanoporous surfaces as harvesting agents for mass spectrometric analysis of peptides in human plasma", J. Proteome Research (2006) 5:1261-1266.*
Bouamrani et al., "Mesoporous silica chips for selective enrichment and stabilization of low molecular weight proteome," *Proteomics*, 10(3):496-505, 2010.
Ferrari, "Cancer nanotechnology: opportunities and challenges," *Nature Reviews, Cancer*, 5:161-171, 2005.
Jungbauer et al., "Performance and characterization of a nanophased porous hydroxyapatite for protein chromatography," *Biotechnology and Bioengineering*, 87(3):364-375, 2004.

* cited by examiner

*Primary Examiner* — Shafiqul Haq
*Assistant Examiner* — Gary E Hollinden
(74) *Attorney, Agent, or Firm* — Parker Highlander PLLC

(57) ABSTRACT

A new fractionation device shows desirable features for exploratory screening and biomarker discovery. The constituent MSCs may be tailored for desired pore sizes and surface properties and for the sequestration and enrichment of extremely low abundant protein and peptides in desired ranges of the mass/charge spectrum. The MSCs are effective in yielding reproducible extracts from complex biological samples as small as 10 μl in a time as short as 30 minutes. They are inexpensive to manufacture, and allow for scaled up production to attain the simultaneous processing of a large number of samples. The MSCs are multiplexed, label-free diagnostic tools with the potential of biological recognition moiety modification for enhanced specificity. The MSCs may store, protect and stabilize biological fluids, enabling the simplified and cost-effective collection and transportation of clinical samples. The MSC-based device may serve as a diagnostic tool to complement histopathology, imaging, and other conventional clinical techniques. The MSCs mediated identification of disease-specific protein signatures may help in the selection of personalized therapeutic combinations, in the real-time assessment of therapeutic efficacy and toxicity, and in the rational modulation of therapy based on the changes in the protein networks associated with the prognosis and the drug resistance of the disease.

6 Claims, 61 Drawing Sheets

| | MASS | IP | CV DAY2 | CV DAY3 | CV DAY5 | CV DAY8 |
|---|---|---|---|---|---|---|
| DES-ARG1-BRADYKININ | 905.05 | 10.18 | 15.76 | 6.55 | 1.55 | 1.97 |
| ANGIOTENSIN II | 1046.54 | 6.74 | 19.22 | 11.65 | 2.73 | 6.56 |
| BRADYKININ | 1060.23 | 12 | 7.83 | 3.22 | 0.51 | 2.29 |
| ANGIOTENSIN I | 1297.51 | 6.92 | 18.69 | 12.48 | 7.29 | 6.31 |
| SUBSTANCE P-AMIDE | 1348.66 | 11 | 3.9 | 0.22 | 0.11 | 2.15 |
| GLU1-FIBRINOPEPTIDE B | 1571.61 | 4 | 2.28 | 5.51 | 7.32 | 0.83 |
| NEUROTENSIN | 1673.96 | 9.7 | 0.05 | 0.07 | 0.11 | 0.09 |
| A-ENDORPHIN | 1746.95 | 6 | 1.14 | 10.39 | 11.32 | 3.75 |
| ACTH(1-17) | 2094.46 | 10.45 | 3.52 | 0.63 | 2.92 | 0.51 |
| ACTH(18-39) | 2466.72 | 4.25 | 4.57 | 2.92 | 0.79 | 4.77 |
| INSULIN OXIDIZED B CHAIN | 3496.96 | 6.9 | 26.36 | 22.03 | 17.54 | 27.2 |
| ACTH(7-38) | 3660.19 | 9.4 | 9.03 | 7.88 | 0.35 | 10.12 |
| INSULIN | 5734.51 | 5.3 | 3.88 | 0.41 | 9.47 | 2.79 |
| EGF | 6217.01 | 4.78 | 4.77 | 5.03 | 10.62 | 2.24 |
| INSULIN-LIKE GF II | 7475.46 | 6.46 | 0.8 | 3.39 | 5.66 | 4.12 |
| UBIQUITIN | 8565 | 6.56 | 13.75 | 3.72 | 0.4 | 5.27 |
| B2-MICROGLOBULIN | 11730 | 5.6 | 2.03 | 1.35 | 0.12 | 2.11 |
| CYTOCHROME C | 12361.96 | 9.59 | 1.49 | 1.13 | 5.99 | 10.04 |
| A-LACTALBUMIN | 14179 | 4.8 | 1.92 | 3.32 | 5.96 | 0.84 |
| APOMYOGLOBIN | 16952.27 | 7.36 | 1.77 | 0.52 | 2.38 | 3.58 |
| B-LACTOGLOBULIN B | 18282.21 | 5.3 | 0.07 | 11.71 | 3.39 | 3.63 |
| RETINOL BINDING | 20575.99 | 5.15 | 2.63 | 5.66 | 3.68 | 3.3 |
| CARBONIC ANHYDRASE 1 | 28739 | 6.4 | 0.39 | 0.44 | 0.03 | 2.21 |
| ALDOLASE | 39212.28 | 8.4 | 0.1 | 1.62 | 2.5 | 1.59 |
| ENOLASE | 46672.00 | 6.17 | 7.63 | 3.98 | 8.55 | 6.78 |
| ALBUMIN | 66431 | 5.6 | 14.12 | 8.12 | 6.42 | 3.16 |
| | | AVERAGE CV | 6.45 | 5.15 | 4.53 | 4.43 |

*FIG. 5*

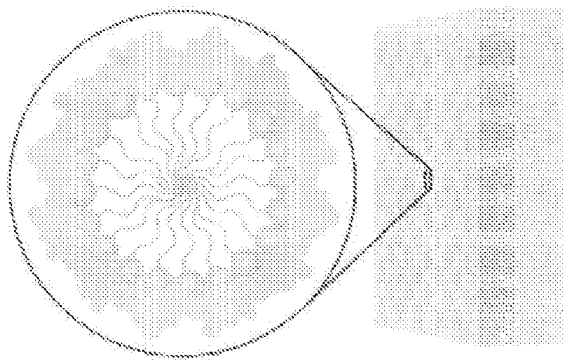
*FIG. 7D*
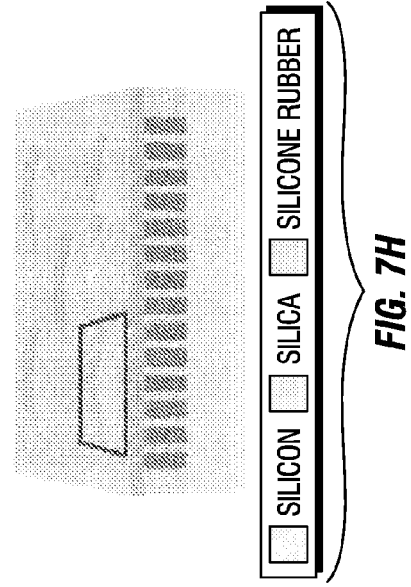
*FIG. 7F*
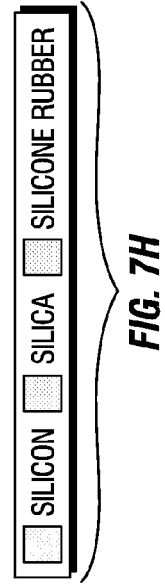
*FIG. 7H*
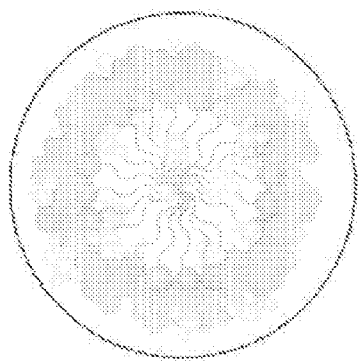
*FIG. 7C*
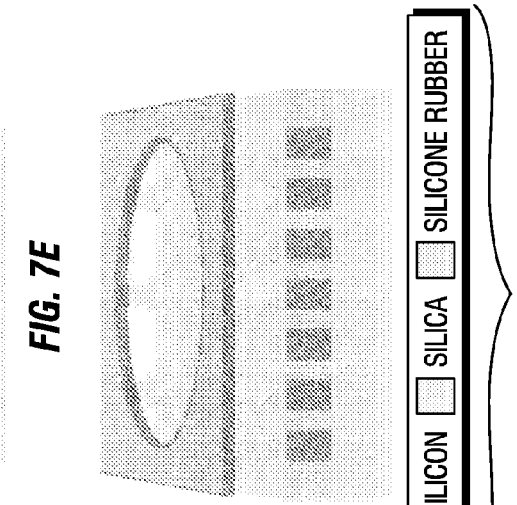
*FIG. 7E*
*FIG. 7G*
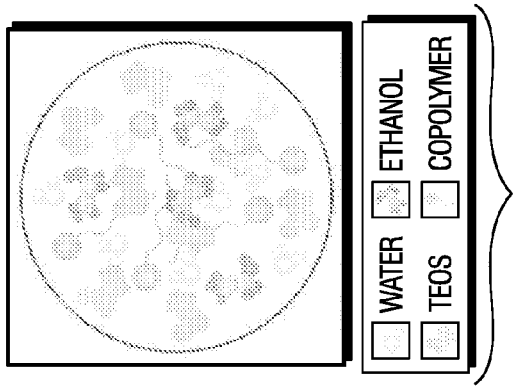
*FIG. 7A*
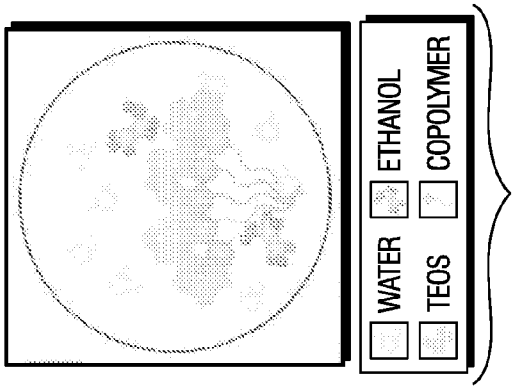
*FIG. 7B*

Pore Sizes

Hydrophobicity

Swelling agent

| SAMPLE LABEL | SURFACTANT | TREATMENT | PORE SIZE (nm) | POROSITY (%) | PORE VOLUME (NL) | SURFACE AREA (MM2) | CONTACT ANGLE |
|---|---|---|---|---|---|---|---|
| LP | L121+PPG | O2 PLASMA | 8.96 | 70.0 | 12.31 | 7834 | 7.02 |
| X11 | L121+PPG | O2 PLASMA | 7.36 | 57.2 | 11 | 10762 | 10.35 |
| GX6 | L121 | O2 PLASMA | 5.17 | 55.0 | 8.14 | 8556 | 3.9 |
| X13 | L121+TMB | | 4.22 | 44.8 | 7.33 | 10315 | 8.5 |
| NX2 | L64 | O2 PLASMA | 2.98 | 53.9 | 10.56 | 14967 | 7.9 |
| GX8 | L35 | O2 PLASMA | 2.72 | 42.0 | 6.05 | 13215 | 5.94 |
| NX3 | F108 | O2 PLASMA | 3.71 | 52.8 | 8.95 | 12778 | 14.3 |
| NX4 | F108 | HMDS | 3.29* | 54.2 | 7.85 | 13846 | 67.1 |

| WAFER | PORE VOLUME NL | POROSITY (%) | THICKNESS (NM) | COPOLYMER | TREATMENT |
|---|---|---|---|---|---|
| X1 | 5.82 | 46 | 393 | F127+30%TMB | |
| X2 | 8.02 | 48.9 | 510 | F127 | |
| X3 | 8.02 | 48.9 | 510 | F127 | |
| X4 | 8.02 | 48.9 | 510 | F127 | |
| X5 | 10.31 | 60 | 534 | L64 | |
| X6 | 9 | 53.1 | 527 | L121+TFTS | |
| X7 | 9.02 | 53.2 | 527 | L121 | $O_2$ PLASMA |
| X8 | 9.89 | 51.5 | 597 | L64+50%PPG | |
| X9 | 12.94 | 60.3 | 667 | L121+50%PPG | $O_2$ PLASMA |
| X10 | 11.86 | 57 | 647 | P123+50%PPG | $O_2$ PLASMA |
| X11 | 11 | 57.2 | 598 | L121+100%PPG | $O_2$ PLASMA |
| X12 | 13.45 | 62.6 | 668 | L121+150%PPG | $O_2$ PLASMA |
| X13 | 7.327 | 44.8 | 508 | L121+50%TMB | |
| X14 | 10.59 | 52.35 | 629 | L121+50%MPTES | |
| X15 | 5.09 | 30.9 | 512 | L121+50%MPTES | |
| NX1 | 9.98 | 53.3 | 582 | L64 | |
| NX2 | 10.56 | 53.9 | 609 | L64 | $O_2$ PLASMA |
| NX5 | 9.98 | 53.3 | 582 | L64 | HMDS |
| NX3 | 8.95 | 52.8 | 527 | F108 | $O_2$ PLASMA |
| NX4 | 7.85 | 54.2 | 450 | F108 | HMDS |
| NT1 | 8.59 | 42.2 | 633 | F127 | |
| NT2 | 12.13 | 48.9 | 771 | F127 | |
| NT3 | 7.19 | 37.4 | 598 | F127 | |
| NT4 | 4.66 | 42.6 | 340 | P123 | |
| NT5 | 15.09 | 62.3 | 753 | L121+50%PPG | |
| NT6 | 13.23 | 62.7 | 656 | L121+100%PPG | |
| NT7 | 7.86 | 60.3 | 405 | L121+150%PPG | |
| NT8 | 8.62 | 57.4 | 467 | L121 | |
| NT9 | 7.84 | 44 | 554 | P123 | APTES |

*FIG. 21*

Substance P 1348.6 Da a-Endorphin 1746.9 Da

ACTH(7-38) 3660.2 Da

Insulin 5734.5 Da

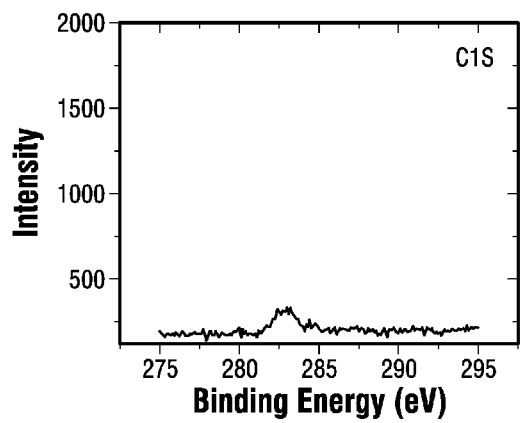
FIG. 29A
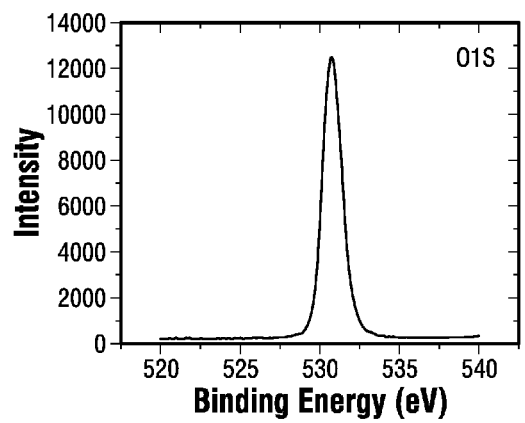
FIG. 29C
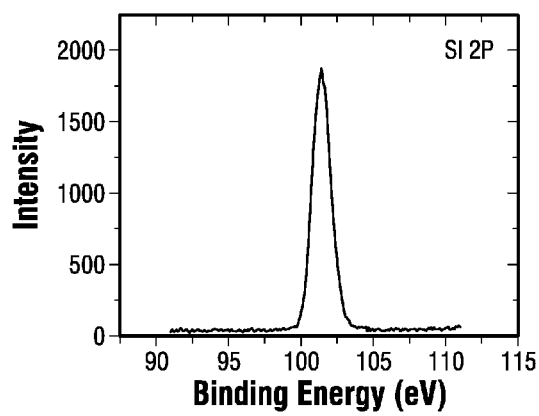
FIG. 29B
| ELEMENT | ATOMIC CONCENTRATION (%) |
|---|---|
| SI 2P | 32.70 |
| O 1S | 65.53 |
| C 1S | 1.71 |
FIG. 29D

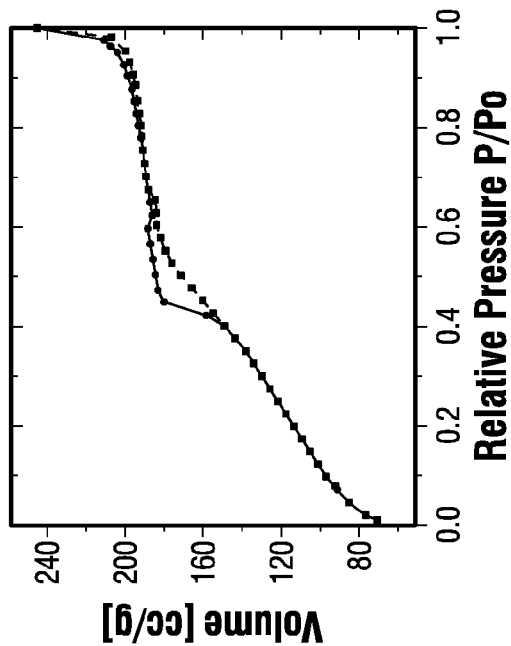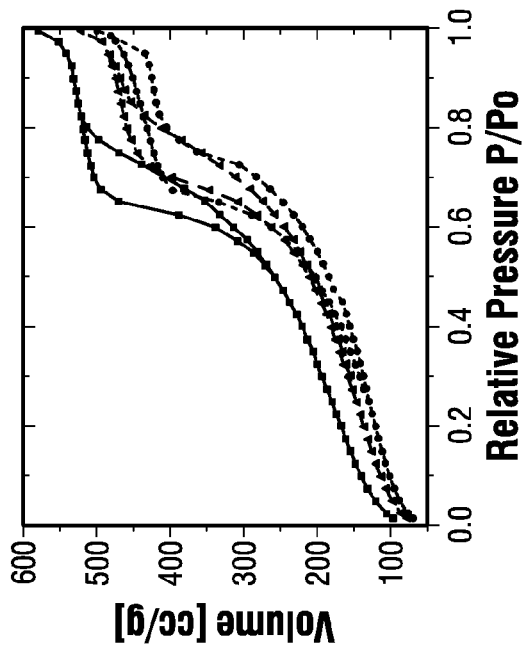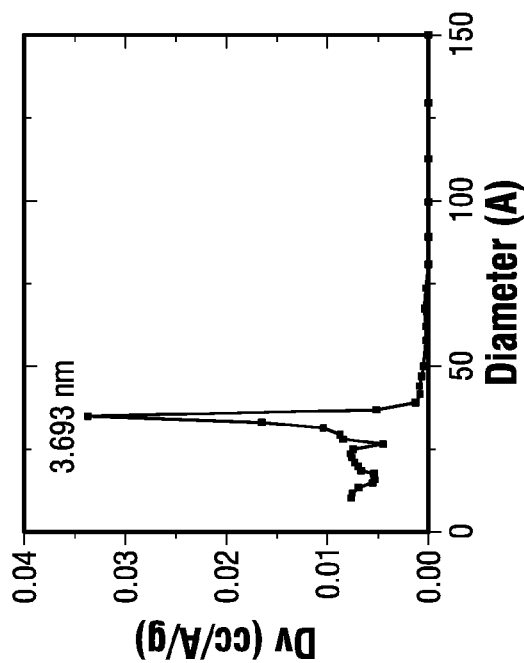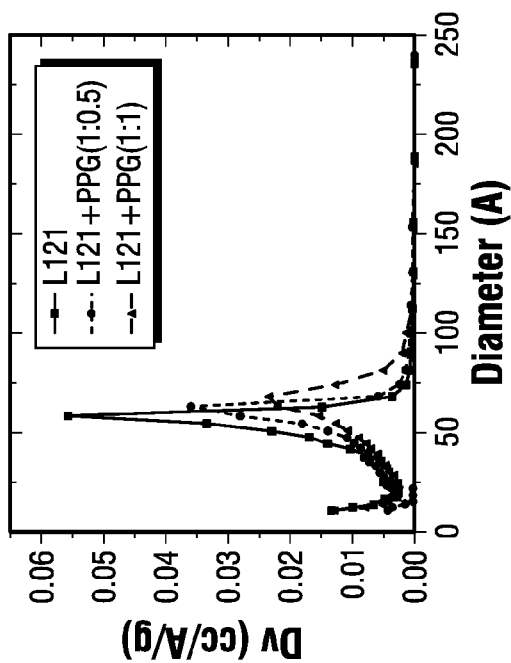
FIG. 36A-1
FIG. 36A-2
FIG. 36B-1
FIG. 36B-2

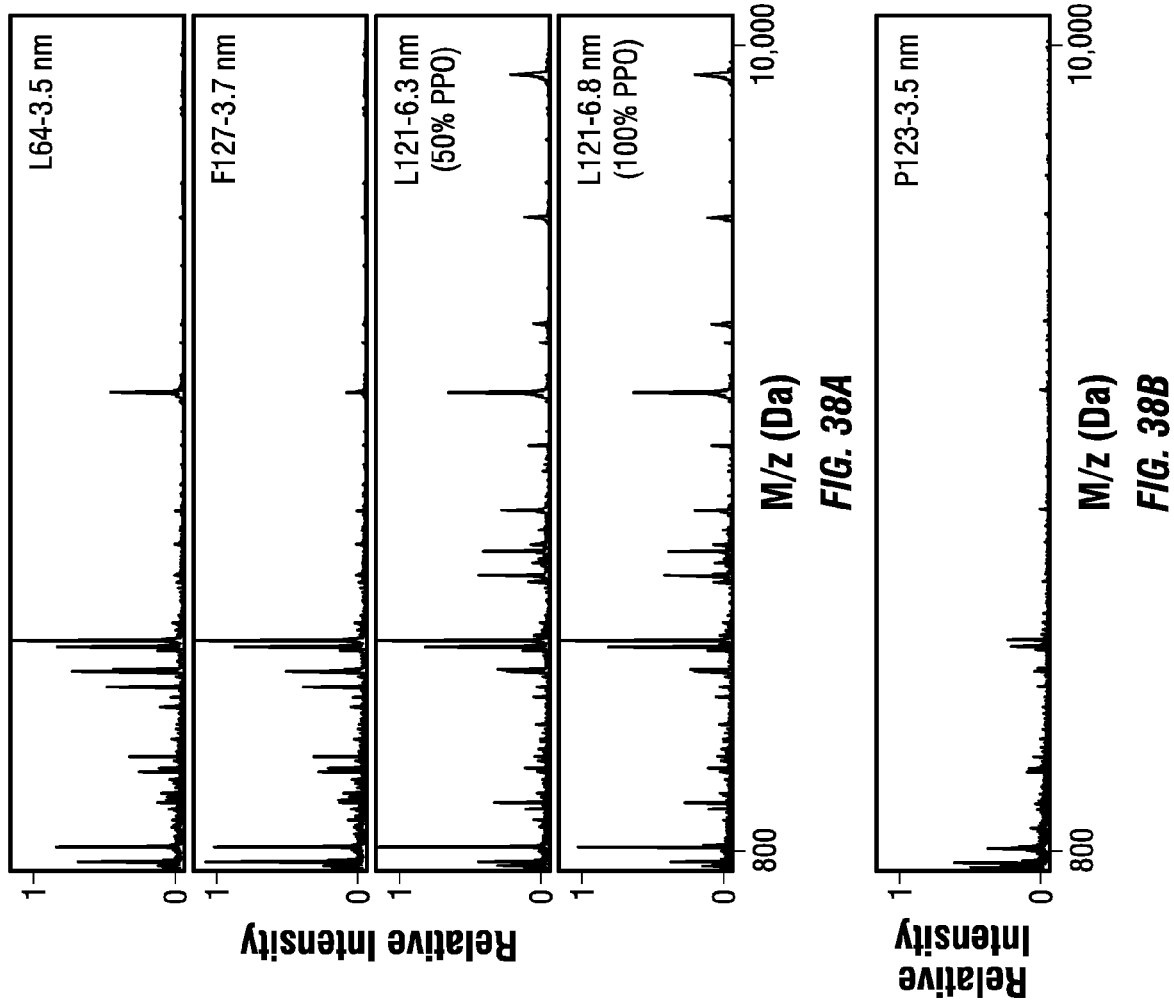

| SURFACTANT POLYMER | MOLAR RATIO OR REACTANTS TEOS: POLYMER: H$_2$O:ETOH:HCl | STRUCTURE | THICKNESS (nm) | REFLECTIVE INDEX | POROSITY (%) | BET SURFACE AREA (m$^2$/g) | PORE VOLUME (cc/g) | AVERAGE PORE SIZE (nm) |
|---|---|---|---|---|---|---|---|---|
| F127 | 1:0.751X10$^{-2}$:11:18.2:0.16 | 3D CUBIC | 820.2 ± 1.3 | 1.220 ± 0.001 | 47.9 ± 0.1 | 191.5 | 0.427 | 3.921 |
| F127 | 1:1.13X10$^{-2}$:11:18.2:0.16 | 3D HONEYCOMB HEXAGONAL | 884.7 ± 0.7 | 1.201 ± 0.002 | 50.3 ± 0.1 | 640.6 | 0.558 | 3.692 |
| F127 | 1:1.51X10$^{-2}$:11:18.2:0.16 | 2D HEXAGONAL | 920.4 ± 1.9 | 1.217 ± 0.003 | 48.5 ± 0.1 | 1131.0 | 0.742 | 3.700 |
| P123 | 1:9.4X10$^{-3}$:6:14.8:0.85 | 2D HEXAGONAL | 905.5 ± 0.2 | 1.235 ± 0.001 | 48.8 ± 0.2 | 483.1 | 0.382 | 3.693 |
| L64 | 1:2.14X10$^{-2}$:6:11.5:0.16 | WORM-LIKE | 890.5 ± 1.6 | 1.189 ± 0.002 | 56.0 ± 0.2 | 562.6 | 0.465 | 3.205 |
| L121 | 1:1.09X10$^{-2}$:6:14.8:0.16 | WORM-LIKE | 857.2 ± 0.8 | 1.193 ± 0.001 | 55.2 ± 0.4 | 587.8 | 0.811 | 5.817 |
| L121+50%PPG | 1:1.09X10$^{-2}$:6:14.8:0.16 | NON-ORDER | 871.5 ± 1.0 | 1.163 ± 0.002 | 60.9 ± 0.0 | 499.3 | 0.817 | 6.266 |
| L121+100%PPG | 1:1.09X10$^{-2}$:6:14.8:0.16 | NON-ORDER | 940.3 ± 3.5 | 1.148 ± 0.003 | 65.5 ± 0.2 | 664.7 | 0.850 | 6.790 |

FIG. 39

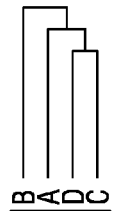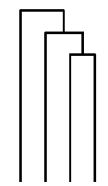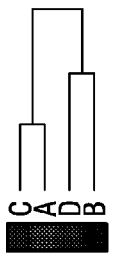
*FIG. 48A*  *FIG. 48B*  *FIG. 48C*  *FIG. 48D*

COMBINATORIAL MULTIDOMAIN MESOPOROUS CHIPS AND A METHOD FOR FRACTIONATION, STABILIZATION, AND STORAGE OF BIOMOLECULES

PRIORITY

This application claims priority to U.S. provisional patent application No. 61/227,016, filed Jul. 20, 2009, which is incorporated herein by reference in its entirety.

STATEMENT FOR FEDERALLY FUNDED RESEARCH

This invention was made with government support under grant no. NNJ06HE06A, awarded by NASA; and grant nos. CA122864 and CA128797, both awarded by the National Institutes of Health. The government has certain rights in the invention.

BACKGROUND OF THE INVENTION

1. Field of the Invention

The subject matter described in this application relates generally to the field of nanotechnology and, in particular, to porous, nanoporous, and mesoporous objects, such as particles, and methods for fractionation, stabilization, and storage of biomolecules.

2. Background of the Invention

A promising strategy of early disease diagnosis is the detection of molecular biomarkers from readily available body fluids, such as blood. Considerable attention has been devoted to the development of proteomic methods for the quantitative and simultaneous detection and identification of molecular biomarkers constituted by multiple proteins and peptides using Mass Spectrometry (MS). Several strategies of sample treatment prior to MS analysis have been developed including conventional 2-dimensional gel electrophoresis, pre-fractionation processes, depletion of most abundant proteins, and beads equalization. In spite of these advances, less effort has been made to overcome the problems of denaturation and degradation of samples during long sample handling procedures, maintenance of protein stability during sample processing, and stabilization of samples during long-term storage. Furthermore, the detection of low abundant markers and low molecular weight (LMW) species remains a critical challenge due to experimental variability, limited reproducibility, long sample handling procedures, protein stability during sample processing, and generation of misleading artifacts as a consequence of unreliable experimental procedures. Macrostructure materials have been used to address some of these issues, and continue to be potentially useful in many applications.

SUMMARY OF THE INVENTION

A first of numerous aspects of the invention is to provide a method of fractionating or separating components in a sample comprising the steps of providing a sample comprising at least a first component and a second component; providing a substrate comprising a mesoporous material having two or more domains, wherein the two or more domains allow for separation of the first and second component; and contacting the mesoporous material with the sample to separate the first component and second component.

It is a further aspect of the invention to provide a method of separating components in a biological sample, the method comprising the steps of providing a biological sample having a first component and a second component; providing a substrate comprising a mesoporous material with a pre-determined pore morphology, wherein said pore morphology permits the separation of the first component from said second component; and contacting the biological sample with said substrate to separate the first component and second component.

It is a further aspect of the invention to provide the method as described above wherein the sample is a biological fluid selected from the group consisting of blood serum, blood plasma, blood, urine, seminal fluid, seminal plasma, pleural fluid, ascites, nipple aspirate, feces, and saliva.

It is a further aspect of the invention to provide the method as described above wherein the first component and the second component comprise peptides, antigens, antibodies, proteins, protein fragments, RNA, or DNA, and a molecular weight of the first component is lower than a molecular weight of the second component.

It is a further aspect of the invention to provide the method as described above further comprising stabilizing the first and second components that have been separated into domains.

It is a further aspect of the invention to provide the method as described above wherein the mesoporous material is a nanoporous silicon, nanoporous oxide material, and/or nanoporous silica.

It is a further aspect of the invention to provide the method as described above wherein the mesoporous material is a molecular cut-off. The molecular cut-off of the substrate of the present invention may range from 700 Da to 50 kDa, optionally from 1 kDa to 25 kDa, optionally from 10 kDa to 15 kDa.

It is a further aspect of the invention to provide the method as described above wherein the two or more domains on the mesoporous material have different modified surfaces, said modified surface differing in terms of molecular cut-off, pore structure, electrical charge, and/or functionalization with organic functional groups or inorganic metal ions, or both. Organic functional groups contemplated by the present invention include, but are not limited to, amino, thiol, carboxy acid, sulfate, phosphate, and epoxy moieties. Inorganic metal ions contemplated by the present invention include, but are not limited to, gallium, titanium, or zirconium.

It is a further aspect of the invention to provide the method as described above wherein said two or more domains are defined on the mesoporous material by photolithography compatible photoresists, molded PDMS films, or silicone rubbers.

It is a further aspect of the invention to provide the method as described above wherein the substrate is selected from the group consisting of a film, a wafer, a particle, and a microchip.

It is a further aspect of the invention to provide the method as described above further comprising extracting the first component from the mesoporous material, washing the mesoporous material subsequent to said contacting the mesoporous material with the sample, and wherein one domain on the mesoporous material adsorbs the first component.

It is a further aspect of the invention to provide the method as described above further comprising analyzing the first component by mass spectrometry, gel electrophoresis, chromatography, bioassay, or a combination thereof, wherein the mass spectrometry is MALDI-TOF mass spectrometry, LC/MS mass spectrometry, ESI-MS mass spectrometry, tandem mass-spectrometry, or SELDI mass spectrometry.

It is a further aspect of the invention to provide a method of analyzing a sample, the method comprising the steps of providing the sample; providing a substrate comprising a mesoporous material comprising two or more domains; exposing the mesoporous material to the sample such that a fraction of the sample is retained by the mesoporous material; and analyzing said fraction of the sample retained by the mesoporous material.

It is a further aspect of the invention to provide a method of detecting a marker of a physiological condition in a sample, the method comprising the steps of providing a sample affected by the physiological condition; providing a substrate comprising a mesoporous material comprising two or more domains; exposing the mesoporous material to the sample; analyzing a fraction of the sample retained by a domain on the mesoporous material; and comparing a result of the analyzing with a result of analyzing a control sample to detect the marker of the physiological condition.

It is a further aspect of the invention to provide a probe comprising a substrate that comprises a mesoporous material comprising two or more domains to separate a first component from a second component into said domains, wherein said probe is configured and arranged to be inserted into a mass spectrometer.

It is a further aspect of the invention to provide the method as described above wherein said pre-determined pore morphology is selected from the group consisting of cubic, hexagonal, honeycomb-like, tubular, circular, oblong, and combinations thereof.

It is a further aspect of the invention to provide the method as described above wherein the mesoporous material has a pore size of 1 nm to 30 nm, optionally 1 nm to 25 nm, optionally 1 nm to 20 nm, optionally 2 nm to 12 nm, or optionally 2 nm to 10 nm.

It is a further aspect of the invention to provide a method of analyzing a sample, the method comprising the steps of providing the sample; providing a substrate comprising a mesoporous material, wherein the pores of said mesoporous material have a pre-determined pore morphology; exposing the mesoporous material to the sample such that a fraction of the sample is retained by the mesoporous material; and analyzing a fraction of the sample retained by the mesoporous material.

It is a further aspect of the invention to provide a method of detecting a marker of a physiological condition in a sample, the method comprising the steps of providing a sample affected by the physiological condition; providing a substrate comprising a mesoporous material, wherein the pores of said mesoporous material are substantially uniform and have a pre-determined pore morphology; exposing the mesoporous material to the sample; analyzing a fraction of the sample retained by the mesoporous material; and comparing a result of the analyzing with a result of analyzing a control sample to detect the marker of the physiological condition.

It is a further aspect of the invention to provide a probe comprising a substrate that comprises a mesoporous material having a pre-determined morphology to separate a first component from a second component, wherein said probe is configured and arranged to be inserted into a mass spectrometer.

It is a further aspect of the invention to provide a mesoporous silica chip comprising multiple pores, and wherein the pores on said chip are of different sizes and physiochemical properties.

It is a further aspect of the invention to provide the chip as described above wherein said physiochemical properties are selected from the group consisting of surface area, pore size, the presence of organic functional groups or inorganic metal ions, and the presence of an electrical charge.

It is a further aspect of the invention to provide the chip as described above, wherein said pores have a shape comprising 2-D or 3-D cubic, 2-D or 3-D hexagonal, honeycomb-like or 3-D wormlike, tubular, circular, oblong, and combinations thereof.

Still other aspects, features, and attendant advantages of the present invention will become apparent to those skilled in the art from a reading of the following detailed description of embodiments constructed in accordance therewith, taken in conjunction with the accompanying figures.

BRIEF DESCRIPTION OF THE DRAWINGS

The invention of the present application will now be described in more detail with reference to exemplary embodiments of the invention, given only by way of example, and with reference to the accompanying drawings, in which:

FIG. 5 is a table showing a summary of the physico-chemical properties of the selected peptide and protein standards and variability of peak intensities for each LMW marker. The standards were combined, dispensed in equal amount, dried by vacuum centrifugation, and stored at −20° C. The stability of the set of standards was investigated by MS, and no degradation was found. The coefficient of variations of the intensities of peaks after 2, 3, 5, and 8 days storage at −20° C. compared to freshly prepared sample were calculated (CV2, CV3, CV5, and CV8 respectively).

FIG. 21 is a table showing a summary of physical properties of all the nanoporous chips manufactured and characterized in this study.

FIG. 27 shows the effects of physico-chemical modifications on the LMW enrichment. Panel a shows the intensity bar graph of specific peptides recovery on 3D-Cubic and 3D-Hexagonal F127 MSC. The different structural modifications present a selective enrichment. Panel b shows the MS profiles of selectively captured peptides on the chemically modified chips. Positively and negatively charged MSC specifically enrich negative and positive peptides respectively.

FIG. 29 shows the purity of MPS thin films. XPS core level spectra was used to analyze the relative amounts of C, Si, and O on the surface of a mesoporous silica thin film prepared from Plutonic L121. The tabulated atomic concentration of each element is shown in the lower right.

FIG. 36 shows pore size distribution of mesoporous silica thin films prepared with different triblock copolymer templates and the corresponding adsorption/desorption isotherm (inset): a. P123; b. L121 and L121 with swelling agent (PPG) at molar ratios of 0.5 and 1.0.

FIG. 37 shows contact angle goniometry for MPS thin films. a. A representative image of contact angle measurements for the mesoporous silica chips prepared using L121; b. A chart of contact angles for all mesoporous silica thin film chips developed.

FIG. 39 shows the molar ratio of starting materials used to fabricate the mesoporous silica thin films and their final physical properties, as characterized by ellipsometry and $N_2$ adsorption/desorption isotherms, for the four different block copolymers, P123, F127, L64, L121 and L121 with two different molar ratio of swelling agent.

FIG. 48 depicts the unsupervised hierarchical clustering analysis for the ability of the MPS chips immobilized with different metal ions for LMW phosphopeptide recovery (Cluster A: $Zr^{4+}$, Cluster B: $Ga^{3+}$, and Cluster C: $Ti^{4+}$). Red indicates peak intensity higher than the median value, green indicates peak intensity lower than the median value, and black represents peak intensity equal to the median values. Each row represents an individual MALDI MS mass peak and each column represents a type of fractionated sample, with unprocessed phosphopeptide sample as a negative control. The samples are divided by (a) Raw α-Casein, (b) Trypsinized α-Casein, (c) Trypsinized α-Casein treated with phosphatase, (d) Raw α-Casein treated with phosphatase.

DETAILED DESCRIPTION OF EXEMPLARY EMBODIMENTS

Figure 1A:
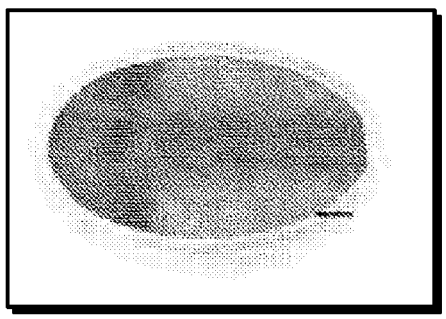
FIG. 1 is a series of photographs of mesoporous silica chips (MSC) patterned either with a 50 µm thick SU-8 hydrophobic photoresist (A, C, D) or with a 500 µm thick molded PDMS film (B, D, F). In C and D note the relative thickness of the different material masks (SU-8 and PDMS, respectively). The top views of different SU-8 and PDMS patterned chips (E and F, respectively) with decreasing fractionation areas show the uniformity of the surfaces employed for the sample fractionation.
Figure 1B:
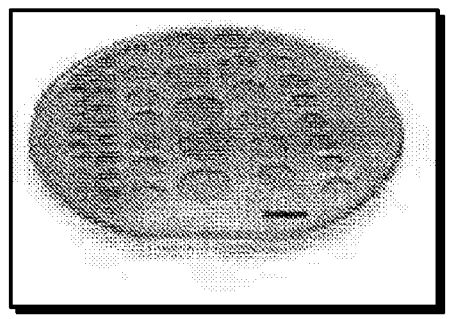
Figure 1C:
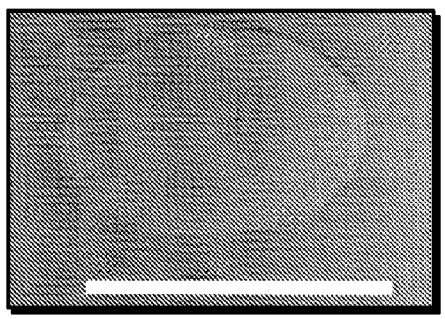
Figure 1D:
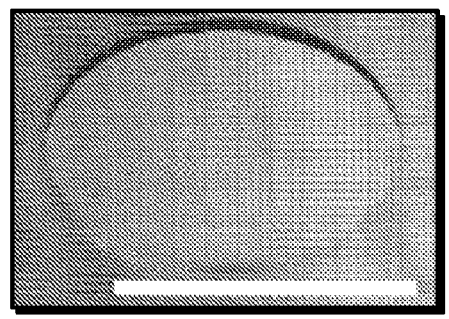
Figure 1E:
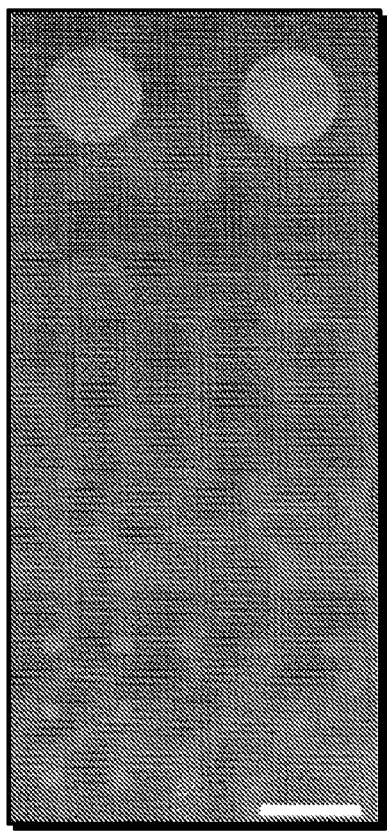
Figure 1F:
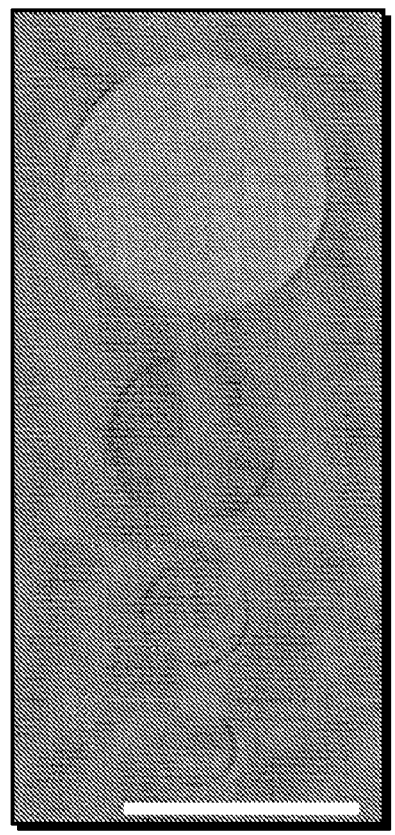
Figure 2A:
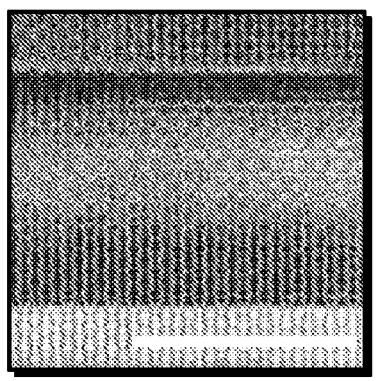
FIG. 2 shows the production and assembly of MSCs for proteomic applications. Panels A and B show cross-sectional views of GX6 chip by SEM and TEM imaging, respectively (scale bar is 500 nm). Panel C shows a 45° view of X1 chip by SEM. Panels D and E show the schematic assembly of silicon rubber mask and MSC. Panels F-H are photographs of MSCs with the silicone rubber mask; the area defined by the mask creates a "well like" structure defined by the thickness of the silicone rubber.
Figure 2B:
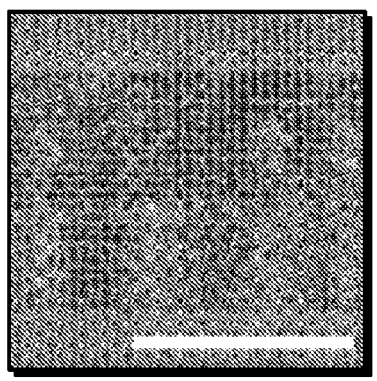
Figure 2C:
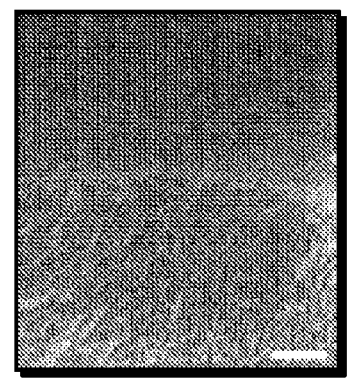
Figure 2D:
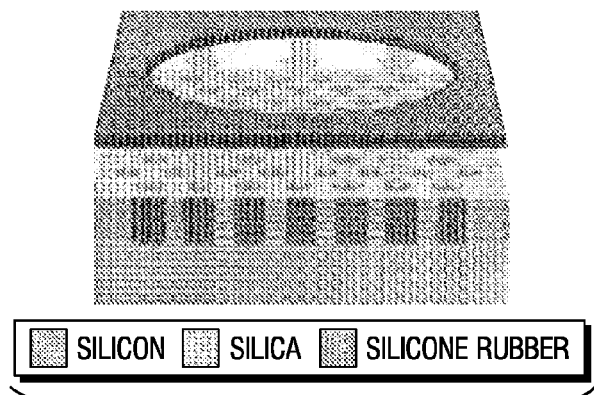
Figure 2F:
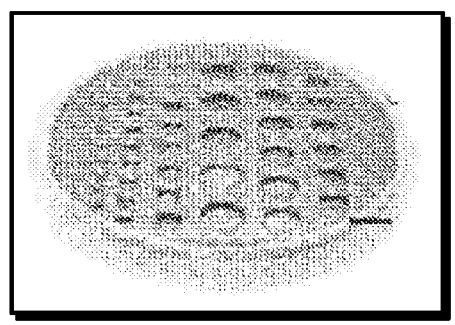
Figure 2E:
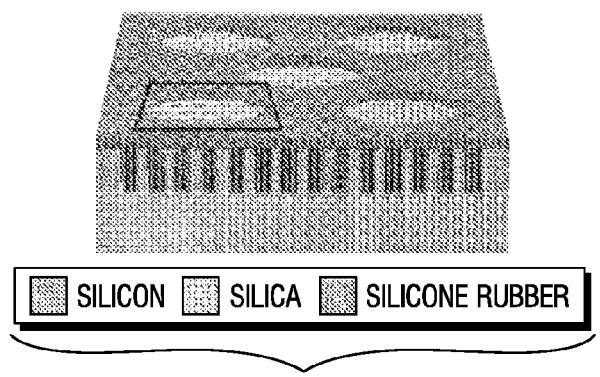
Figure 2G:
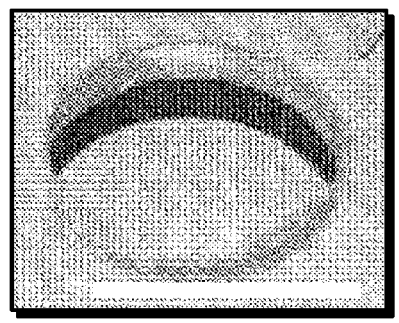
Figure 2H:
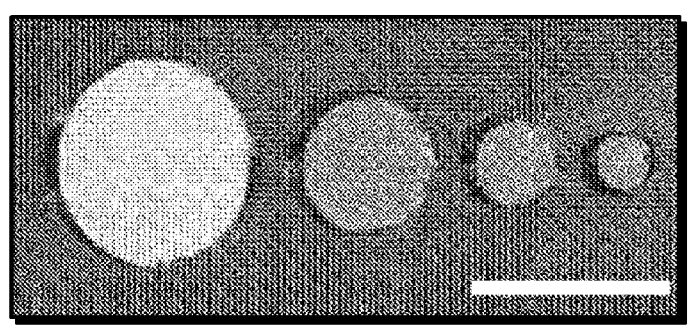

Unless otherwise specified, the words "a" or "an" as used herein mean "one or more".

In general terms, a novel size-exclusion strategy is presented based on Mesoporous Silica Chips (MSC) for the efficient removal of the high molecular weight proteins and for the specific isolation and enrichment of low molecular weight species present in complex biological mixtures. In combination with mass spectrometry profiling, significant improvement and optimization of the specific harvesting efficacy of the MSC is presented.

A method is provided wherein components in a sample can be fractionated or separated. In an exemplary method embodying principles of the present invention, a substrate is provided which includes a mesoporous material having two or more domains, and the presence of the two or more domains allows for the separation and/or fractionation of the components in the sample into the two or more domains by contacting the mesoporous material with the sample. The number of domains present on a single mesoporous material is limited only by the physical size of the material, and can number in the thousands.

Mesoporous materials can be used for fractionation, stabilization, and storage of low-molecular weight biomolecules that are present in very low concentration in complex biological fluids. The mesoporous materials can be designed to possess desired physical and chemical features such as porosity, pore size, pore structure, and surface properties to selectively fractionate and enrich biomolecules. The fractionated biomolecules can be stabilized once captured in the pores of mesoporous materials, and the stabilization can be independent of storage temperature. Hence, mesoporous materials can be used to fractionate, stabilize, store, and transport fractionated biomolecules for on-site or off-site application.

Exemplary embodiments of mesostructured materials include mesoporous materials such as nanoporous silicon and nanoporous oxide materials such as nanoporous silica. Exemplary mesoporous materials have pore diameters of between about 2 nm and about 50 nm. Nanoporous materials typically encompass a range from about 1 nm up to about 1000 nm. See J. Roquerol et al. "Recommendations for the characterization of porous solids (Technical Report)" *Pure & Appl. Chem.*, 66 (1994) 1739-1758.

Mesoporous materials can be fabricated by a surfactant-templated sol-gel process, for example. The obtained materials can be films, wafers, particles, powders, microchips, etc. The mesoporous materials can be differentiated by their physicochemical properties such as pore size, pore structure, porosity, and functional groups. For example, the mesoporous materials can be multi-domain chips. The chips can be used for fractionation and enrichment of biomolecules in a selective molecular range or in multiple selective molecular ranges.

The physicochemical properties of the mesoporous materials can function to stabilize the captured biomolecules, and prevent denaturation or degradation of captured biomolecules. Biomolecules fractionated from multiple selective ranges can be stabilized in a single multi-domain chip.

The fractionation operation can be parallel or sequential. The physicochemical properties of the mesoporous materials can be correlated with their fractionation properties and identified by molecular cut-offs. The fractionated biomolecules can be stabilized once captured in the mesoporous materials. The mesoporous material may function as a molecular cut-off.

The fractionated biomolecules can be stabilized once captured in the mesoporous materials. The captured biomolecules can be stabilized when the physicochemical properties of the mesoporous materials inhibit the activity of lytic enzymes. The captured biomolecules can be stabilized when the physical dimensions of the nanofeatures of mesoporous materials are smaller, comparable, or bigger than lytic enzymes. The captured biomolecules can be stabilized due to chemical properties of the mesoporous materials. The mesoporous materials can be used as storage containers of fractionated biomolecules for long periods of time. The mesoporous materials can be used to transport biological samples to remote sites and for off-site application.

The mesoporous materials can be utilized to sequester desired low-molecular weight biomolecules present in very low concentration in samples of complex biological fluids. The sample can be any biological fluid derived from a living body including, but not limited to, blood serum, blood plasma, blood, urine, seminal fluid, seminal plasma, pleural fluid, ascites, nipple aspirate, feces, saliva, cerebrospinal fluid, etc. The body from which the biological sample is taken may have a physiological condition that can be identified by methods embodying principles of the present invention.

The components in the sample can be numerous, and can include, but are not limited to, proteins, antigens, antibodies, proteins, protein fragments, RNA, DNA, etc. The components may have differing molecular weights. For example, the molecular weight of a first component can be lower than the molecular weight of a second component.

Exemplary methods of the present invention can include the step of extracting the first component from the mesoporous material and washing the mesoporous material subsequent to contacting the mesoporous material with the sample. It is possible that one domain on the mesoporous material adsorbs the first component. The domains on the mesoporous material can have a modified surface that is electrically charged or modified with organic functional groups or inorganic metal ions, or both, and the modified surface of one domain can be different from the modified surface of another group.

The components which are separated into the domains on the mesoporous material may be analyzed by methods which include, but are not limited to, mass spectrometry, gel electrophoresis, chromatography, bioassay, or a combination thereof, and the mass spectrometry can be MALDI-TOF mass spectrometry, LC/MS mass spectrometry, ESI-MS mass spectrometry, tandem mass-spectrometry, and/or SELDI mass spectrometry.

Mesoporous materials such as mesoporous films can be produced by the evaporation-induced-self-assembly (EISA) procedure, and as a result can have a tunable and pre-determinable pore size, texture, and structure. The EISA synthesis route is adaptive and makes it possible to immobilize or embed organic functional groups or inorganic metal ions and to modify surface physicochemical properties, such as pore size, volume, texture, and structure. The pore morphology can be pre-determined to be, for example, cubic, hexagonal, honeycomb-like, tubular, circular, and/or oblong. The pore size can also be the same or different among the various domains, and can be, in one example, between 1 nm to 30 nm, and in another example, between 2 nm and 15 nm, more preferably between 2 nm and 12 nm. Pore volume can also be pre-determined, can be the same or different among the various domains, and can be in one example, between 4 and 15 nl.

Examples of the mesoporous materials include mesoporous chips. Exemplary mesoporous chips can generate a multiplicity of peaks for cross-correlation and multivariate profile analysis centigrams. The correlation between physical and chemical features (porosity, pore size and structure and surface properties) of the chips and the biomolecular fractions can be established. The capture of desired biomolecular fractions is effective at extremely low concentration ranges of the target biomolecules even in the presence of the overwhelming background of highly abundant proteins in serum, plasma, and whole blood. The chips allow for selective capture and enrichment of samples as small as 10 µl with excellent rapidity, require no sample pre-processing, and are highly reproducible.

The chips are not limited to mesoporous silica films. Other surfactant-templated mesoporous materials may also be applied. Mesoporous silica chips are described here as an exemplary embodiment.

Mesoporous silica films can be fabricated on a substrate such as silicon or a glass wafer by coating, such as spin-coating, dip-coating, printing, or deposition. The coating solution may be a sol-gel solution of an orthosilicate compound, such as a silica source, solvent, water, acid or base, and surfactant polymer at a certain ratio. The surfactant-template can be removed by chemicals or by heating after coating. The obtained mesoporous films may possess different physicochemical properties such as pore size, pore structure, porosity, functional groups, etc. The mesoporous film may be differentiated by morphology or structure. The morphologic or structural variation can be induced during the synthetic procedure.

The obtained mesoporous silica films can be treated in oxygen plasma. In one embodiment, the mesoporous silica films are treated in oxygen plasma prior to conjugating organic functional groups. This helps to ensure the hydrophilicity of the silica film. Furthermore, it is believed that the silanol (Si—OH) groups on the surface of the mesoporous silica films act as a convenient point for further organic functionalization of the film, though the high temperature during calcinations process may cause portions of the surface silanols groups to be extensively dehydrated, resulting in a substrate incompatible with potentially conjugating organosilane groups. However, the oxygen plasma treatment restores the defective points (Si—H on the mesoporous silica and generates a high density of Si—OH groups.

The mesoporous silica films can be differentiated by adapting different swelling agents in the synthesis procedure. The mesoporous silica films can also be differentiated by their chemical modification or biological conjugation with different functional groups or molecules, for example to permit the selective enrichment of low-abundance and low molecular weight biomarkers, such as those found in human serum. For example, organic functional groups with various charges and polarities, including but not limited to phosphate, amine, thiol, carboxy acid, sulfate acid and epoxy moieties, may be conjugated within the nanoporous matrix. Alternatively, the mesoporous film may be conjugated with chemical functional groups on the pore surface. For example, silage compounds with the functional groups aminopropyltriethoxysilane (APTES) and mercaptopropyltriethoxysilane may be used for amine attachment. Likewise, the surface of mesoporous silica chips can be coated by hydrophobic molecules such as, in one example, hexamethyldisilazane.

In addition to the organic functional groups discussed above, the present invention contemplates the use of inorganic metal ions to functionalize the surface of the mesoporous silica. For example, metal ions such as gallium, zirconium and titanium (e.g. $Ga^{3+}$, $Ti^{4+}$ and $Zr^{4+}$) may be immobilized on mesoporous silica chips as a means to improve the detection limit of very low concentration peptides, particularly low molecular weight phosphoproteins. The chemical and physical properties of the composite mesoporous thin films may then be characterized by X-ray diffraction, transmission electronic microscopy, X-ray photonic spectroscopy, energy dispersive X-ray spectroscopy and ellipsometry.

Post-functionalization of the mesoporous silica films effectively reduces the detectable concentration threshold by removing dominant high molecular weight proteins. Furthermore, capture selectivity may be increased, enhancing the ability of the inventive mesoporous films to resolve the difference between the modified protein and its unmodified precursor, where the mass to charge ratio is nearly identical and may obscure the desired phosphopeptide peak. The functionalized mesoporous silica films of the instant invention thus demonstrate tunable selectivity coupled to a platform capable of much higher throughput.

The mesoporous silica films can be patterned or masked to work as biomolecular fractionation chips. The chips can be used for fractionation and enrichment of the selective molecular range species using an on-chip fractionation strategy. The chips with different physicochemical properties can be integrated in a single chip to form a combinatorial multidomain chip. The domains can be distinguished by their physicochemical properties, and may be from the same film or different films. By using micro/nanofabrication techniques, thousands of domains can be fabricated on a single chip.

The combinatorial multi-domain chips can be masked or patterned to define sample area, and/or isolate samples. Mask materials can be photolithography compatible polymers/photoresists, molded PDMS films, silicone rubbers, and so forth. The mask can be made to match a multichannel pipette system for automation. The masks can be removable. The chips can be made so they are able to be directly inserted into to a measurement system such as MS.

The physicochemical properties can be characterized by many methods. For example, the thickness and porosity of obtained films can be determined by a spectroscopic ellipsometry. The surface area and pore size distribution of the mesoporous films can be measured using $N_2$ adsorption-desorption isotherm. The morphology and structure can be measured by Transmission Electron Micrographs of the sections or SEM. Small angle X-ray scattering spectra (SAXS) can be used to determine the structural symmetry. The physicochemical properties of the chips or domains can be correlated with their fractionation properties and identified the molecular cut-offs.

While the invention has been described in detail with reference to exemplary embodiments thereof, it will be apparent to one skilled in the art that various changes can be made, and equivalents employed, without departing from the scope of the invention. The foregoing description of the preferred embodiments of the invention has been presented for purposes of illustration and description. It is not intended to be exhaustive or to limit the invention to the precise form disclosed, and modifications and variations are possible in light of the above teachings or may be acquired from practice of the invention. The embodiments were chosen and described in order to explain the principles of the invention and its practical application to enable one skilled in the art to utilize the invention in various embodiments as are suited to the particular use contemplated. It is intended that the scope of the invention be defined by the claims appended hereto, and their equivalents. The entirety of each of the aforementioned documents is incorporated by reference herein.

EXAMPLES

The present invention will be more concretely explained below with reference to the following non-limiting Examples.

Example 1

Example 1.1

Fabrication of Mesoporous Proteomic Chips

The coating solution was a mixture of a tetra-ethyl-orthosilicate (TEOS) as silica source, solvent, water, acid, and surfactant polymer at designed ratio. The stock solution was prepared first: 10 g of TEOS (Sigma Aldrich) was first added to a glass bottle followed by 8.5 g of absolute ethanol (Sigma Aldrich). Then, 1 g deionized (DI) water was added, and finally, 0.04 g of 0.07M HCl (Sigma Aldrich) solution was added. This mixture was stirred and heated to 60° C. for 90 minute. Then, the solution was cooled down, and aged at least two days before use. For Pluronic F38, F88, F108 and F127 tri-block copolymer (BASF) which are solid at room temperature, 4 g of the triblock copolymer was first dissolved in 8 g ethanol and 4 g water. Next the 8.7 g stock solution and the 1.2 g 1M HCl solution were added. The mixture was then vibrated on a Vortex mixer for 1 min, and processed by ultrasound for 5 min. The obtained clear solution was aged for 1 day before spin-coating. The film was made by spin-coating: 1.5 ml of coating solution was dispersed onto a 4" silicon wafer (Silicon Quest International, Inc, CA) and spun at 600 rpm for 5 s, and then the spinning speed was increased to 3000 rpm for 30 s. The coated wafer was placed in an oven, heated to 80° C., aged for 15 h. The temperature was then raised to 425° C. at a rate of 5° C./min. The wafer was kept at 425° C. for 4 h, and slowly cooled down to room temperature. The SU-8 photoresist mask was patterned on the mesoporous silica chips (hereinafter, "MSCs") using standard photolithography to form a hydrophobic ring to confine the sample within the non-covered area. Fabrication of Polydimethylsiloxane (PDMS) masked MSC was started by molding the PDMS film, and then bonded to MSCs (See FIG. 1).

Example 1.2

Protein Fractionation, Stabilization and Storage

Figure 6A:
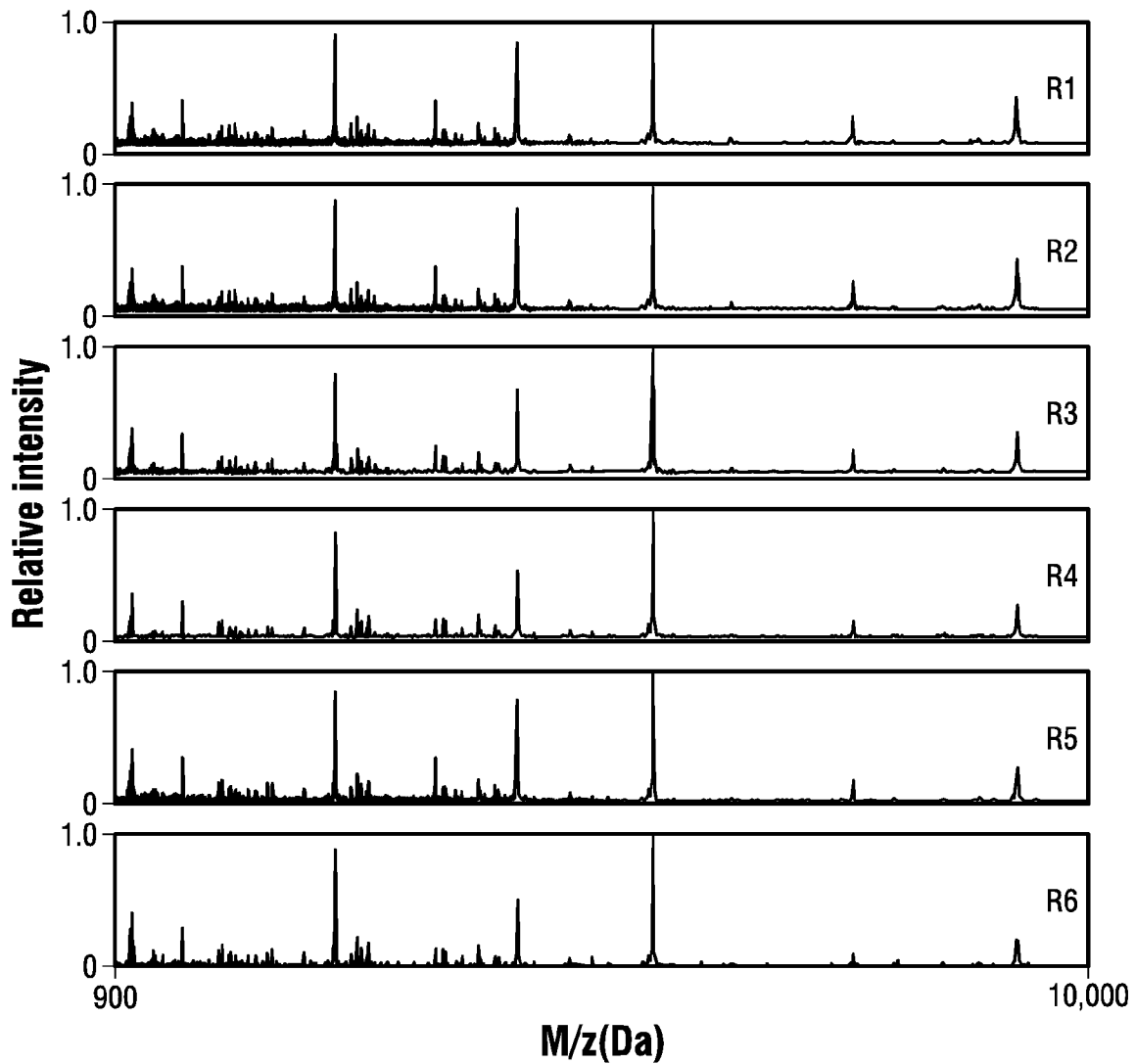
FIG. 6 shows the reproducibility of protein fractionation. Panel a shows the MALDI profiles in the mass range 900 to 10000 Da of 6 independently processed replicates of fractionated serum show a highly reproducible peak identity and intensity. Panel b the protein recovery from 6 independent experiments performed with the same chip type using the same settings (temperature, time, washings). There is a small fluctuation in the amount of protein recovered but there is no statistically significant difference among the experiments.
Figure 6B:
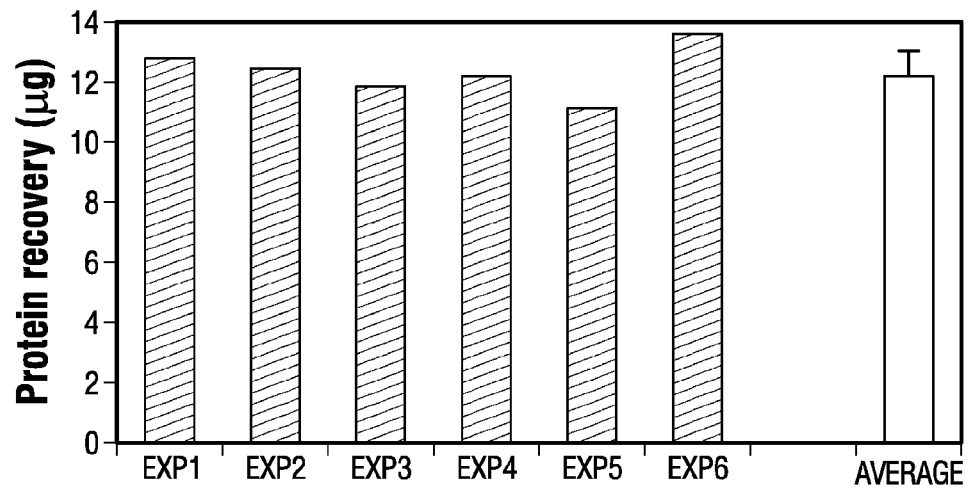
Figures 3, 9A:
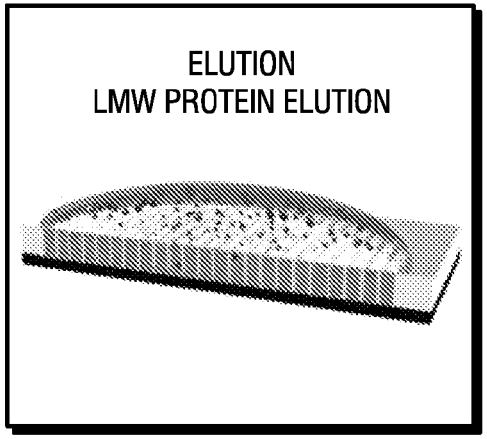
Figure 10A:
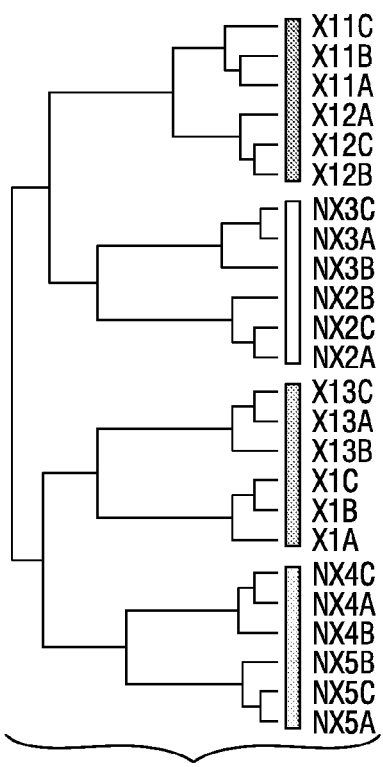
FIG. 10 shows the effect of pore sizes and chemical properties on serum peptide harvesting. Panel a shows a dendogram of the unsupervised two-way hierarchical clustering. Each set of MSCs is uniquely identified. The dark and light blue rectangles represent large and small pores, respectively. The green and red rectangles represent the hydrophobic- and TMB generated-MSCs, respectively. Panels b-d show supervised hierarchical clustering and specific recovery pattern for each set of nanochips as indicated in the figure (the complete clusters with the mass lists are presented in FIG. 23). The relative intensity is gradually indicated with red squares (high intensity), black squares (median) and green squares (low intensity or absence of a peak). Panels e-h show the MS profiles of crude serum and purified peptides and proteins using a multi-chips strategy. Panel i shows the comparison of the number of MS peaks detected in crude serum and after fractionation on selected nanochips. The multi-chip strategy increases more than 3 times the number of non redundant LMW peaks detected in serum.
Figure 10B:
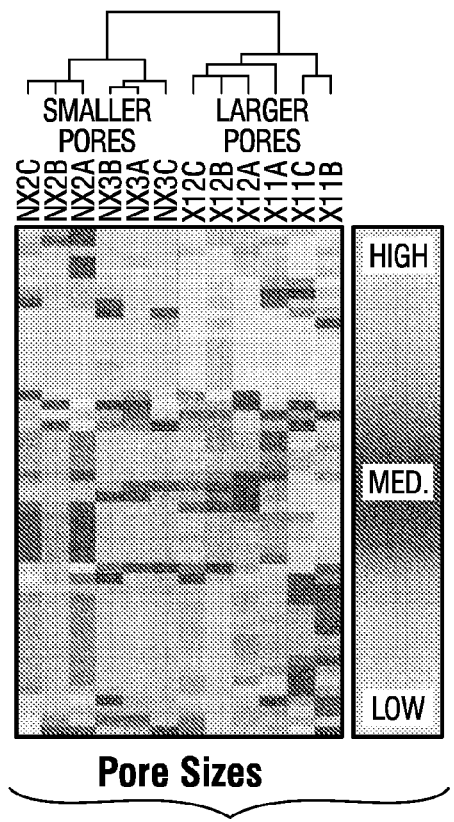
Figure 10C:
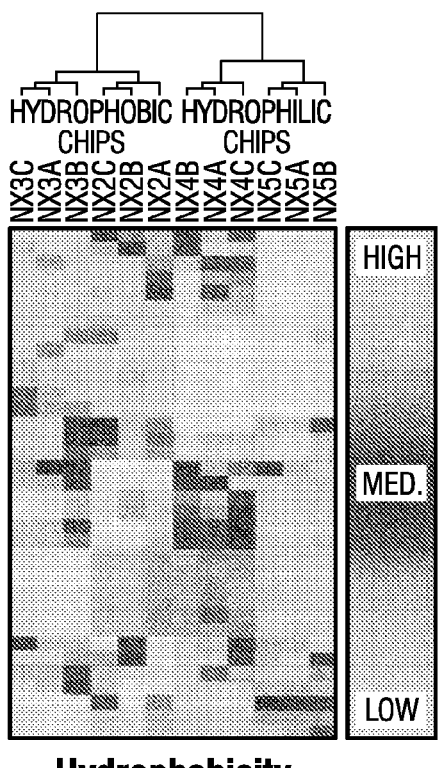
Figure 10D:
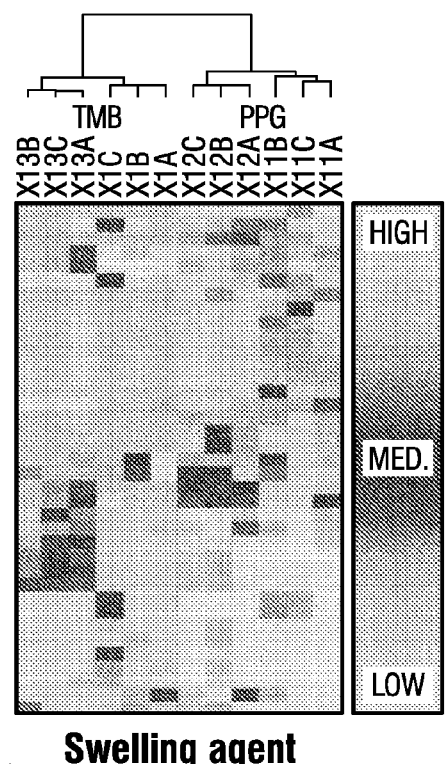
Figure 10E:
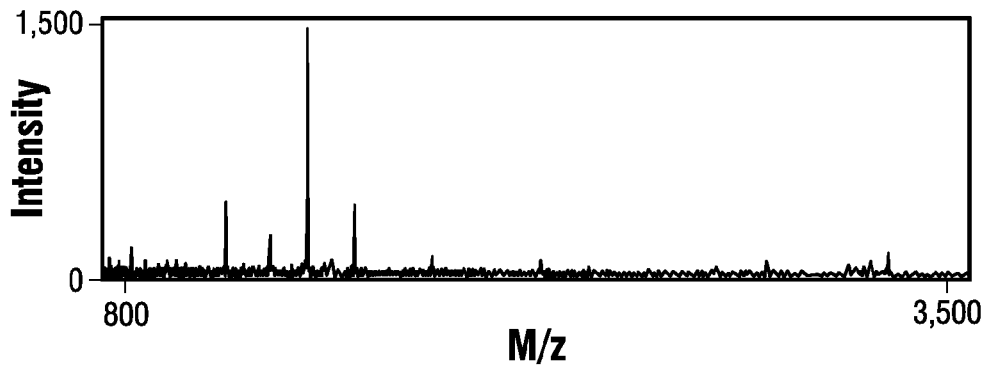
Figure 10F:
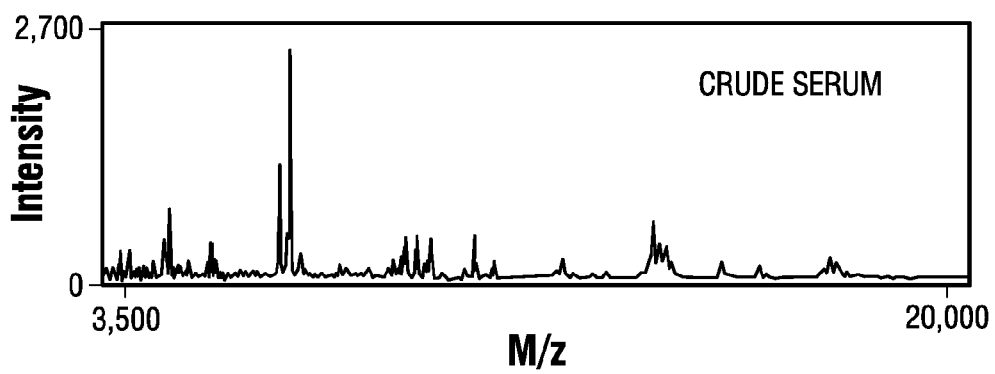
Figure 10G:
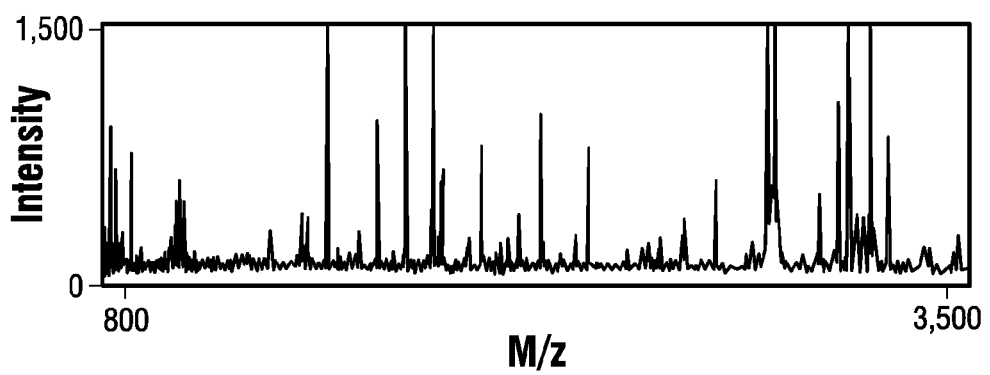
Figure 10H:
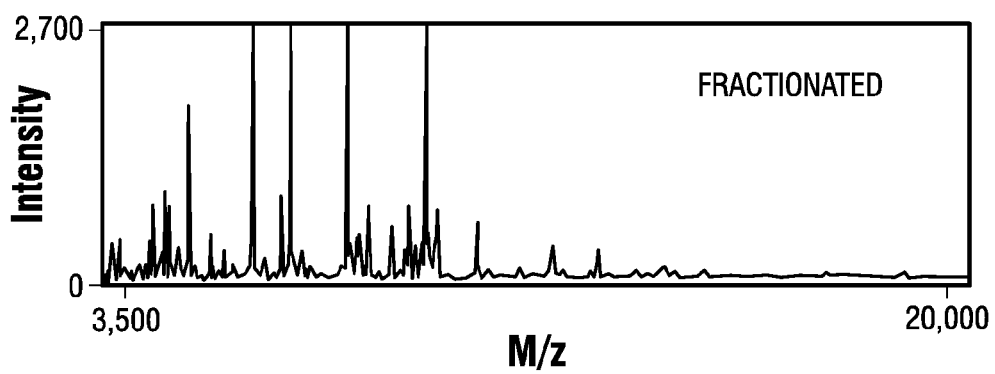

The MSCs for protein fractionation and enrichment of the LMW species were employed using a fast three step on-chip fractionation strategy, and showed the correlation between pore size, the molecular weight of the trapped species, and the enrichment of the LMW standards. The use of MS profiling to correlate a disease with the specific changes in the circulating proteins is a promising tool to improve diagnosis, to allow the design of personalized therapies and to follow their efficacy in real time and with low invasiveness. However, several publications reported that pre-analytical sample management may lead to significant alterations of the proteomic profiles and the generation of possible artifacts. Reproducibility and reliability of the approach are crucial for any clinical applications. The consistency of the on-chip fractionation assay was assessed at different working temperatures (FIG. 3), and by reproducing the same experiment in 6 replicates with 6 aliquots of the same human serum sample. After fractionation, the spectra of the replicates showed a highly reproducible MS signal (See FIG. 6a). The reproducibility of the procedure was statistically evaluated for the relative intensities of the detected peaks in the range of 900 to 20000 Da. The regression curves and equations comparing the peak intensities recovered from the replicates in crude and fractionated serum are illustrated in FIGS. 10f and 10h respectively. The general variability of the peak signals measured by the average CV was estimated at 12.7% for crude serum and 14.2% after fractionation. The statistical evaluation of the data obtained indicated marginal variations due to the internal variability of the MALDI instrument and revealed that the on-chip pretreatment did not induce any alteration of MS protein profiles. To address the issue of protein stability in the nanopores MSCs were incubated with human serum, dried the chips after the washing steps, and stored them for 3 weeks. The stability of peptides and proteins was confirmed using samples eluted from chips after 3 weeks storage at room temperature (see FIG. 3e). Compared with a freshly fractionated sample of the same serum, the results demonstrated similar peptide patterns as shown above. It is hypothesized that LMW species trapped inside the nanopores were preserved from degradation through the exclusion of the proteases from the nanopores, or by the steric inhibition of their proteolytic activity in the confined space of the nanopores. The ability to impede further degradation of the proteins and peptides once they are captured mesopores is a crucial property for the translation into the laboratory clinical practice. It enables the establishment of simple sample acquisition and storage protocols that address the problem of "artifacts" that has plagued prior approaches to proteomics and peptidomics. With prior methodologies, differences in blood sample acquisition, time elapsed before contact of the serum onto the capture surfaces, environmental and storage temperatures all resulted in the degradation-induced appearance of peaks that confounded the analyses and rendered meaningless the use of the profiles to derive any diagnostic or otherwise medically significant information. The fundamental, clinically enabling advantage of the present approach is that whole blood can be drawn and directly placed onto the MSC, resulting in a pattern of stored information that is reproducible and stable in time, regardless of a broad range of temperature and environmental variables.

Example 1.3

Protein Fractionation Experimental Procedure

The MSC surface was wetted using isopropanol, washed with sterile $H_2O$, and air dried. For each experiment, a sample amount of either plain human serum, or a solution containing different dilutions of recombinant peptides and proteins, was pipetted into the circular area defined by the different masks. Unless otherwise specified, for all the experiments shown in the paper 10 μl of sample were used for each analysis. The samples were incubated for 30 minutes in a wet chamber (100% humidity) to prevent sample evaporation. In order to identify the best working condition experiments were performed at either 4° C., 25° C. (RT), or 37° C. RT was selected as the optimal temperature and used for all the experiments showed in the paper. MSCs were washed 5 times with 15 μL of sterile, deionized water, allowing the droplets to rest on the surfaces for 0.5 minute for each wash. The chips were dried after the washing steps, and stored for up to 3 weeks. Peptides and proteins were eluted by using 10 μl of a 1:1 mixture of acetonitrile and 0.1% trifluoroacetic acid (TFA) (v/v) (Sigma) and pipetting the solution on the chip for approximately 1 minute. Aliquots of 1 μL of the mix of serum extracts and matrix solution were deposited on a MALDI sample plate and allowed to dry prior to mass spectrometric analysis. Protein content in samples was measured using a microBCA assay (Pierce, Rockford, Ill.) and read with the absorbance at 562 nm on a UV/Vis Spectrophotometer (Spectra Max M2, Molecular Devices). Absorbance values were converted into protein amounts using the formula calculated through a standardization curve. For the microBCA assay, 3, 5, 8, 10, and 12 μL of the sample for washes 1-5 respectively and 3 μL of the elution sample were diluted in water to make 500 μL. This diluted protein was mixed with 500 μL, of the microBCA buffer and incubated for 1 hour at 60° C. The samples were allowed to cool to room temperature and then read on the spectrophotometer.

Example 1.4

Mass Spectrometry

A matrix solution of 5 mg/ml α-cyano-4-hydroxycinnamic acid (αCHCA, Sigma) in a 1:1 mixture of acetonitrile and 0.1% TFA(v/v) and a saturated matrix solution of trans-3,5-dimethoxy-4-hydroxycinnamic acid (SA, Sigma) in 2:1 mixture of acetonitrile and 0.1% TFA was used for Low Molecular Weight (LMW) and High Molecular Weight (HMW) peptides and proteins, respectively. Each sample was mixed with the appropriate matrix in a 1:3 ratio, and spotted in duplicate onto the MALDI plate. Mass spectra were acquired on a Voyager-DE™-STR MALDI-TOF (Applied Biosystems, Framingham, Mass.) mass spectrometer in liner positive-ion mode, using a 337 nm nitrogen laser. Samples were evaluated at two m/z ranges. For the m/z range of 800-10,000 Da, settings were optimized at acceleration voltage 20 KV, grid voltage 19 KV, guide wire voltage 1 KV, delay time 180 ns, and low-mass gate 800. For the m/z range of 3,000-100, 000 Da the instrument was optimized at acceleration voltage 25 KV, grid voltage of 23.25 KV, guide wire voltage 6.25 KV, delay time of 500 ns and low mass gate 3,000. Each spectrum was the average of 300 laser shots. The spectra were calibrated externally using the ProteoMass standards of peptides and proteins (Sigma) in each mass range.

Example 1.5

Data Processing and Statistics

The raw spectra were processed with the Voyager Data Explorer software version 4.0 (Applied Biosystems) and the data were exported to SpecAlign software for pretreatment. All spectra were aligned using the PAFFT correlation method and intensity was normalized to total ion current (TIC). The peak detection was performed with a height ratio of 2 with 0.3% of the mass window and the baseline was corrected and the negative values were removed prior to analysis.

Hierarchical clustering was performed using Cluster software and visualized with Treeview software. MALDI MS Data (M/z peak intensities) were log-transformed, normalized and median centered. Pearson correlation was used to calculate the distance between the samples, and complete linkage clustering was performed. For supervised hierarchical clustering, an independent Student t-test was used for comparison between groups (n=2 groups) for each detected MS peak. A P value of 0.02 or lower was considered significant to select differentially harvested peptides and proteins among the different mesoporous proteomic chips (Large pores vs. Small pores, Hydrophobic vs. Hydrophilic, TMB vs. PPG swelling agents). This statistical method was used to analyze and produce the data presented in FIGS. 10 and 23.

Example 2

Example 2.1

Fabrication of Nanoporous Proteomic Chips

The coating solution was prepared by starting with the hydrolyzed silicate precursor solution. Firstly, 14 ml of tetraethylorthosilicate (TEOS) was added into the mixture of 17 ml of ethanol, 6.5 ml of deionized water and 2 ml of 2M HCl under strong stirring. The silica sol-gels were ready for use after being heated at 75° C. for 2 hours. The polymer template solutions were prepared by the addition of the calculated amount of triblock polymer (BASF: L31, L35, L64, 1.5 g of L121, P123, F38, F88, F108, 1.8 g of F127) or 1 g of CTAB in 10 ml of ethanol under room temperature. After dropping 10 ml of silicate precursor into the polymer solution, the mixture was kept stirring for another 2 hours (30 minutes for CTAB). For the preparation of mesoporous silica films with large pore size, a swelling agent, Polypropyleneglycol (PPG) was added in the ethanol solution of polymer before mixing with silicate. 1 ml of the coating solution was deposited on a 4" silicon wafer (Silicon Quest International, Inc., CA) followed by spin-coating at a speed of 2500 rpm (1000 rpm for using CTAB). The coated wafers were placed in an oven and aged for 15 hours at 80° C. Then the temperature was raised to 425° C. at a rate of 1° C./min and kept at 425° C. for 5 hours to completely remove the organic components before gently cooling down to room temperature. Oxygen plasma treatment was carried out in a Plasma Asher (March Plasma System) with a $O_2$ flow rate at 80 sccm and a power of 300 W for 10 minutes. Coating of hexamethyldisilazane (HMDS) was performed in a HMDS vapor prime oven (YES) at 150° C. for 5 min.

Example 2.2

Characterization

The thickness and porosity of calcinated films were determined by a variable angle spectroscopic ellipsometer (J. A. Woollam Co. M-2000DI). Ellipsometric values, $\Delta$ and $\psi$ were measured from wavelength range 300-1000 nm at three incidence angles, 55°, 60°, 65° respectively, and fitted using Effective Medium Approximation (EMA) model with WVASE32 software. X-ray diffraction (XRD) patterns were obtained on Philips X'Pert-MPD system with Cu K$\alpha$ ray (45 kV, 40 mA). 0-2$\theta$ scanning were recorded from all spin-coated films at 1 s/0.001° step over the angle range from 0.2° to 6°. Transmission electron microscopy (TEM) was used in requiring micrographs of the plane view of mesoporous silica thin films with FEI Technai (FEI Co.) at high tension of 200 kV. The surface area and pore size distribution of the mesoporous films was measured using $N_2$ adsorption-desorption isotherm on a Quantachrome Autosorb-3B Surface Analyzer. The sample was prepared by scraping from 6-10 mesoporous silica chips. The sample was degassed at 3000° C. for over 12 hours, and the N2 adsorption-desorption isotherm was measured at 77 K over relative $P/P_o$ pressures range 0.015-0.995. The Brunauer-Emmett-Teller (BET) surface areas were determined over a relative pressure range of 0.05 to 0.3. Nanopore size distributions were calculated from the adsorption branch of the isotherms using Barrett-Joiner-Halenda (BJH) model. Contact angles of film surface were measured by a goniometer with captive bubble contact angle measurement.

Example 2.3

Experimental Procedure

The molecular weight standards were combined, dispensed in equal amounts, dried by vacuum centrifugation, and stored at −20° C. 10 µl of the standards solution was spotted onto the mesoporous surface of the MSC. The samples were incubated for 30 minutes in a wet chamber (100% humidity) to prevent sample evaporation. The chip surface was washed 5 times with 15 µL of sterile, deionized water. Proteins were eluted from the pores by using 10 µl of a 1:1 mixture of acetonitrile and 0.1% trifluoroacetic acid (TFA) (v/v).

Example 2.4

Fractionation Procedure

Twenty-six peptides and proteins were selected with broad range of molecular weights (900-66 500 Da), pI (pI 4.0-10.2), and structure. Identity and purity of each peptide and protein was verified by MS and combined, dried by vacuum centrifugation, and stored at −20° C. The molecular weight standards solution was prepared in 135 µl of sterile, deionized water.

The chip surfaces were wetted using isopropanol, washed with sterile $H_2O$ and air-dried. Human serum was dispensed with a micropipette onto the surface of the wafer into the circular area defined by the masks. Unless otherwise specified, 10 µA of sample was used for each analysis. The samples were incubated for 30 minutes in a wet chamber (100% humidity) to prevent sample evaporation. The MSCs were washed 5 times with 154 of sterile, deionized water. Elution was performed using 10 µl of a 1:1 mixture of acetonitrile and 0.1% trifluoroacetic acid (TFA) (v/v) (Sigma). Proteins were eluted from the pores by using 10 µL of a 1:1 mixture of CAN and 0.1% TFA (v/v).

Example 2.5

Mass Spectrometry

A matrix solution of 5 mg/ml α-cyano-4-hydroxycinnamic acid (αCHCA, Sigma) in a 1:1 mixture of acetonitrile and 0.1% TFA(v/v) and a saturated matrix solution of trans-3,5-dimethoxy-4-hydroxycinnamic acid (SA, Sigma) in 2:1 mixture of acetonitrile and 0.1% TFA was used for LMW and HMW peptides and proteins, respectively. Each sample was mixed with the appropriate matrix in a 1:3 ratio, and spotted in duplicate onto the MALDI plate. Mass spectra were acquired on a Voyager-DE™-STR MALDI-TOF (Applied Biosystems, Framingham, Mass.) mass spectrometer in liner positive-ion mode, using a 337 nm nitrogen laser. Samples were evaluated at two m/z ranges. For the m/z range of 800-10,000 Da, the settings were optimized at acceleration voltage 20 KV, grid voltage 19 KV, guide wire voltage 1 KV, delay time 180 ns, and low-mass gate 800. For the m/z range of 3,000-100,000 Da the instrument was optimized at acceleration voltage 25 KV, grid voltage of 23.25 KV, guide wire voltage 6.25 KV, delay time of 500 ns and low mass gate 3,000. Each spectrum was the average of 300 laser shots. The spectra were calibrated externally using the ProteoMass standards of peptides and proteins (Sigma) in each mass range.

Example 2.6

Data Processing and Statistics

The raw spectra were processed with the Voyager Data Explorer software version 4.0 (Applied Biosystems) and the data were exported to SpecAlign (Wong, J. W., Cagney, G., Cartwright, H. M., SpecAlign—processing and alignment of mass spectra datasets. *Bioinformatics* 2005, 21, 2088-2090, and Wong, J. W., Durante, C., Cartwright, H. M., Application of fast Fourier transform cross-correlation for the alignment of large chromatographic and spectral datasets. *Anal Chem* 2005, 77, 5655-5661) software for pretreatment normalized to total ion current intensity. The baseline was corrected and the negative values were removed prior to analysis. Hierarchical clustering was performed using Cluster software and visualized with Treeview software. The MALDI Data (M/z peak intensities) were log-transformed, normalized and median centered. Pearson correlation was used to calculate the distance between the samples, and complete linkage clustering was performed (Eisen, M. B., Spellman, P. T., Brown, P. O., Botstein, D., Cluster analysis and display of genome-wide expression patterns. *Proc Natl Acad Sci USA* 1998, 95, 14863-14868). For supervised hierarchical clustering, an independent Student t-test was used for comparison between groups (n=2 groups) for each detected MS peak. A P value of 0.02 or lower was considered significant to select differentially harvested peptides and proteins among the different nanoporous proteomic chips (Large pores vs. Small pores, Hydrophobic vs. Hydrophilic, TMB vs. PPG swelling agents).

Example 3

Example 3.1

Fabrication and Characterization of Mesoporous Proteomic Chips

The coating solution for the mesoporous silica thin films with various pore size and morphological properties were produced using different surfactant polymers as synthetic templates under acidic conditions. The pH of precursor solutions was controlled at 1.5 to prevent the precipitation of nanoporous silicate and balance the procedure between the silicate hydrolysis and condensation of hydrolyzed silicate to polymer micelle. In FIG. 7 are illustrated the schematics of the chemical composition of the coating solution during the production of the mesoporous silica films (FIG. 7*a-d*) and the assembly of the final chips (FIG. 7*e-f*). Manufacturing protocols were optimized in order to obtain the mesoporous silica chips with smooth, crack-free surfaces across 4" silicon wafers with a porous films' thickness from 700 to 900 nm. Porosity was related to the ratio between copolymer and TEOS, while the thickness was determined by many factors, including the concentration of surfactant, the spin-coating speed, and the aging time of the coating solution. The pore alignment was induced by strain during the spin-coating process (Rice, R et al., "Structural comparison of hexagonally ordered mesoporous thin films developed by dip- and spin-coating using X-ray reflectometry and other quantitative X-ray techniques", *Journals of Materials Chemistry* 2005, 15, 4032-4040].

Figures 1, 24A:
Figures 2, 24A:
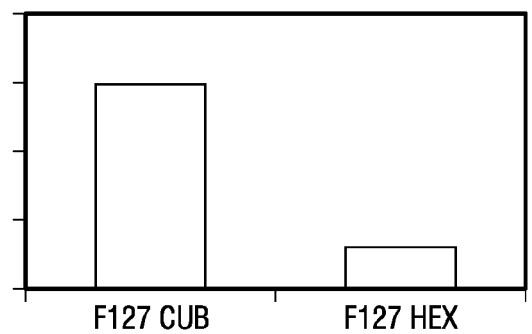
Figures 3, 24A:
Figures 4, 24A:
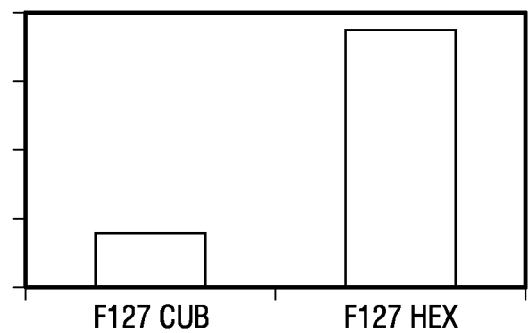
Figure 24B:
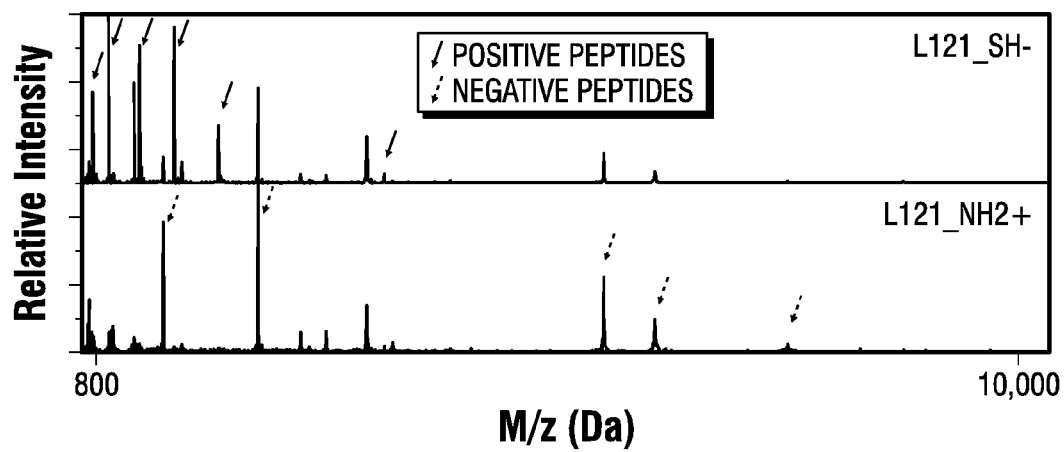
FIG. 24 is the physical characterization of the MSC. Panel a shows 1D XRD patterns and TEM images of plan-view (inserted) for mesoporous silica thin film prepared using CTAB, F127, and L121+50% PPG templates. Panel b shows pore size distribution from BJH adsorption for mesoporous silica thin films prepared using CTAB, F127, and L121+50% PPG templates. The corresponding adsorption/desorption isotherms are inserted.

Mesoporous silica thin films were first examined by X-ray diffraction (XRD) to display the periodicity and the organization of pore's nanostructure (FIG. 24*a*). The XRD pattern obtained with the CTAB silica thin film shows a peak for (200) reflection at 2.20° of 2θ with $d_{200}$=3.16 nm representing a periodic 3D cubic structure of silica nano-composite formed along the surface of the substrate. The XRD pattern of the F127 chip exhibits an ordered nanoporous texture as indicated by the highly intense (100) reflection peak at 2θ=0.99° ($d_{100}$=9.01 nm). The lower intensity peaked at (110) with $d_{110}$=6.30 nm and (200) with $d_{200}$=4.75 nm specifies the formation of a 3D honeycomb nanostructure. The XRD pattern for the L121 chip displays no peak in the small angle range illustrating the formation of disordered pores. Transmission electron microscopy (TEM) of each polymer template performed on the plane view confirmed the XRD results on the ordering and the nanostructure of the different chips. To determine the shape and the pore size distribution, N2 adsorption-desorption isotherms measurements were performed (FIG. 24*b*). According to the standard of the International Union of Pure and Applied Chemistry (Sing, K. S. W., Everett, D. H., Haul, R. A. W., Moscou, L., et al., Reporting Physiosorption Data for Gas Solid Systems with Special Reference to the Determination of Surface-Area and Porosity (Recommendations 1984). *Pure and Applied Chemistry* 1985, 57, 603-619), the isotherms can be classified as a Type II displaying a H1 hysteresis loop for CTAB chips, and as Type-IV with H2 hysteresis loops for F127 and L121 chips indicating the formation of ink-bottle shape nanopores. For this type of isotherm, adsorption branch of the isotherm can be used to calculate the pore size distribution using BJH method. All the BJH pore size distributions exhibits sharp peaks, which imply that both periodic and non-ordered nanophases created on the chips present uniform pore sizes.

Different chemical modifications were also studied. Oxygen plasma treatment was applied to ensure the hydrophilicity of the surface of the silica films, while HMDS coating was applied to make the surface hydrophobic. The hydrophilicity of the films was evaluated through contact angle measurement. The $O_2$ plasma treated films shows <15° contact angle, while the HMDS coated film showed >65° contact angle.

Example 3.2

Enrichment of the LMW Proteome

Figure 25A:
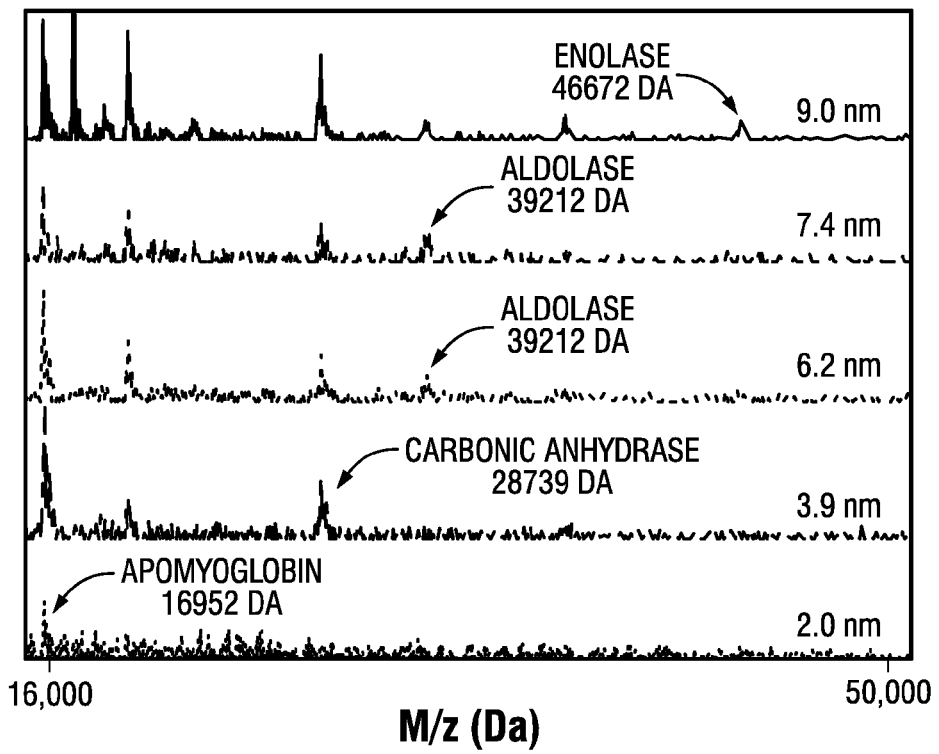
FIG. 25 shows the principle of MSC fractionation and LMW enrichment. In Panel a, after sample spotting on the surface, LMW proteins and peptides are trapped into the pores while the larger species remained outside the pores and are removed during the washing steps. The enriched fractions are then eluted and analyzed by MALDI. Panels b-g show the detection of the molecular weight standards by MALDI-TOF in the peptide (800 to 10000 Da) and in the protein range (3000 to 100000 Da). For the separated mixes of peptides (16 markers from 900 to 8500 Da) and proteins (16 markers from 3400 to 66500 Da), the profiles present a high level of detection for each species.
Figure 25B:
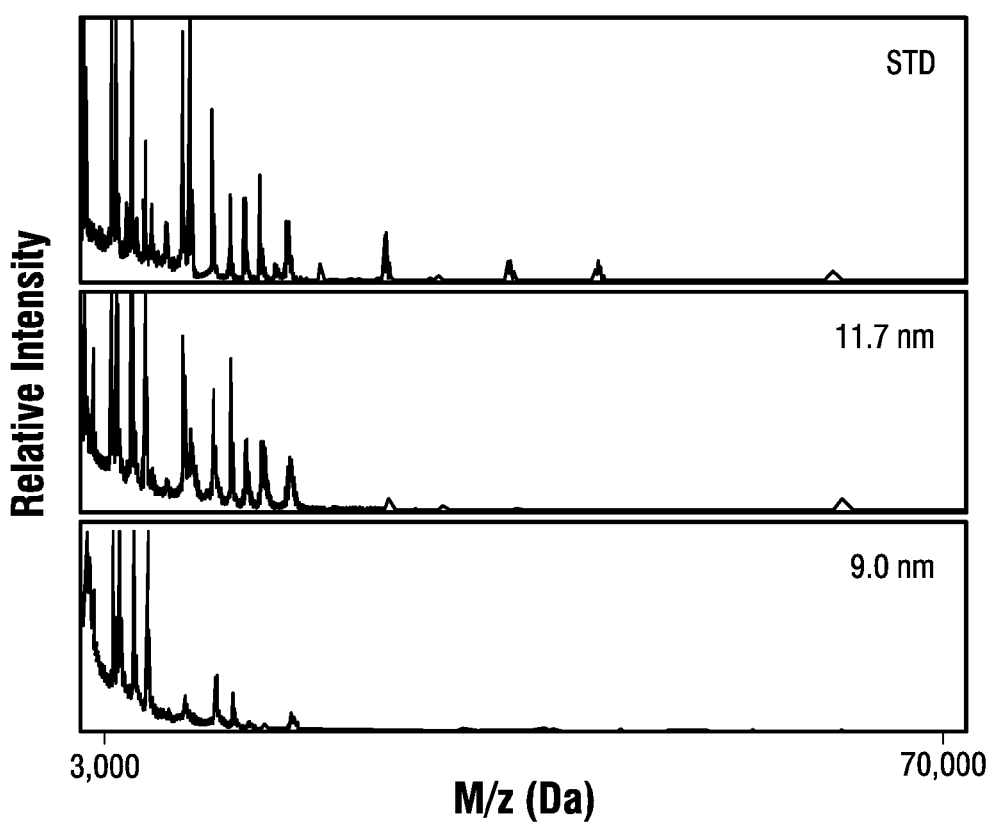
Figure 25C:
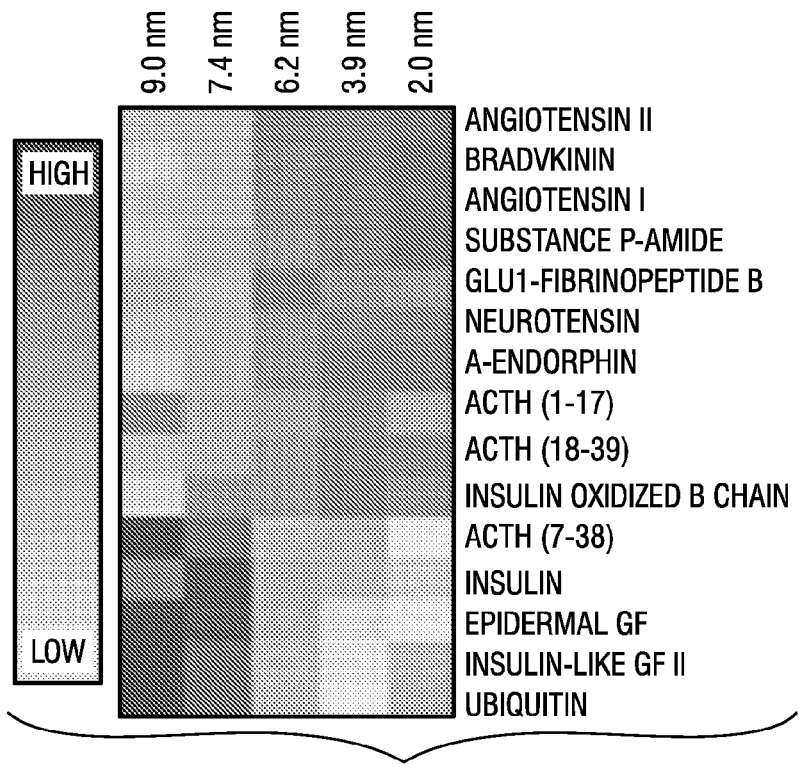
Figure 25D:
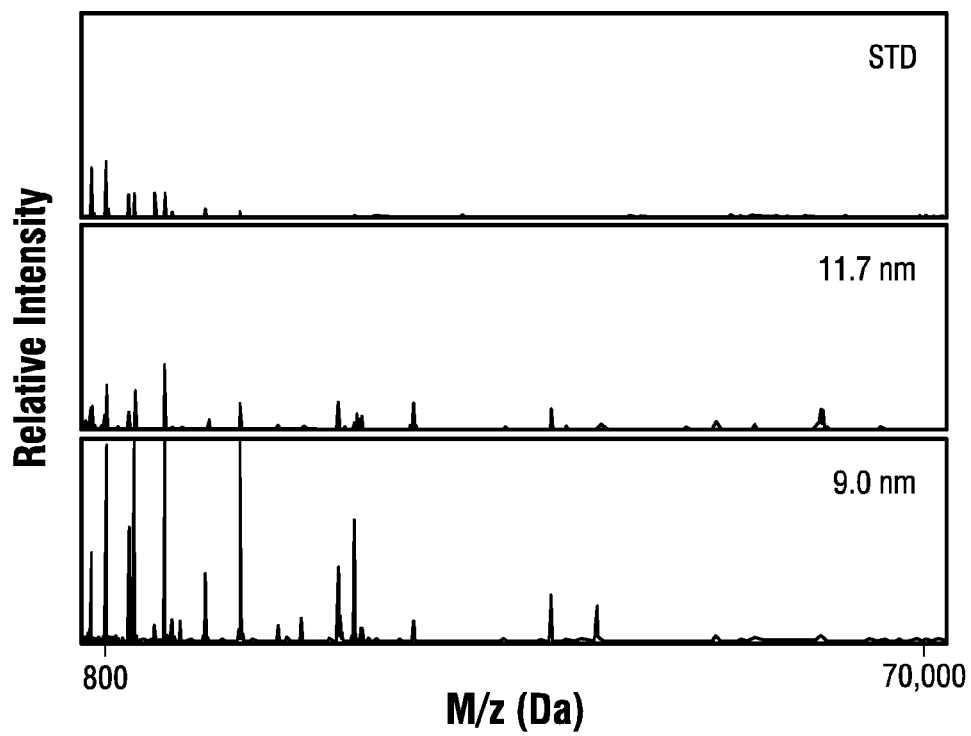

High-throughput mass spectrometry is a gold standard for protein expression profiling and for disease-related biomarker discovery. However, the current MS technologies are not able to profile the entire proteome and particularly the LMW species because of the interfering signals generated by the highly abundant HMW proteins (Tirumalai, R. S., Chan, K. C., Prieto, D. A., Issaq, H. J., et al., Characterization of the low molecular weight human serum proteome. *Mol Cell Proteomics* 2003, 2, 1096-1103). To address this limitation, a fractionation method was developed using the MSC to efficiently and specifically enrich the LMW proteome from complex biological samples. The principle of this fast on-chip fractionation strategy is shown in FIG. 25a: 1—The sample is spotted on the chip surface and LMW molecules are trapped into the pores during the incubation step; 2—The larger protein species remain outside the pores and are removed during the washing steps; 3—The enriched small molecules are then eluted from the pores and further analyzed by MS. In order to evaluate the fractionation and enrichment efficacy of this on-chip strategy, and to characterize how the physico-chemical properties of the chips correlate with their harvesting properties, 26 standard peptides and proteins were selected with a broad range of molecular weights (900-66,500 Da) and isoelectric points (pI 4.0-10.2), and combined to represent the diversity and complexity of biological samples (See FIGS. 4 and 5). FIGS. 25b and 25c show the high detection signals of the standards when separated into two different solutions for the peptide range (16 markers from 900 to 8500 Da) and the protein range (16 markers from 3400 to 66500 Da). When combined in a unique solution, the detection signal in the peptide range dramatically decreased while the larger proteins remained well detected (FIGS. 25d and 25e). This MS detection signal suppression in the LMW is due to the presence of large amount of well ionized HMW molecules such as Albumin and other large proteins. The suppression effect observed with the combined solution of molecular markers mimics the results obtained with MS analysis of complex body fluids such as serum and plasma. The results presented in FIGS. 25f and 25g demonstrate the ability to eliminate the big proteins and to increase significantly the detection of the LMW peptides and proteins.

The capacity of MS approaches to investigate low abundant proteins in biological samples composed of highly complex proteomes such as serum body fluids is a major issue for the detection of potential biomarkers. (Hanash, S. M., Pitteri, S. J., Faca, V. M., Mining the plasma proteome for cancer biomarkers. *Nature* 2008, 452, 571-579; Kulasingam, V., Diamandis, E. P., Strategies for discovering novel cancer biomarkers through utilization of emerging technologies. *Nat. Clin. Pract. Oncol.*, 2008, 5 588-599; Diamandis, E. P., Mass spectrometry as a diagnostic and a cancer biomarker discovery tool: opportunities and potential limitations. *Mol. Cell. Proteomics* 2004, 3, 367-378.) To assess the limit of detection of this technology, human serum sample was spiked with a known peptide (Neurotensin, 1673 Da) at different concentration levels before MSC fractionation and MALDI analysis. The results presented in FIG. 43 demonstrated the ability of the method to identify the spiked neurotensin in a concentration as low as 2 ng/mL.

Example 3.3

Tunable MSC Surfaces for Selective LMW Enrichment

Figures 1, 26A:
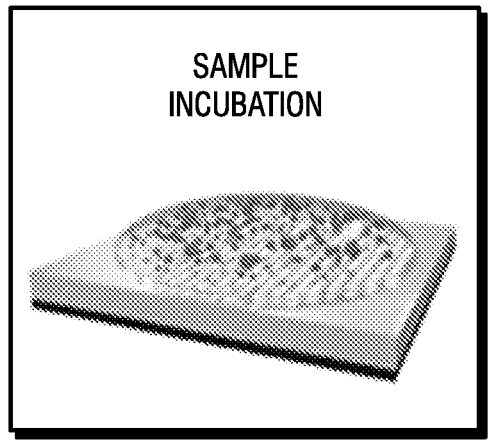
Figures 2, 26A:
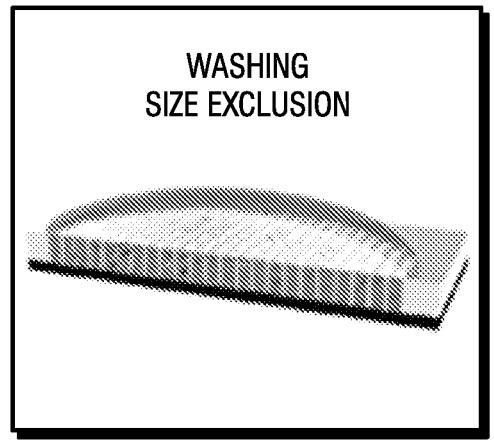
Figures 3, 26A:
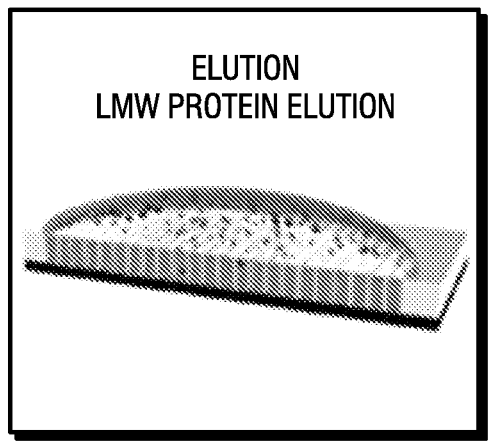
Figure 26B:
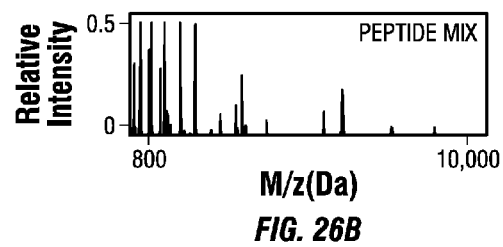
FIG. 26 shows the molecular cut-off and size-dependent enrichment of the MSC. Panel a shows a magnified view of the MALDI spectra demonstrating the characteristic molecular cut-off of each MSCs correlating to the pore size. Panel b shows the MALDI profiles of the HMW region for the standards solution before (Std) and after fractionation on 11.7 and 9.0 nm pores MSC. Panel c shows two-way hierarchical clustering of the peptide mix features among the different chips. The intensity of the red or yellow color indicates the relative peptide concentration. Larger pores enhanced the harvesting of bigger peptides (from 3600 to 8500 Da), while the small peptides (from 900 to 3500 Da) were preferentially recovered from the chips with smaller pores. Panel d shows the MALDI profiles of the LMW region for the standards solution before (Std) and after fractionation on 11.7 and 9.0 nm pores MSC.
Figure 26C:
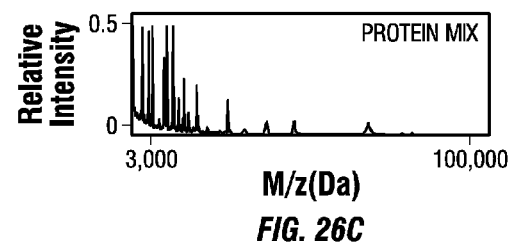
Figure 26D:
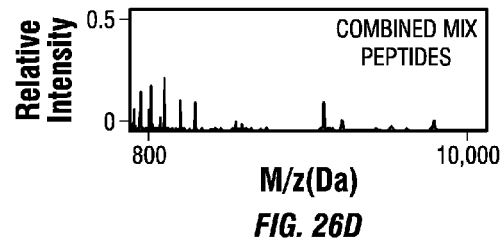
Figure 26E:
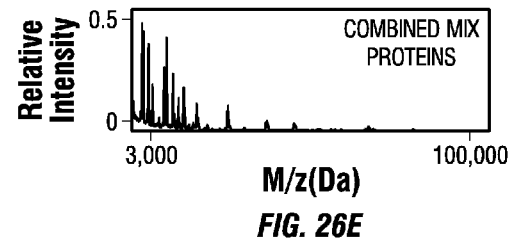
Figure 26F:
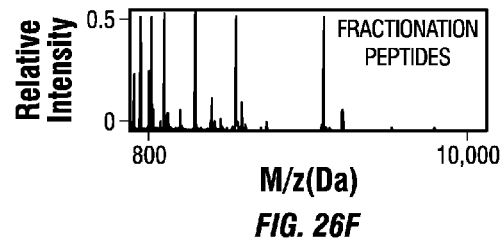
Figure 26G:
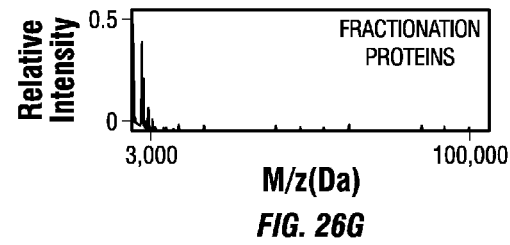

In order to assess the size-dependant depletion of high molecular weight (HMW) proteins, 6 proteomic chips were developed with pore sizes ranged from 2.0 nm to 11.7 nm. A variety of pore sizes was first obtained by using different polymer templates from ionic and non-ionic triblock copolymers with different volume ratio of hydrophilic/hydrophobic composition as shown in FIG. 24. Because of its highest hydrophobic/hydrophilic ratio among pluronic surfactants, L121 is capable of forming the mesoporous silica with the largest porosity (~65%) and pore size (6.2 nm). F127 template presents an intermediate pore size (3.9 nm) while the smallest pore size (2.0 nm) can be obtained using the ionic surfactant CTAB. In addition, by applying a different ratio of swelling agent such as Poly Propylene Glycol (PPG) to the L121 pluronic surfactant, the pore size has been further enlarged to obtain MSC with 7.4 nm, 9.0 nm and 11.7 nm. To evaluate the molecular cut-off and the enrichment properties of the different pore sizes, the solution of peptide and protein standards were fractionated on the set of MSC ranging from 2.0 to 11.7 nm. The removal of the large proteins is size dependant as illustrated by the gradual decrease of the molecular cut-off observed for the different chips (FIG. 26a). The silica surface with 9.0 nm pores did not completely exclude albumin, accordingly to its three-dimensional structure which exhibits an average size of 8 by 3 nm. This analysis demonstrates the size exclusion principle of the mesoporous chip fractionation, and reveals the limit of this depletion approach observed with the 11.7 nm pores which provides a similar MS pattern to the non-fractionated sample (FIG. 26b). In addition to the size-dependant depletion of high molecular weight (HMW) proteins, the on-chip fractionation of the standards solution displays a differential and selective enrichment of LMW species associated with the pore sizes. The two-way hierarchical clustering presented in FIG. 26c shows the LMW standards enrichment pattern obtained with the different MSC. Even if all the peptides are below the molecular cut-off of the chips, there is a positive correlation between the pore sizes and the molecular weight of the trapped species. The MSC with large pores, up to 9 nm, preferentially harvest bigger peptides, while smaller peptides are recovered more efficiently by the chips with smaller pores. The chips with 11.7 nm pores present no significant improvement in the LMW region detection (FIG. 26d). This result indicates the size limit of the MSC for an efficient enrichment strategy.

Example 3.4

Identification of the Selective Fractionation Patterns Due to MSC's Nanofeatures In the analysis of the fractionation and enrichment of LMW species from human serum, the chips were subdivided in 3 categories according to: 1) pore size; 2) wet ability; 3) pore geometry and surface morphology (Table 1). Unsupervised two-way hierarchical clustering was performed (two-dimensional complete linkage) to analyze the overall MALDI profiles of the different MSCs. (FIG. 10A). Depending on their harvesting characteristics, selective nanopore size and specific recovery patterns, each of the MSCs consistently identified unique proteomic signatures, as shown in the supervised hierarchical clustering (FIG. 10 B-D). The combinatorial MSCs device was designed and prototyped to perform high throughput fractionation on multiple and distinctive mesoporous selection domains. Using the combinatorial multi-chip strategy and combining the MS profiles obtained from just six different MSCs, a three fold increase in the number of detected peptides and proteins in the LMW range with respect to plain unprocessed serum was obtained (FIG. 10 E-I). These results showed that the different nanofeatures (structure, size and chemistry of the pores) on the MSCs conveyed different functionalities and served as analytical "first order processors" of this technology. According to this strategy, a multitude of chips can be used simultaneously to increase the amount of information recovered from the serum.

Example 3.5

Sample Stability and Reproducibility of the Harvesting Procedure

Reproducibility and reliability are crucial factors for any assay to be used in the clinical setting. Several publications reported that pre-analytical sample management might lead to significant alterations of the proteomic profiles and the generation of artifacts [29, 30]. The consistency of the on-chip fractionation assay was assessed, reproducing the same experiment in 6 replicates. After fractionation, the spectra of the replicates showed highly reproducible MS signals and consistent recovery. To evaluate protein stability, the MSCs were incubated with human serum, dried after washing, and stored for 3 weeks. The protein/peptide patterns obtained were comparable with those of freshly fractionated serum (FIG. 3 E), as confirmed by the results of the statistical analysis shown. The variability of the peak signals measured by the average Coefficient of Variation (CV) was estimated at 12.7% for crude serum and at 14.2% for the fractionated samples. The marginal variations could be due to the internal variability of the MALDI instrument and suggested that the on-chip pretreatment and storage did not induce any significant alteration of the MS protein profiles. In analogy with previously postulated mechanisms, it is hypothesized that the LMW species trapped inside the nanopores were preserved from degradation through the exclusion of proteases from the nanopores, or by steric inhibition of their proteolytic activity in the confined space of the nanopores (Luchini, A, Geho, D. H., Bishop, B., Tran, D. et al., Smart hydrogel particles: biomarker harvesting: one-step affinity purification, size exclusion, and protection against degradation. *Nano Lett.* 2008, 8, 350-361; Vaithesswaran, S., Thirumalai, D., Interactions between amino acid side chains in cylindrical hydrophobic nanopores with applications to peptide stability, *Proc. Natl. Acad. Sci.* 2008, 105, 17636-17641.)

The establishment of a simple sample acquisition and storage protocol, and the ability to impede further degradation of the proteins and peptides once they are captured, are essential for translation into the laboratory clinical practice (Banks, R. E., Stanley A. J., Cairns, D. A., Barrett, J. H. et al., Influences of blood sample processing on low-molecular weight proteome identified by surface-enhanced laser desorption/ionization mass spectrometry, *Clin. Chem.* 2005, 51, 1637-1649; Ransohoff, D. F., Lessons from controversy: ovarian cancer screening and serum proteomics. *J. Natl. Cancer Inst.* 2005, 97, 315-319.). With prior methodologies, deceptive results confounded the analysis and rendered meaningless the use of the profiles to derive any significant diagnostic or clinical information (Diamandis, E. P., Mass spectrometry as a diagnostic and a cancer biomarker discovery tool: opportunities and potential limitations, *Mol. Cell. Proteomics* 2004, 3, 367-378; Petricoin, E. F., Ardekani, A. M., Hitt, B. A., Levine, P. J. et al., Use of proteomic patterns in serum to identify ovarian cancer. *Lancet* 2002, 359, 572-577; Ransohoff 2005). On the contrary, after processing on the MSCs, the resulting protein patterns were reproducible and consistent even after a long term on-chip storage and regardless of the range of temperatures and environmental variables.

Example 3.6

The Effect of Pore Morphology on Proteome Recovery

Figures 1, 12A:
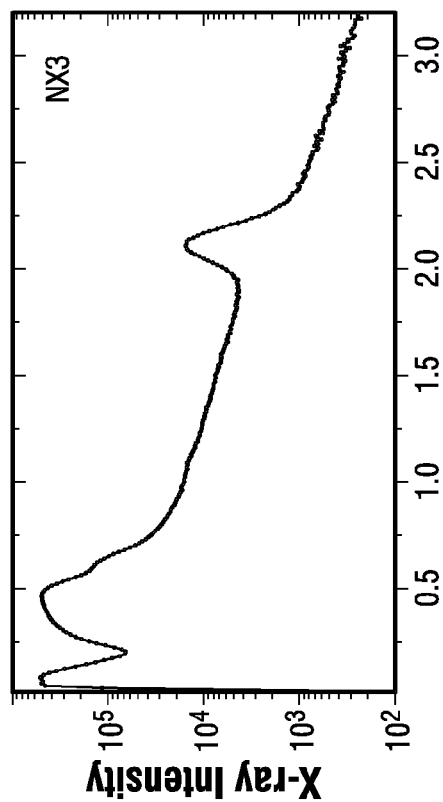
Figures 2, 12A:
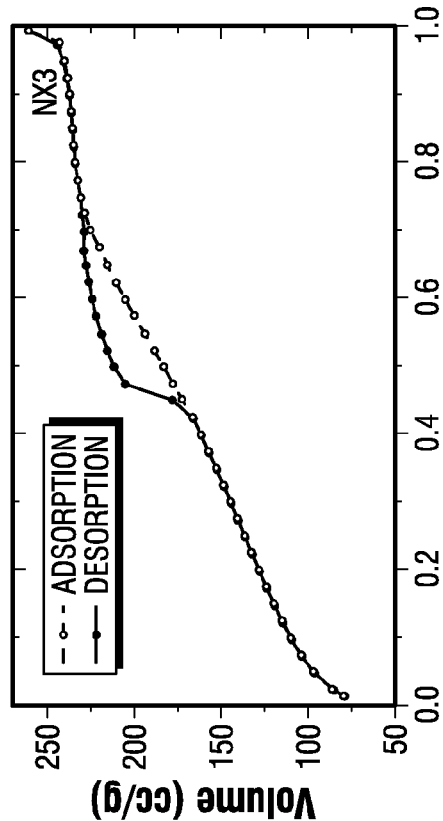
Figure 12B:
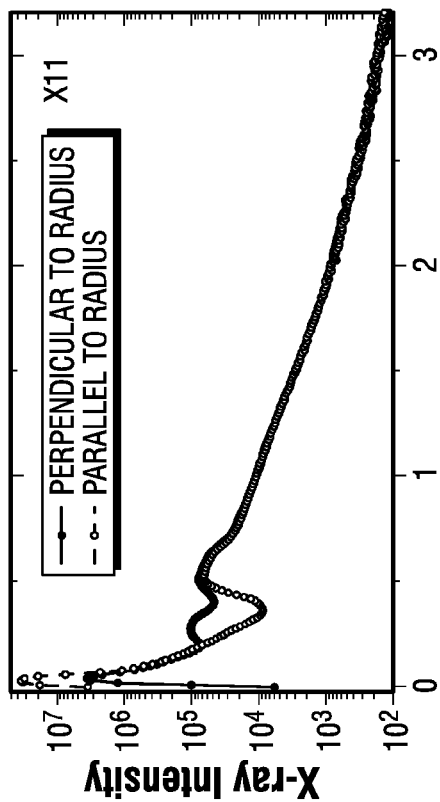
FIG. 12 shows the physical characterization of the MSC. Panel a shows $N_2$ adsorption-desorption isotherms of NX3 film; the inset shows the pore size distribution derived using BJH method. Panel b shows reflection SAXS patterns (in log scale) of NX3 film. Panels c and d shows TEM and STEM images of NX3 film respectively. Panel e shows reflection SAXS patterns (in log scale) of X11 film.
Figure 12E:
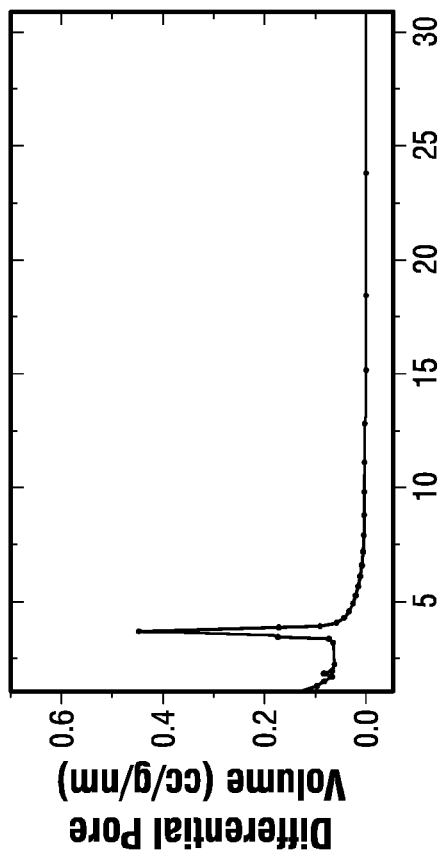
Figures 1, 27A:
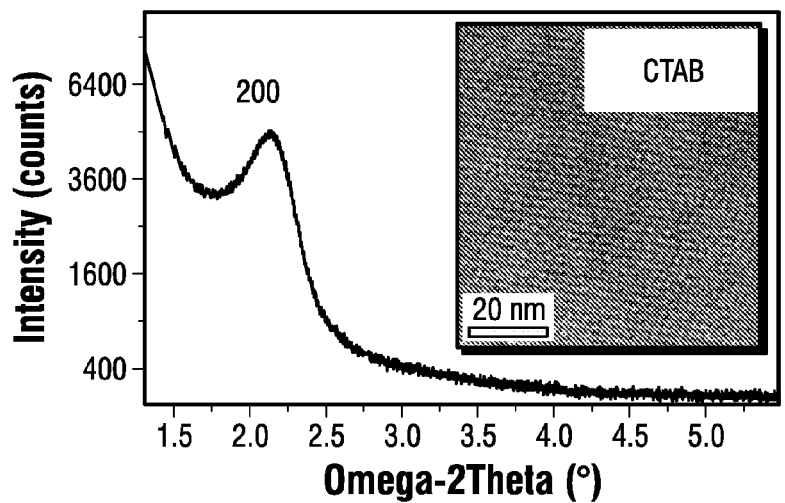
Figures 2, 27A:
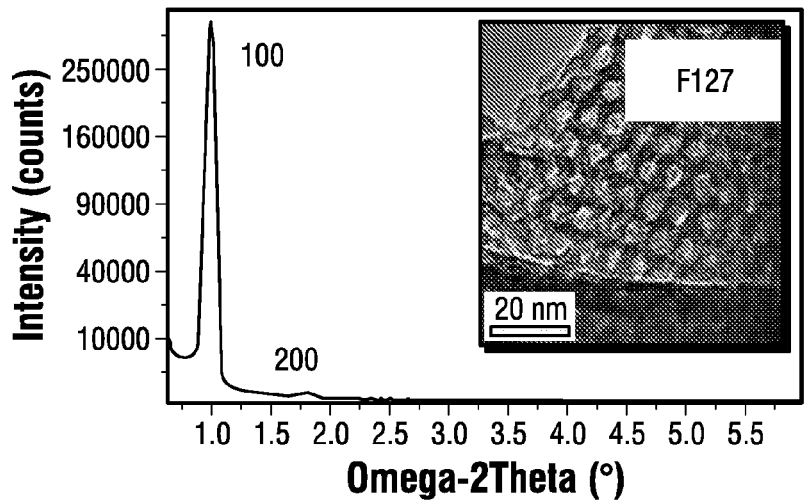
Figures 3, 27A:
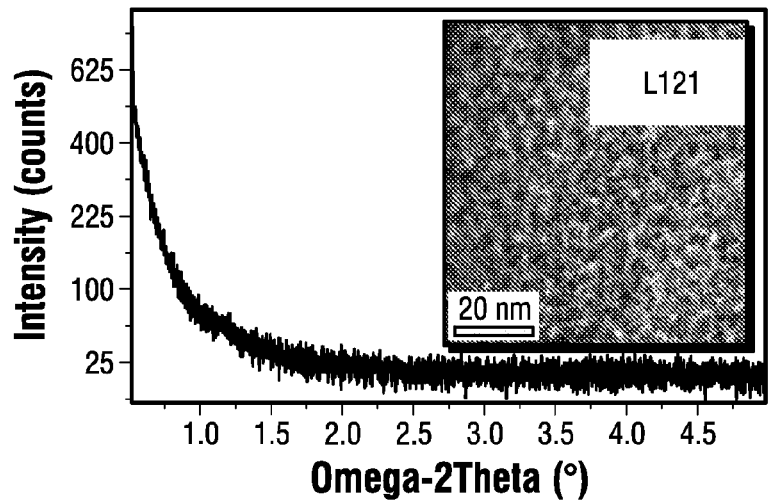

Besides the size dependant fractionation, the selective parsing of the enriched peptides into different subclasses according to their physicochemical properties would improve the efficiency of the on-chip strategy. Given the tunability of silica thin film material, the effect of pore morphology on proteome recovery was investigated. Starting with Pluronic F127 block copolymer, the periodic nanostructure of the pores can be transformed from a cubic to a hexagonal honeycomb like 3-dimensional (3D) architecture by tuning the molar ratio of silicate to polymer template. The average pore size remaining identical, the 2 different F127 MSC present a similar molecular cut-off (See FIG. 12a), which demonstrates the same size exclusion property. However, their harvesting capacity offers differential peptide enrichment. As shown in FIG. 27a, there is a significant increase of the capture of ACTH and Insulin peptides on the hexagonal surface while Substance P and a-Endorphin peptides are specifically recovered from the cubic MSC.

Figures 1, 27B:
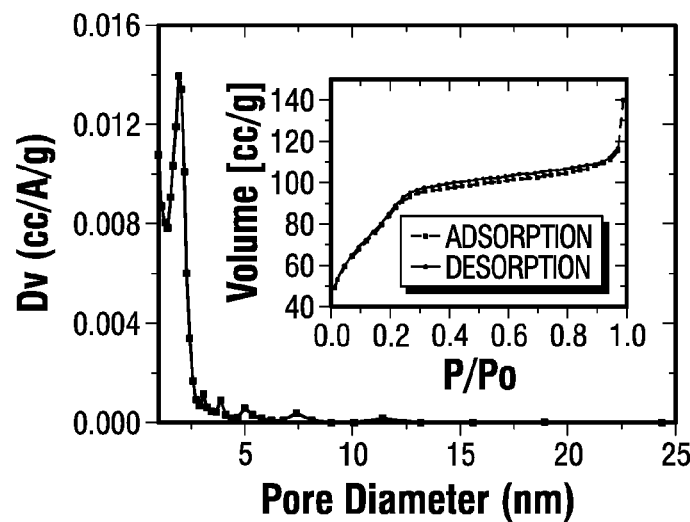
Figures 2, 27B:
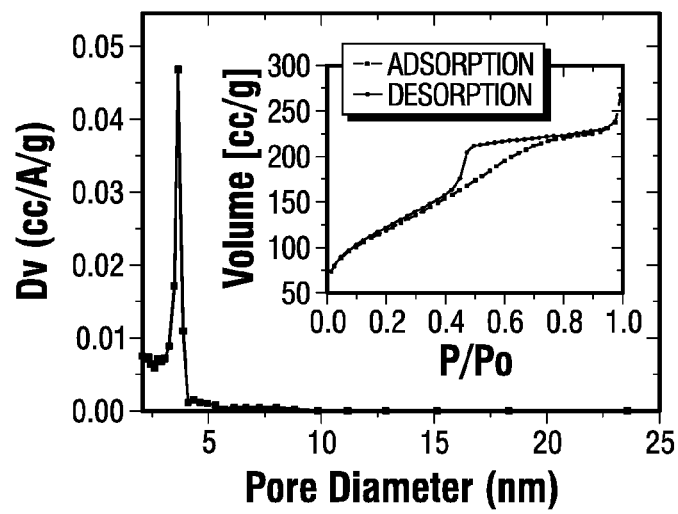
Figures 3, 27B:
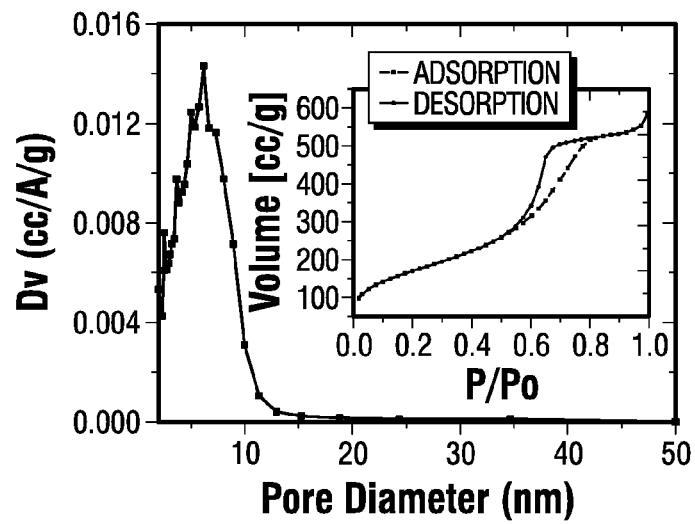
Figure 28A:
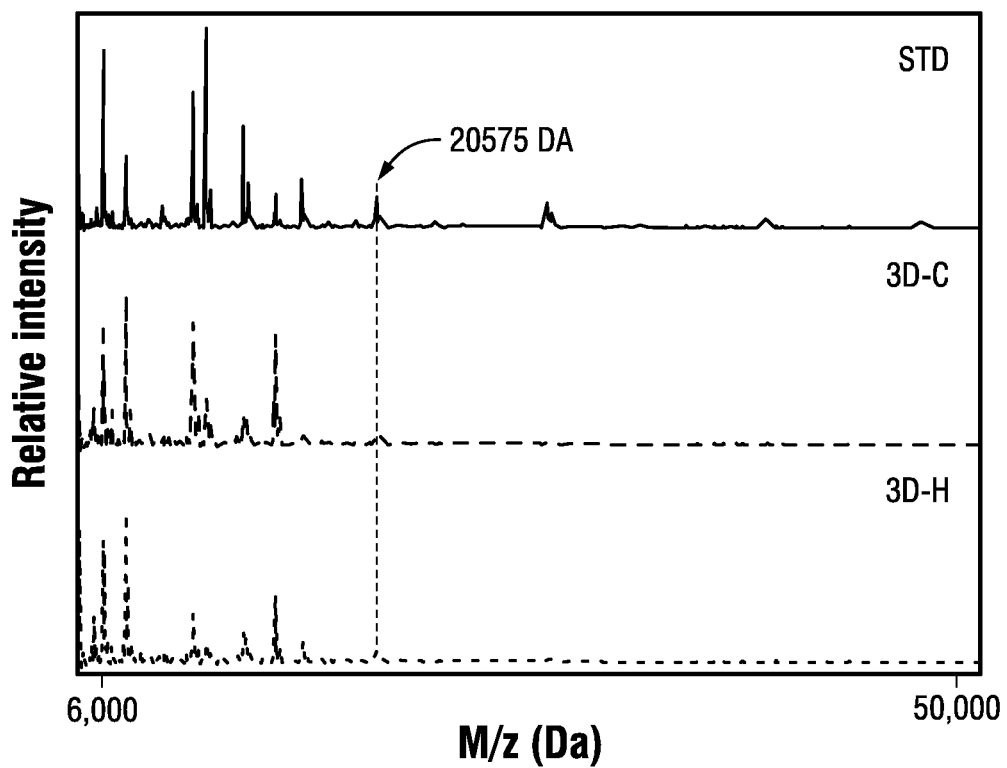
FIG. 28 shows the molecular cut-off of the modified MSC. Panel a shows pore structural transformation. The molecular cut-off for the 3.9 nm mesoporous thin films fabricated using F127 is similar (20575 Da) for both 3D cubic and 3D honeycomb hexagonal structures. Panel b shows the chemical functionalization. The molecular cut-off for the 6.2 nm mesoporous thin films fabricated using L121 is similar for both cationic (NH+) and anionic (SH−) surfaces.
Figure 28B:
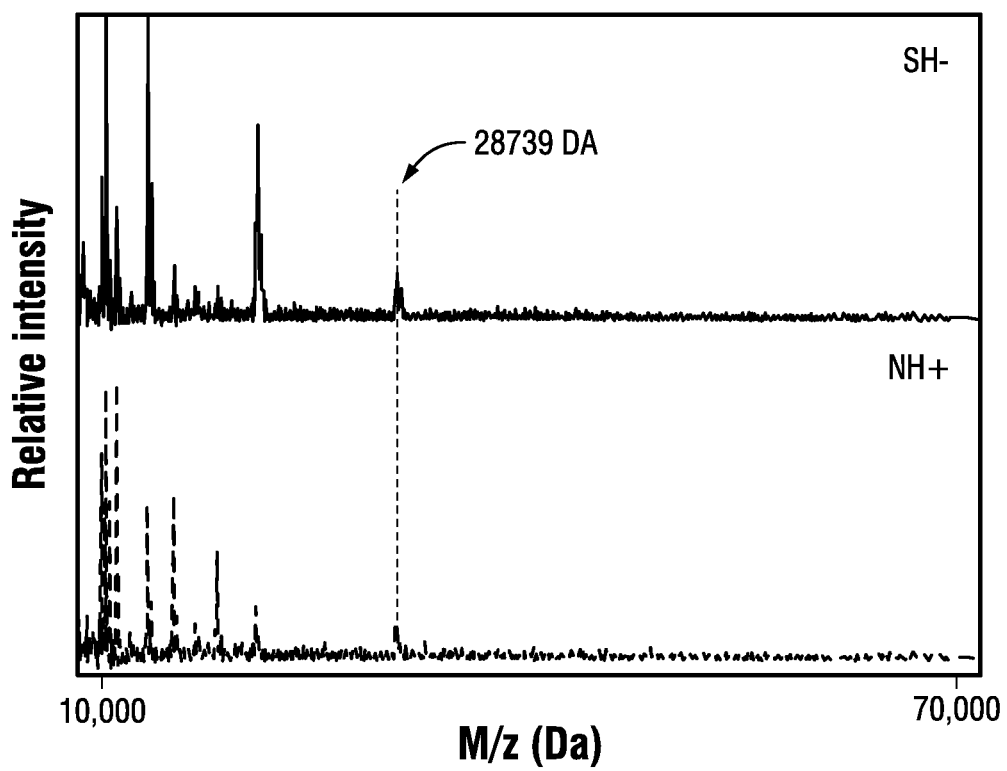

Another important factor to improve the enrichment capacity of the MSC is to resolve the complexity of biological samples in different sub-proteomes according to their chemical properties. MSCs conjugated with chemical functional groups on the pore surface have been developed. The chips have been modified using silane compounds with the functional groups aminopropyltriethoxysilane (APTES) for amine attachment, and mercaptopropyltriethoxysilane (MPTMS) for sulfhydryl attachment to provide cationic and anionic surfaces respectively. MS analysis of the proteomic standards solution fractionated on 6 nm MSC chips conjugated with the chemical functional groups is presented in FIG. 27b. According to their Isoelectric Point (IP), the positively charged and negatively charged LMW standards are captured on the anionic and the cationic chips respectively. HMW proteins remain excluded from the chips independently from their charge (See FIG. 28b). For example, Albumin has a net negative charge and remains excluded from the cationic chip. These results and the identical molecular cut-off offer displayed by the chips demonstrate the dual properties of the functionalized MSC (see FIG. 28): 1—the size dependant depletion of HMW proteins by the porous surface; 2—the specific enrichment of differentially charged LMW peptides.

Example 4

Example 4.1

Fabrication of Mesoporous Proteomic Chips with Different Physicochemical Property Mesoporous silica chips (MSCs) with different pore size were made by spin-coating a silicate sol-gel solution on a silicon wafer. The coating solution was a mixture of a tetra-ethyl-orthosilicate (TEOS) as silica source, solvent, water, acid, and surfactant polymer at designed ratio. The stock solution was prepared at first: 10 g of TEOS (Sigma Aldrich) was first added in a glass bottle, then, 8.5 g of absolute ethanol (Sigma Aldrich) was added, next, 1 g deionized (DI) water was added, and finally, 0.04 g of 0.07M HCl (Sigma Aldrich) solution was added. This mixture was stirred and heated to 60° C. for 90 minute. Then, the solution was cooled down, and aged at least two days before use. The coating solution was made by adding 8.7 g stock, 8 g ethanol, 0.6 g water, 1.0 g 0.07M HCl, and 1.8 g of triblock copolymer (Pluronic L31, L35, L64, or L121 triblock copolymer (BASF)) in this order. The mixture was vibrated on a Vortex mixer for 1 min and ultrasound for 5 min. The obtained clear solution was aged for 1 day before spin-coating. The film was made by spin-coating: 1.5 ml of coating solution was dispersed onto a 4" silicon wafer, and spun at 600 rpm for 5 s, and then the spinning speed was increased to 3000 rpm for 30 s. The coated wafer was placed in an oven, heated to 80° C., aged for 15 h. The temperature was then raised to 425° C. at a rate of 5° C./min. The wafer was kept at 425° C. for 4 h, and slowly cooled down to room temperature. Oxygen plasma treatment of the films was carried out in a Plasma Asher (March Plasma System). Coating of Hexamethyldisilazane (HMDS) was performed in a HMDS vapor prime oven (YES) at 150° C. for 5 min.

Example 4.2

Mask Machining and Prototype Device Integration

Figure 7I:
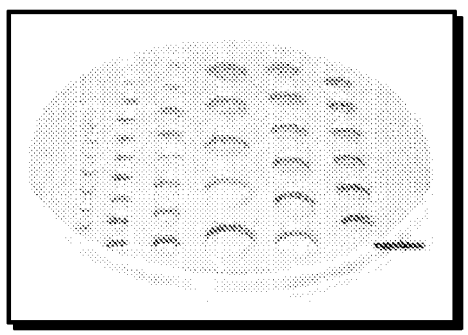
FIG. 7 shows the production and assembly of MSCs for proteomic applications. Panels a-h show the schematic evolution of the chemical composition of the coating solution during the production of a mesoporous silica film. Specifically, a: Fresh coating solution; b: Formation of micelles; c: Evaporation induced self assembly during spin-coating process; d: Zoomed in view of a pore after aging at elevated temperature. e: Bulk silicon wafer surface; f: Mesoporous silica film on a bulk silicon wafer; g: The silicone rubber mask was placed above the silica film; h: The final MSC. Panels i and j show cross-section views of the GX6 chip obtained by SEM and TEM imaging respectively (scale bar is 500 nm). Panels k, l, and m are photographs of MSCs with the silicone rubber mask; the area defined by the mask creates a "well like" structure defined by the thickness of the silicone rubber (l). Panels n and o show the front and back face of the prototype fractionation device assembled with 64 different types of MSCs (the scale bar in k-m is 10 mm).
Figure 7K:
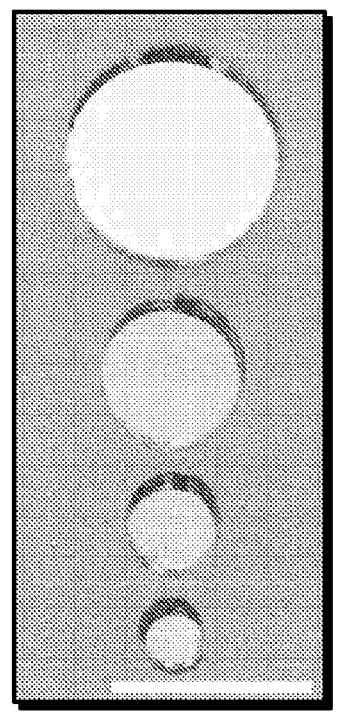
Figure 7J:
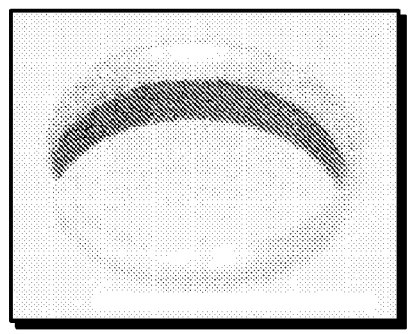
Figure 7L:
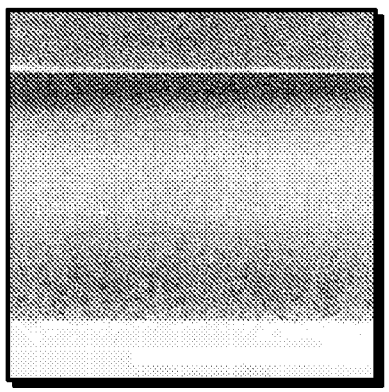
Figure 7M:
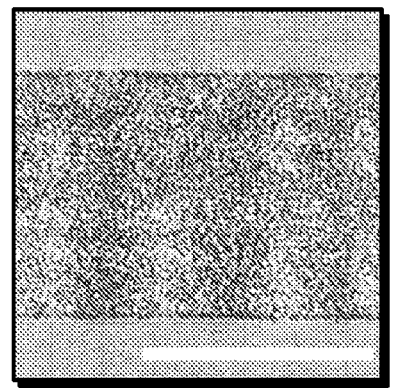
Figure 7N:
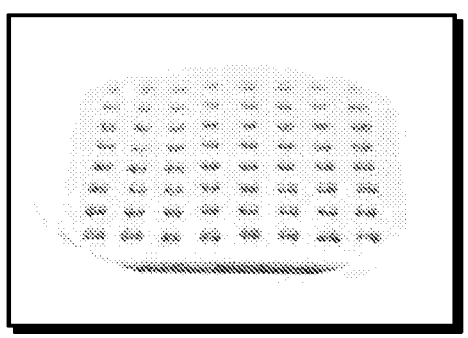
Figure 7O:
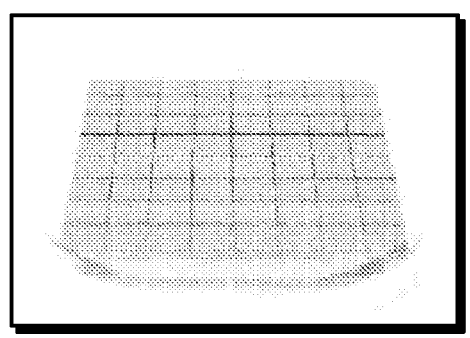
Figures 1, 9A:
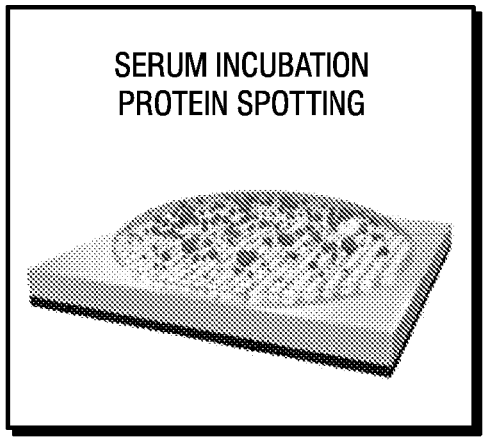
Figures 2, 9A:
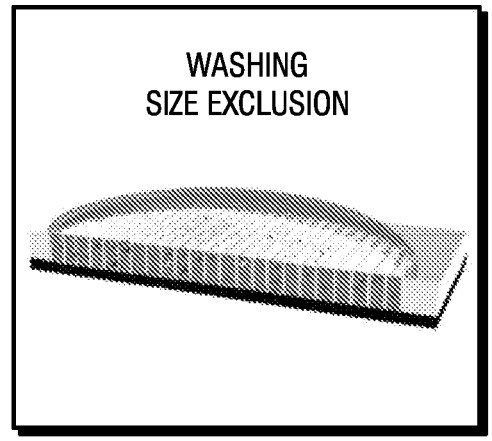

Silicone rubber masks were machined using 1.6 mm thick silicone rubber sheets (transparent, 40 DURO hardness, with adhesive layer from 3M) obtained from McMaster-Carr. The sheets were cleaned and cut to 100 mm×100 mm squares. A home-machined 8×8 hole punch matching 64 channel pipette was used to make the silicone rubber mask. The MSCs were diced into 9×9 mm squares. 64 squares from different MSCs were attached on a 100 mm glass wafer, and then the silicone rubber mask was aligned and assembled on top of the MSC squares. FIG. 1 illustrates the schematics of the chemical composition of the coating solution during the production of the mesoporous films (FIG. 7a-d) and the assembly of the final chips (FIG. 7e-h). Manufacturing protocols were optimized in order to obtain MSCs with smooth, crack-free surfaces across 4" silicon wafers (FIG. 7i-j, k-o). Three different masks with defined rounded areas of different diameters were designed to optimize proteomic sampling.

Example 4.3

Characterization

The thickness and porosity of obtained films were determined by a M200-DI variable angle spectroscopic ellipsometer (J. A. Woollam Co. M-2000DI). Ellipsometric values, $\Delta$ and $\psi$ were measured from wavelength range 300-1000 nm at three incidence angles, 55°, 60°, 65°, respectively, and fitted using the Effective Medium Approximation (EMA) model with WVASE32 software. The surface area and pore size of the mesoporous films were measured using $N_2$ adsorption-desorption isotherm on a Quantachrome Autosorb-3B Surface Analyzer. All the samples for $N_2$ adsorption-desorption experiments were prepared by scraping 10 pieces of 4" spin-coated thin silica films. The sample was degassed at 300° C. for over 12 hours, and the $N_2$ adsorption-desorption isotherm was measured at −196° C. over relative $P/P_o$ pressures range 0.015-0.995. The Brunauer-Emmett-Teller (BET) surface areas were determined over a relative pressure range of 0.05 to 0.3. Nanopore size distributions were calculated from the adsorption branch of the isotherms using BJH model. Ultrathin section TEM samples were prepared as described in Supplemental Materials. Transmission Electron Micrographs of the sections were obtained in a 200 kV FEI™ TECNAI™ G2 F20 X-TWIN TEM. Small angle X-ray scattering spectra (SAXS) were obtained on a Rigaku Smartlab horizontal sample mount XRD system with Cu K$\alpha$ ray. $\theta$-2$\theta$ scans were recorded over the angle range 0° to 5°. Contact angles of film surface were measured by a goniometer with captive bubble contact angle measurement.

Figure 8A:
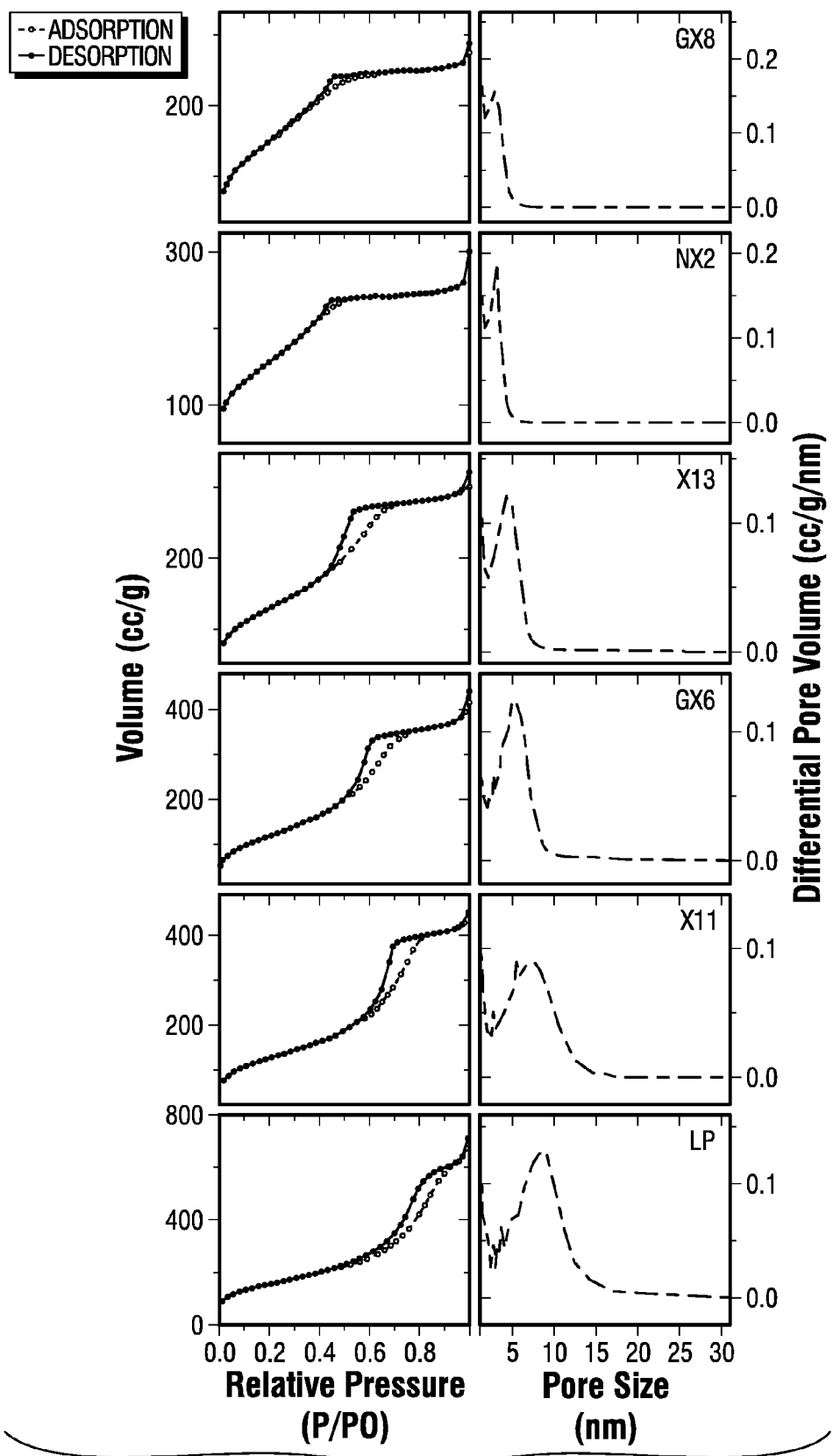
FIG. 8 shows the physical characterization of selected MSCs. Panel a, left side: N2 adsorption-desorption isotherms. Panel a, right side: pore size distribution curve. Panel b shows the reflection SAXS patterns for selected MSCs; Panel c shows a representative AFM image of the X11 chip structure.
Figure 8B:
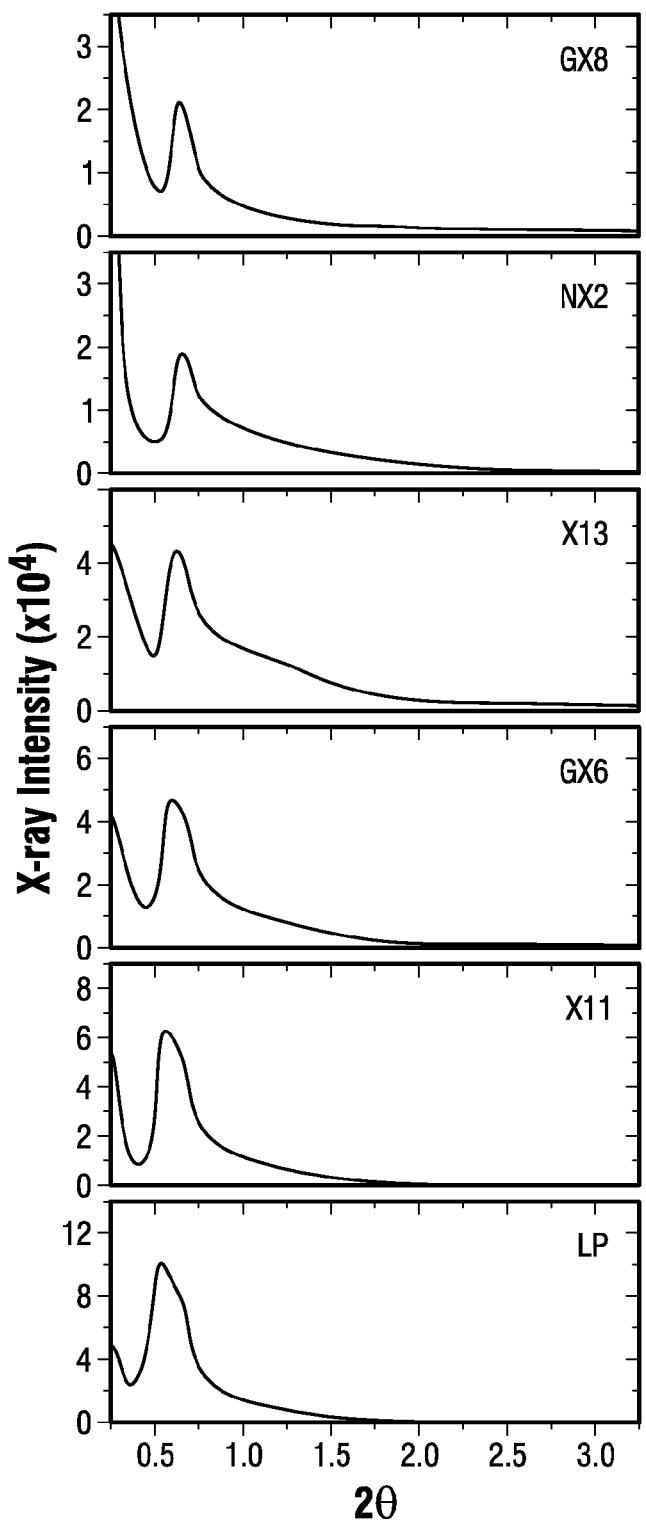
Figure 12C:
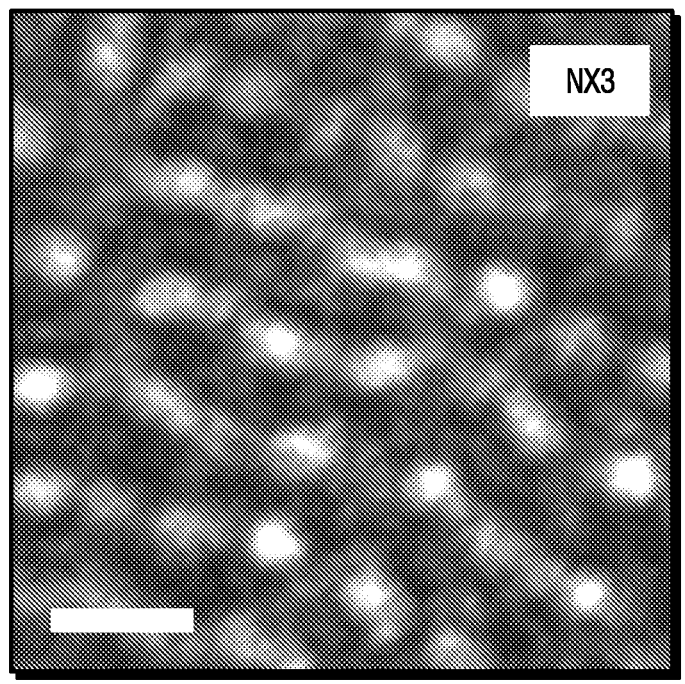
Figure 12D:
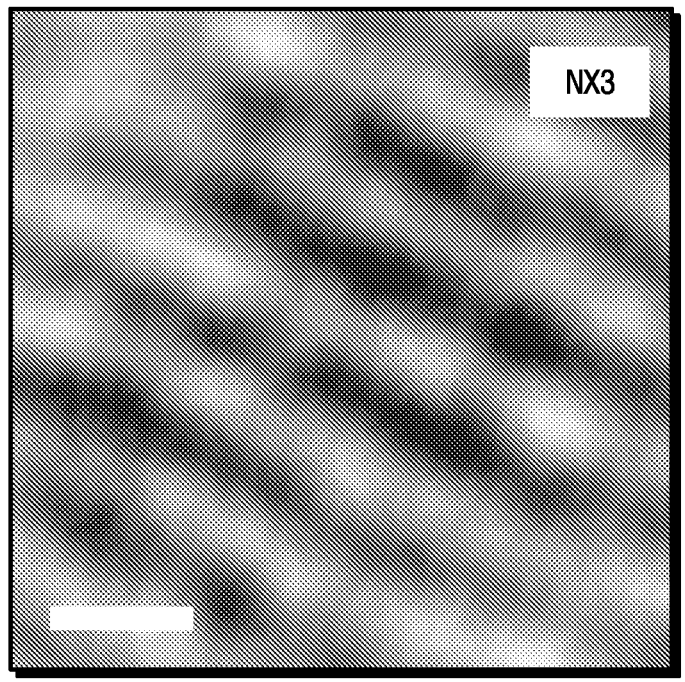
Figure 13A:
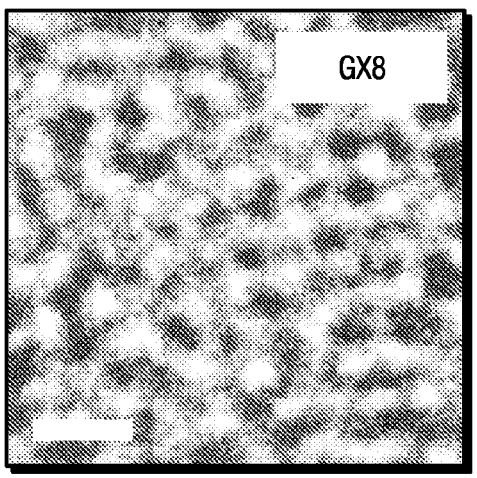
FIG. 13 shows the TEM imaging of MSC's surface, and specifically TEM images of 6 selected MSCs. Note that the pore size is increasingly larger from sample GX8 (2.7 nm) to X12 (8.9 nm). The scale bar is 10 nm.
Figure 13B:
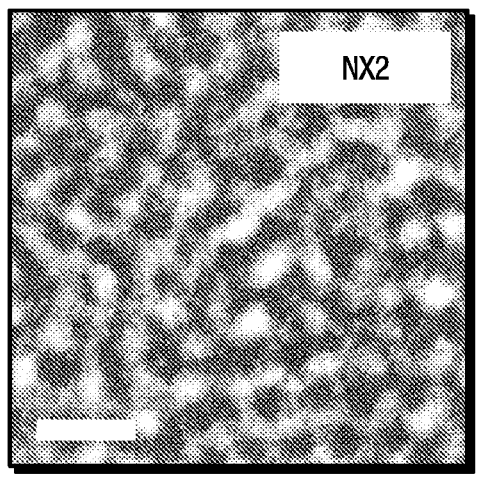
Figure 13C:
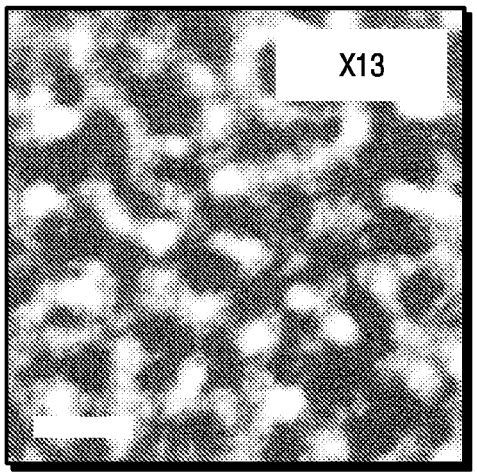
Figure 13D:
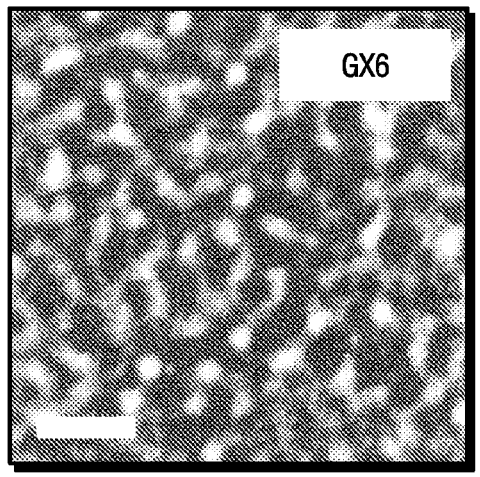
Figure 13E:
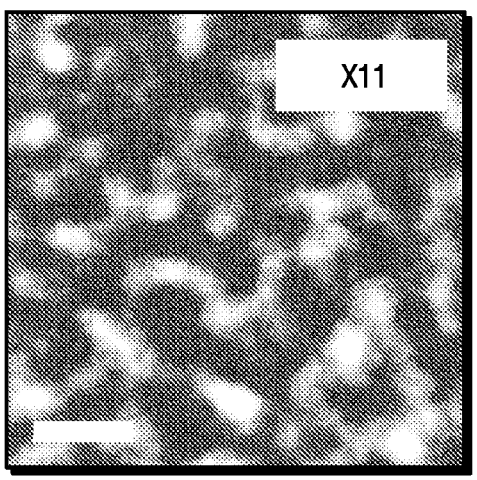
Figure 13F:
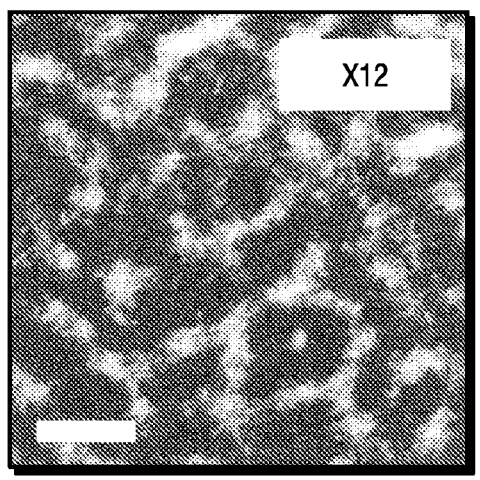
Figure 14A:
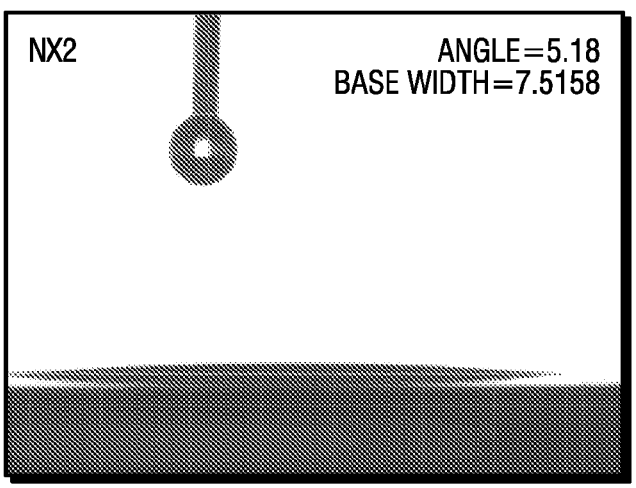
FIG. 14 shows the measurement of surface hydrophobicity and hydrophilicity of MSCs. Optical images of 3 representatives contact-angle measurements. The contact angle increases with hydrophobicity.
Figure 14B:
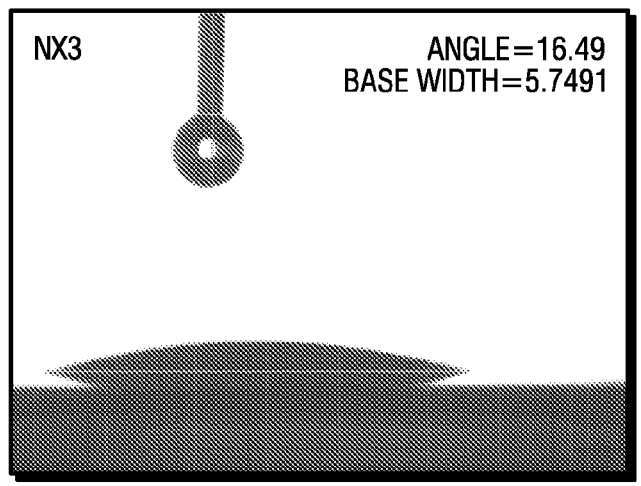
Figure 14C:
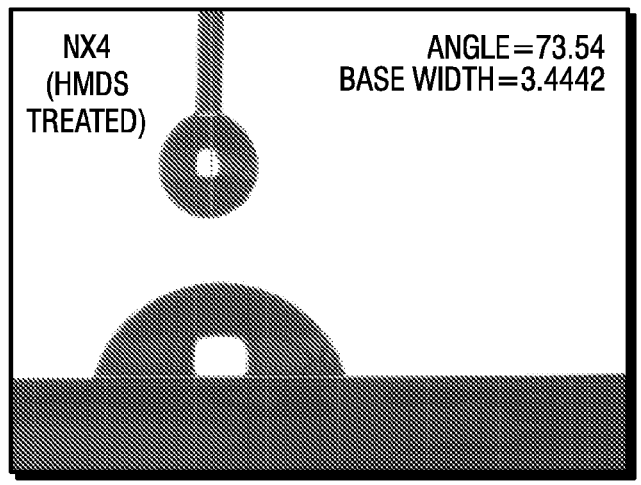
Figure 15:
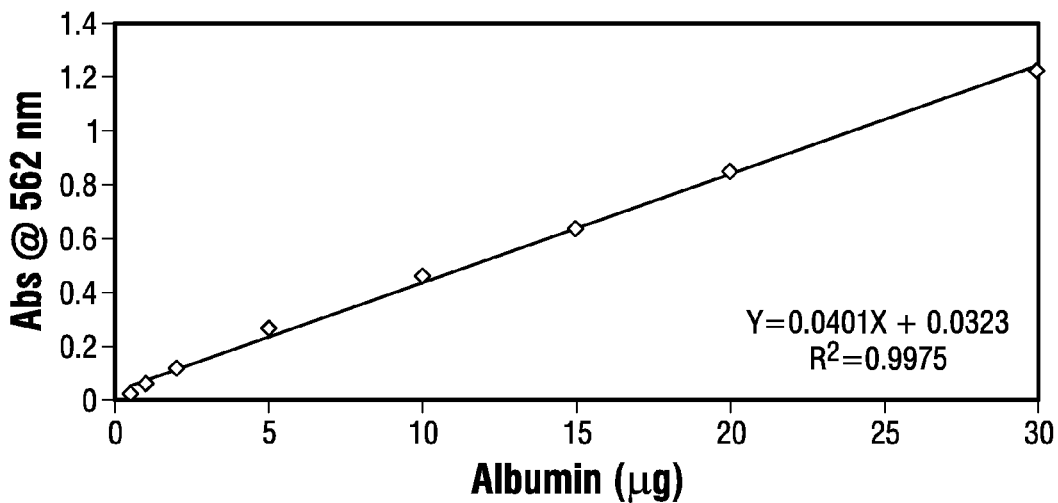
FIG. 15 shows a standardization curve. Specifically, a representative standardization curve is shown made according with the instructions provided by the microBCA protein assay kit. The graph shows the regression curve that fits the experimental results, its formula and its coefficient of determination ($R^2$). The equation was used to convert the experimental data obtained through Spectrophotometer reading of sample absorbance at 562 nm to the corresponding protein amount in μg.

The porosity of the selected MSCs ranged from 40% to 70%, the pore volume in a circular area of 6 mm in diameter from 6.0 to 12.3 nl as obtained from ellipsometry measurement. The $N_2$ adsorption-desorption isotherms of six selected MSCs are shown in FIG. 8a. The isotherms can be classified as Type-IV curve with H2 hysteresis loops, according to the standard of the International Union of Pure and Applied Chemistry. This type of hysteresis indicated ink-bottle shaped pores, and non-ordered worm-like pore arrangement. For this type of isotherm, adsorption branch of the isotherm can be used to calculate the pore size distribution. The pore size distribution curves of six MSCs with worm-like inter-connected pore structure (for easy pore accessibility) were derived from adsorption isotherms using Barrett-Joyner-Halenda (BJH) method and are shown in FIG. 8a (average sizes ranging from 2.7 nm to 8.9 nm). The reflection Small Angle X-ray Scattering (SAXS) curves of the films are shown in FIG. 8b. The curves were recorded 2 cm off the center of the 4" wafer, with the beam incidence along the direction of radius. The SAXS curve showed a peak around 0.5°-0.7° (corresponding to d-space around 13-17 nm) suggesting a periodic spatial variation of the electron density in the film, and some degree of alignment of the pores. The pore alignment was induced by strain during the spin-coating process. By comparing the SAXS curves at $\phi=90°$ and $\phi=0°$ (see FIG. 12), a differential pore alignment along and perpendicular to the radius of the wafer was discovered. This was further confirmed by AFM measurement of the film surface by showing different dimensions of the features along and perpendicular to the radius (FIG. 12c) and by TEM imaging (see FIG. 13). Different chemical modifications were also studied. Oxygen plasma treatment was applied to ensure the hydrophilicity, while HMDS coating was applied to make the surface hydrophobic. The hydrophilicity of the films was evaluated through contact angle measurement (see FIG. 14). Films treated with $O_2$ plasma showed <15° contact angle, while HMDS coated films showed >65° contact angle.

Example 4.4

Protein Fractionation

Figure 3A:
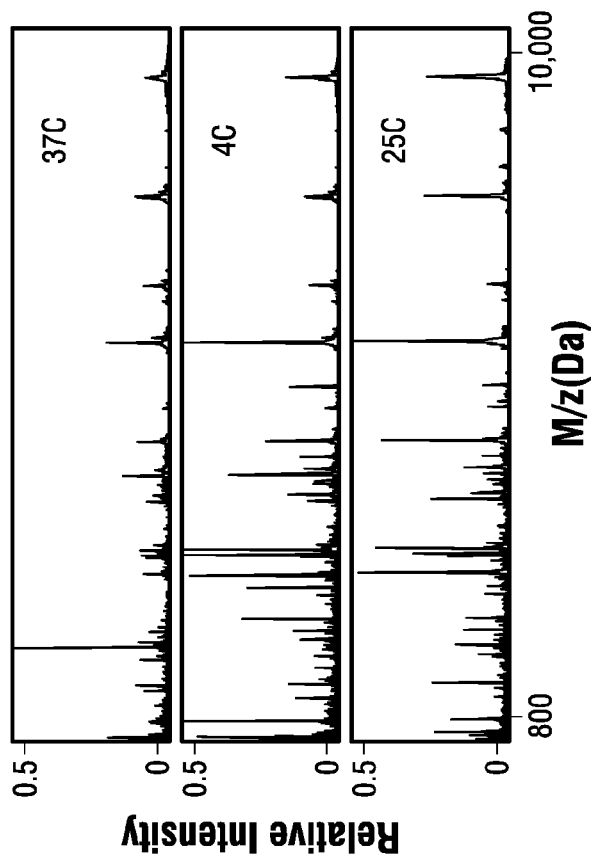
FIG. 3 shows the reproducibility and on-chip stability of fractionated serum. Panel a shows MALDI profiles of fractionated serum on X10 chips, which illustrate the increase of LMW peptides and proteins detection when the serum is processed at 25° C. compared to 4° C. and 37° C. Panels b, c, and d show the linear regression analysis of the average intensities of detected MS peak for each temperature. The comparison was plotted on a log-log scale to create a scatterplot. Panel e shows the representative MALDI profiles of LMW peptides and proteins eluted immediately after serum fractionation or after 3 week on-chip storage at room temperature. Panels f-h show the linear regression analysis of average intensities of detected MS peak in each replicate compared to replicate 1 for crude, fractionated serum and fractionated serum after 3 week storage at room temperature, respectively (the coefficient of variation (CV) and the coefficient of determination ($R^2$) are indicated in the insets).
Figure 3C:
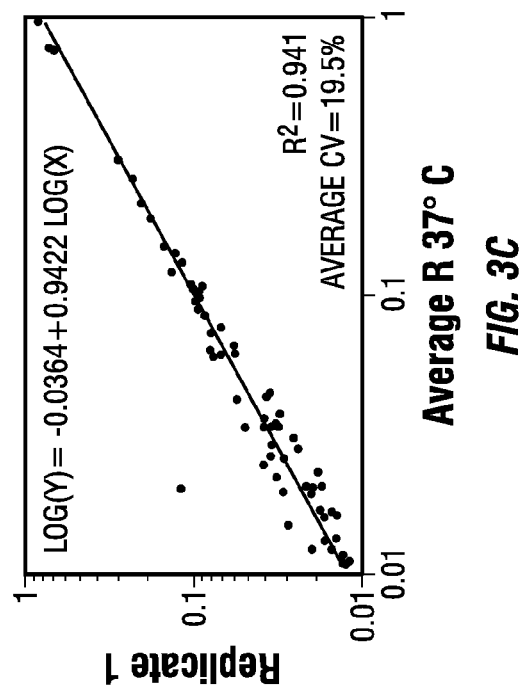
Figure 3B:
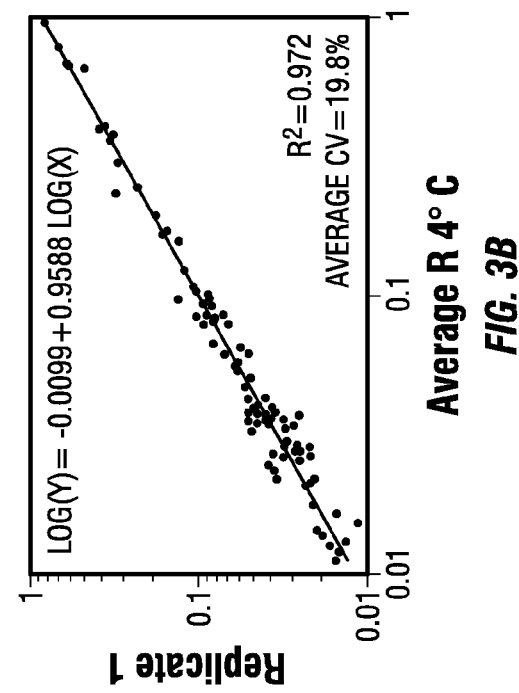
Figure 3D:
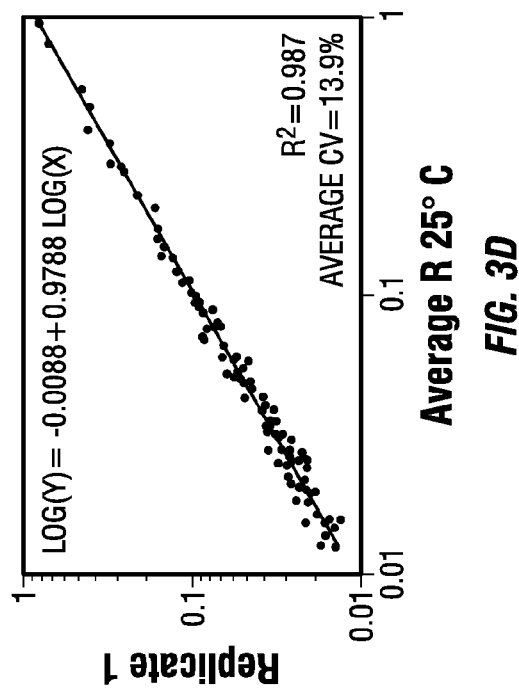
Figure 3G:
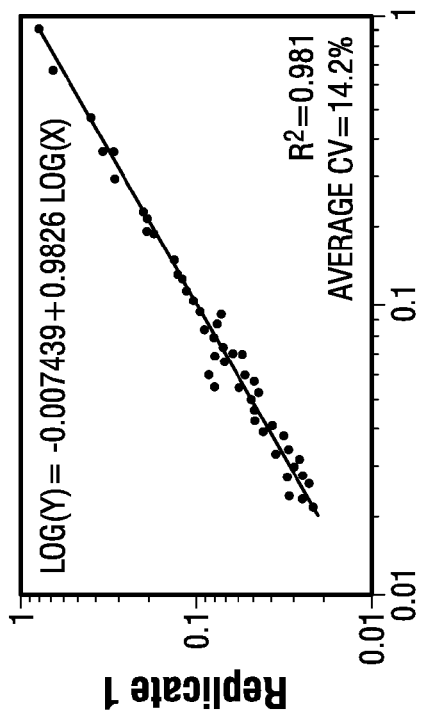
Figure 3H:
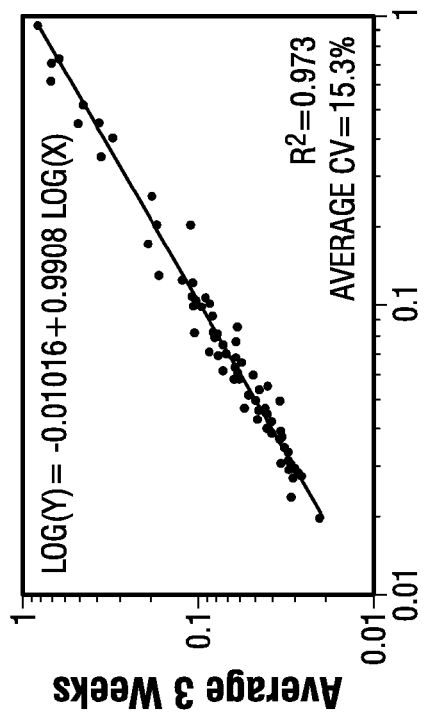
Figure 3E:
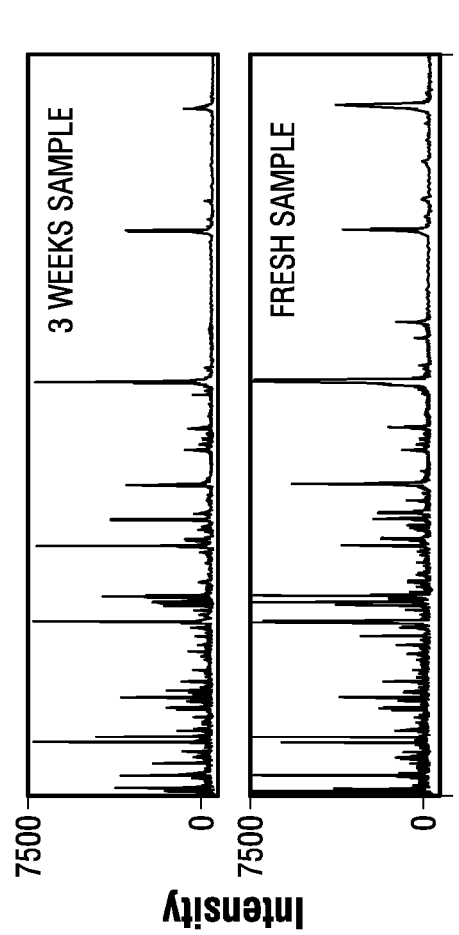
Figure 3F:
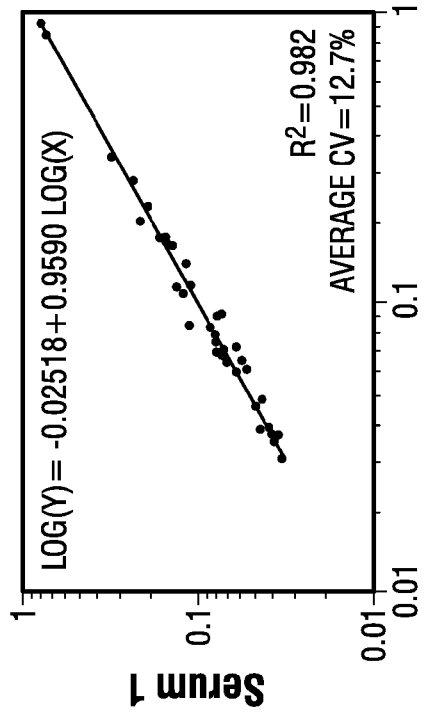
Figure 16A:
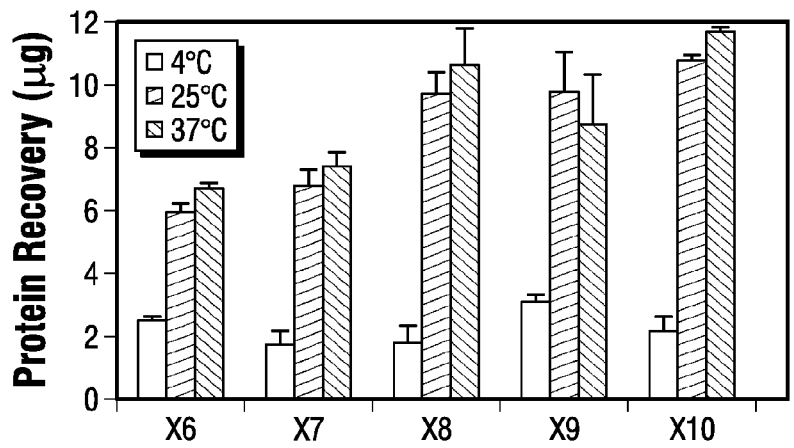
FIG. 16 shows the effect of temperature on protein fractionation. Panel a shows the effect of incubation temperature on protein recovery from multiple chips. A set of 5 chips with different physical properties were tested at 4° C., 25° C. and 37° C. In all cases, the amount of protein recovered was significantly higher at 25° C. and 37° C. than at 4° C. Panel b shows the effect of incubation temperature on the amount of protein retained by the chip surface. The amount of protein removed through the washing steps was low at 4° C., compared to 25° C. and 37° C. The graph in panel b shows representative results obtained using chip X9. Similar results were obtained with all the other chips tested (X6, X7, X8, X10).
Figure 16B:
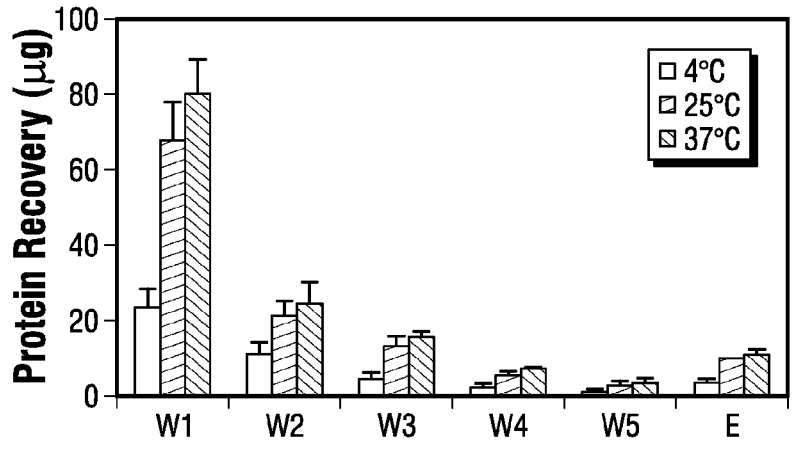
Figure 17A:
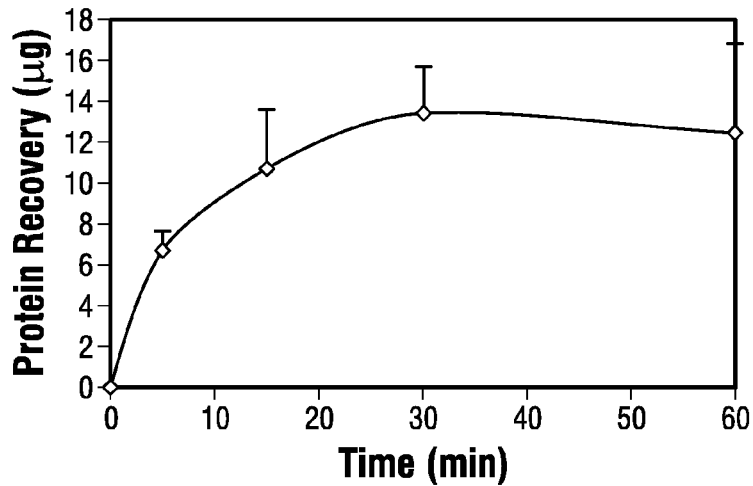
FIG. 17 shows the effect of incubation time on protein fractionation. Panel a shows the total protein recovery after fractionation performed at different incubation times. Panel b shows a histogram comparing the amount of protein removed during the washing steps. In the first wash, the amount of protein positively correlated with incubation time. Mean values and standard deviations of 3 independent experiments are shown. Panel c shows the comparison of protein recovery in the last 2 washing steps and in the final elution. In all conditions tested, the amount of eluted protein is significantly higher than the amount of protein removed from the surface during the last 2 washings.
Figure 17B:
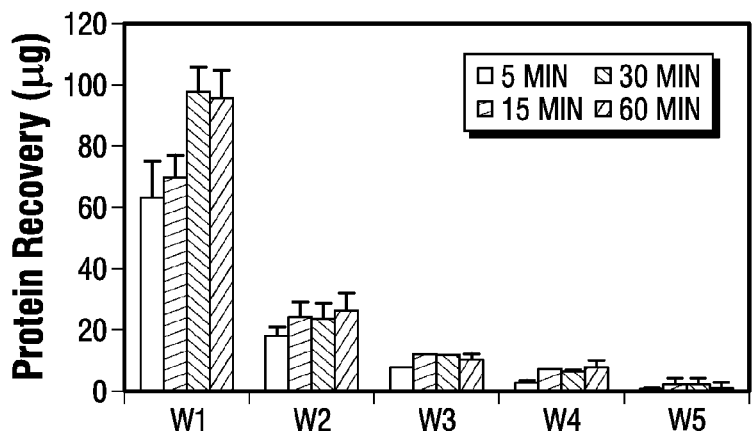
Figure 17C:
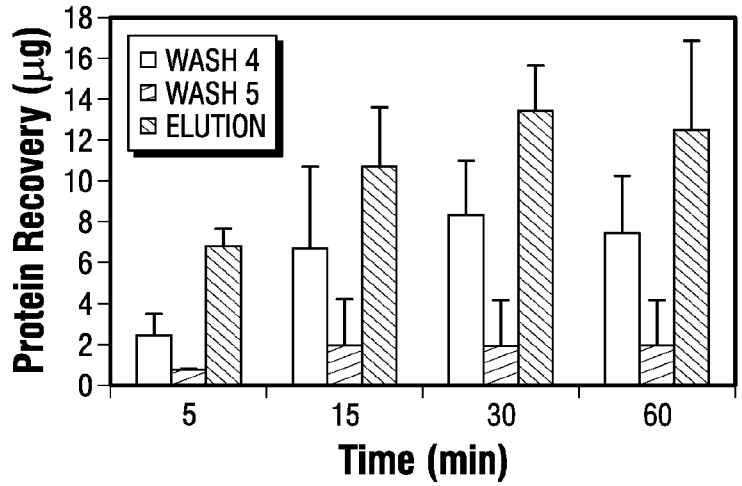
Figure 18A:
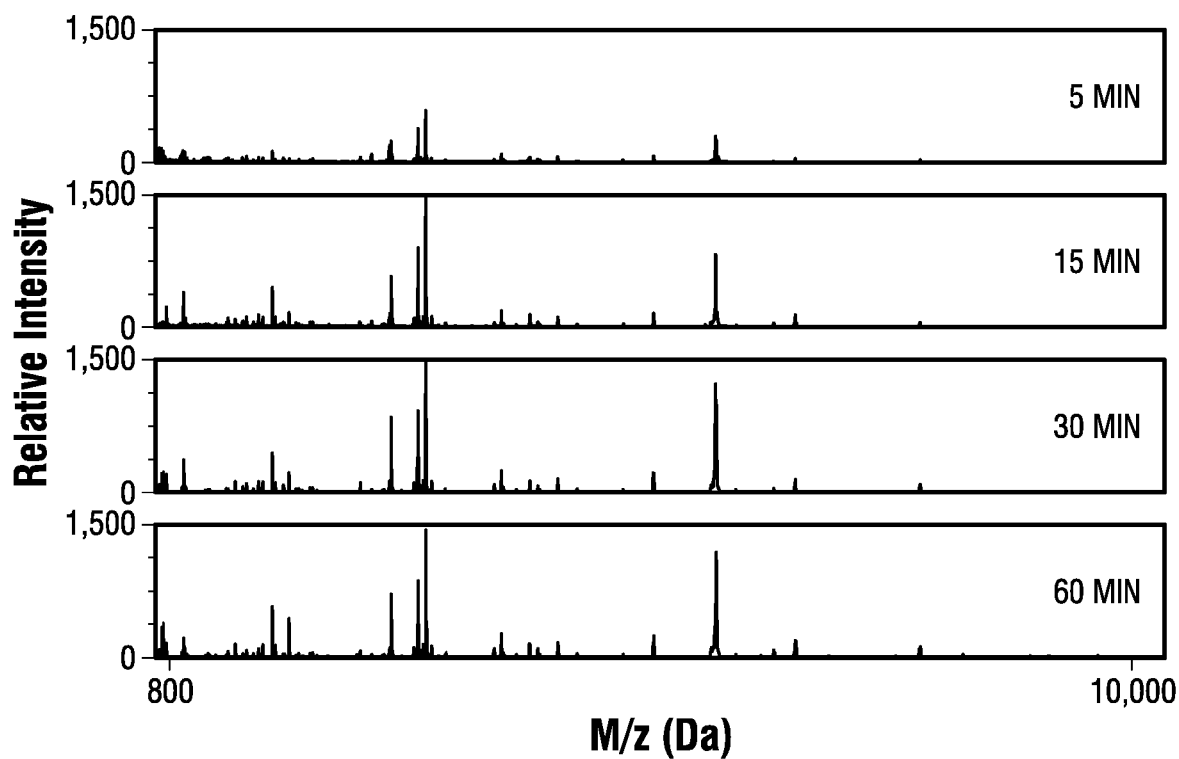
FIG. 18 shows the MALDI spectra obtained after different incubation times. Panel a shows MALDI profiles of fractionated serum on X10 chip at different incubation time (5 min, 15 min, 30 min, and 60 min). The intensity of peaks detection is markedly lower for the min incubation. The profiles for 15 min, 30 min, and 60 min are similar. Panel b shows the linear regression analysis of the triplicate average intensities of detected MS peak compared to replicate 1 for each incubation time. The comparison was plotted on a log-log scale to create a scatter-plot.
Figure 18B:
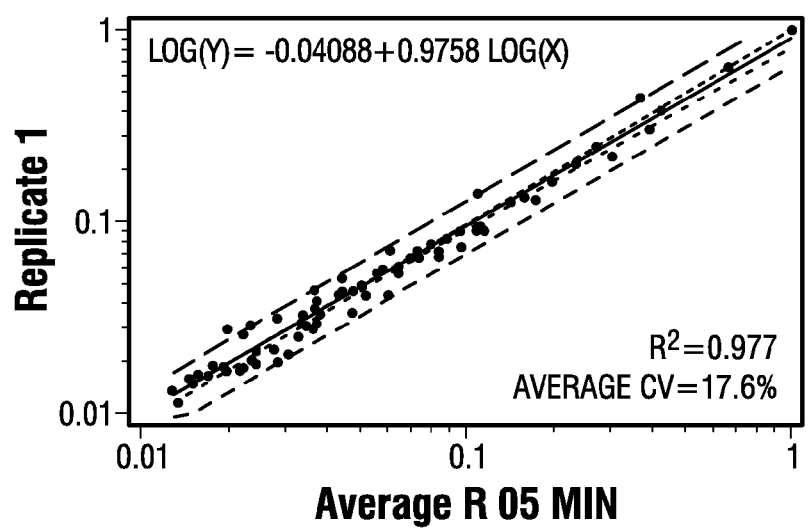
Figure 18C:
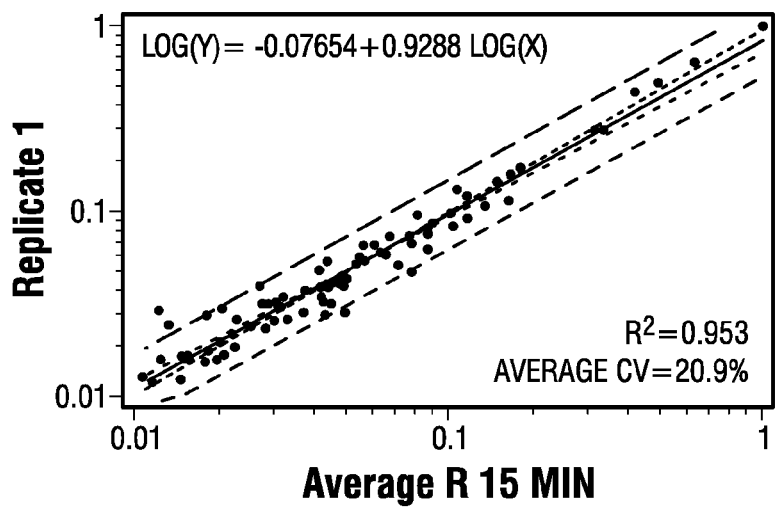
Figure 18D:
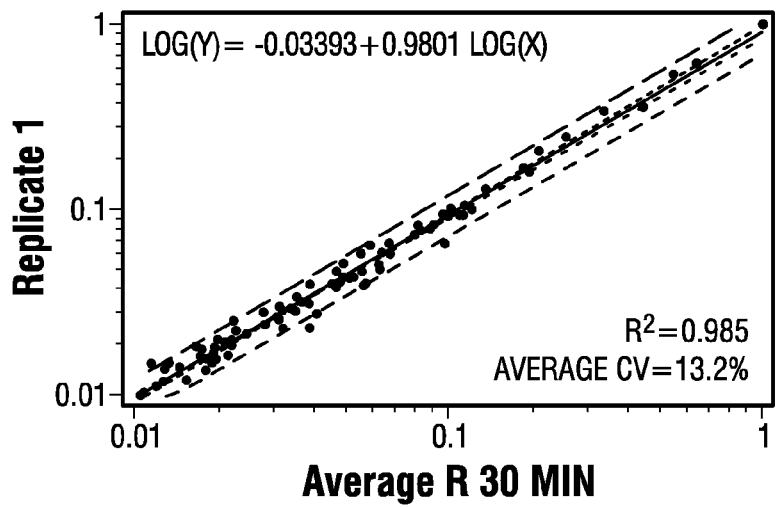
Figure 18E:
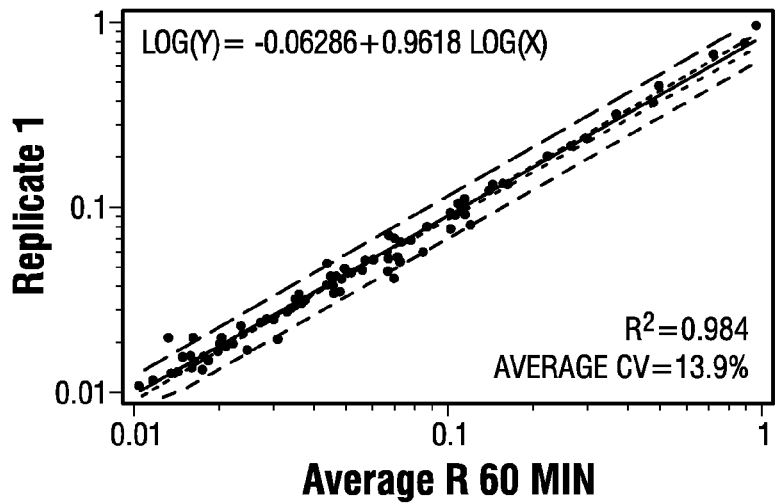
Figure 19A:
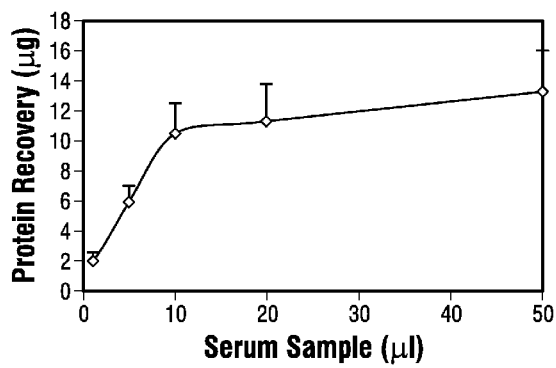
FIG. 19 shows the effect of sample volume on protein fractionation. Panel a shows the protein recovery from fractionation experiments performed using different amount of serum on the same chip type. The amount of protein recovered is very low when only 1 and 5 µA of serum are used. Protein recovery reaches a plateau when 10 µA of serum are used. The incubation of 20 and 50 µl of serum did not result in a higher protein recovery. Panel b shows that the amount of protein in the washing samples increases with the increase of the serum used for fractionation.
Figure 19B:
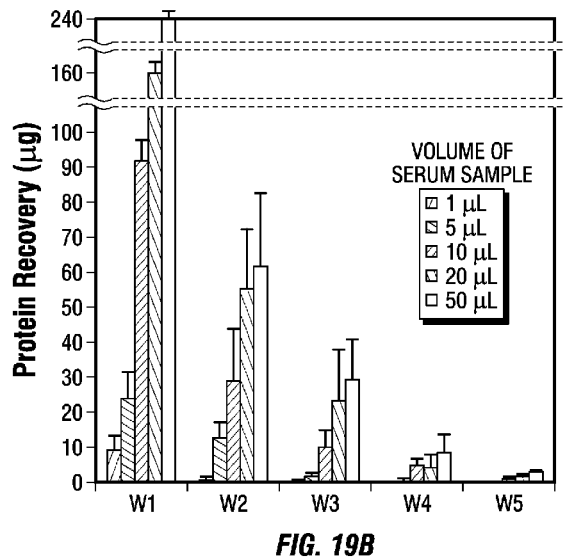
Figure 20:
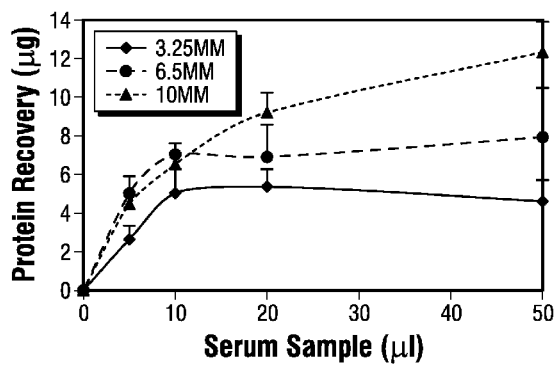
FIG. 20 shows the effect of surface area on protein fractionation, specifically, the protein recovery from 12 independent experiments performed with increasing amount of serum samples (5, 10, 20 and 50 µl) on different nanoporous surface areas (diameters equal to 3.25, 6.5 and 10 mm; same chip type) using the same settings (temperature, time, washings).

The MSCs were employed for protein fractionation and enrichment of the LMW species using a fast three step on-chip fractionation strategy, as shown in FIG. 3a. The effect of temperature (See FIG. 16), incubation time (See FIGS. 17 and 18), sample volume (See FIG. 19), surface area (See FIG. 20), and pore volume (See FIG. 22) on protein recovery was studied, and the most stable, effective and reproducible protocol for protein fractionation was established.

More specifically, in order to identify the best working condition, and understand the effect of temperature on protein recovery, fractionation experiments were performed at 4° C., 25° C. and 37° C. The results are shown FIG. 16 and clearly indicate that recovery was very low at 4° C. A tentative explanations is that the mechanisms of diffusion into the nanopores were slowed down at that temperature and so the molecular interactions between the proteins and the silica surface. Conversely, protein recovery at 25° C. and 37° C. was not significantly different. 25° C. was chosen as the optimal temperature and all subsequent experiments were performed at room temperature (RT). This decision was also justified by the fact that degradation processes such as proteolytic or enzymatic digestion might take place at a higher pace at 37°

C. This decision was also justified by the fact that degradation processes such as proteolytic or enzymatic digestion might take place at a higher degree at 37° C.

The influence of incubation time on protein recovery was also studied. By running the experiment at RT with a fixed volumes of serum, it was determined that protein recovery reached a plateau after 30 minutes of incubation (See FIG. 17a). Further incubation time did not increase the amount of protein recovered while it might have increased the chances to have protein degradation on the chips.

Interestingly, also the amount of protein sticking to the surface of the chip and removed during the washing steps was higher when the temperature was higher and the incubation time longer and the serum sample larger (See FIGS. 17-20).

The effect of the amount of serum used on protein recovery was also studied. By analyzing the data summarized in FIG. 19, it was concluded that, regardless of the volume of serum (1, 5, 10, 20, 50 µl) spotted onto the nanoporous silica chips, the amount of recovered protein was nearly the same, with the only statistically significant exceptions of the 1 and 5 µl experimental points which resulted in a reduced protein recovery. Protein recovery reached a plateau when 10 µl of serum were used. The incubation of 20 and 50 µl of serum did not result in a higher protein recovery. In all conditions tested and in accordance with our previous results, the protein amount in washes number 4 and 5 was lower than the amount of protein recovered in the elution steps (See FIG. 17c).

In a set of 12 independent experiments, various amounts of serum sample (5, 10, and 50 µl, brought to the same final volume of 50 µl by adding deionized sterile water) were applied on different nanoporous surface areas (diameters equal to 3.25, 6.5 and 10 mm; same chip type, see FIG. 7 j,l,n) using the same settings (temperature, time, washings). Protein recovery from the smallest area (3.25 mm) is significantly lower than that obtained from the intermediate and larger areas (See FIG. 20). Independently from the amount of serum used, protein recovery reached a plateau on 6.5 mm diameter nanoporous surfaces when 10 µl of serum were used. When a larger fractionating area was used (10 mm diameter), protein recovery progressively increased with the amount of serum spotted on the surface.

Figure 22A:
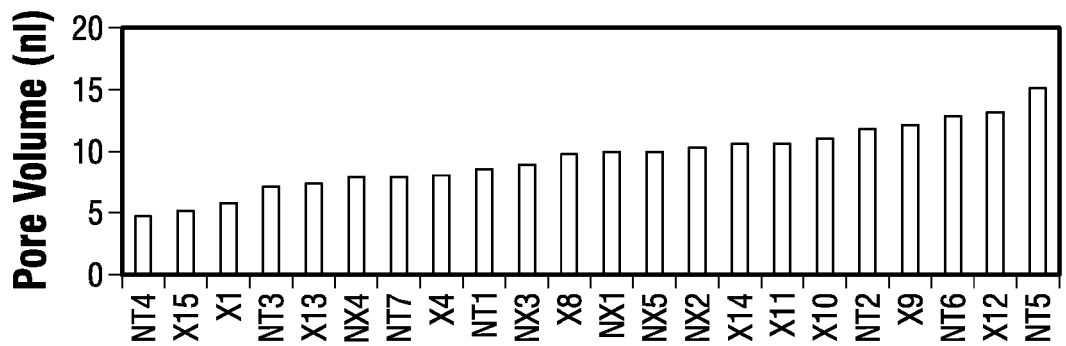
FIG. 22 shows the effect of pore volume on protein fractionation. Panel a shows the characteristic pore volume of 22 chips, which was calculated considering the diameter of the surface used for the fractionation, the thickness of the chip and its porosity. Panel b shows the amount of protein recovered from each of the chips using the same experimental settings. Panel c shows that protein recovery and pore volume are directly and linearly correlated. Panels d and e show the MALDI spectra of the recovery from crude serum, non porous silica and chip X11, in the peptide and protein range respectively.
Figure 22B:
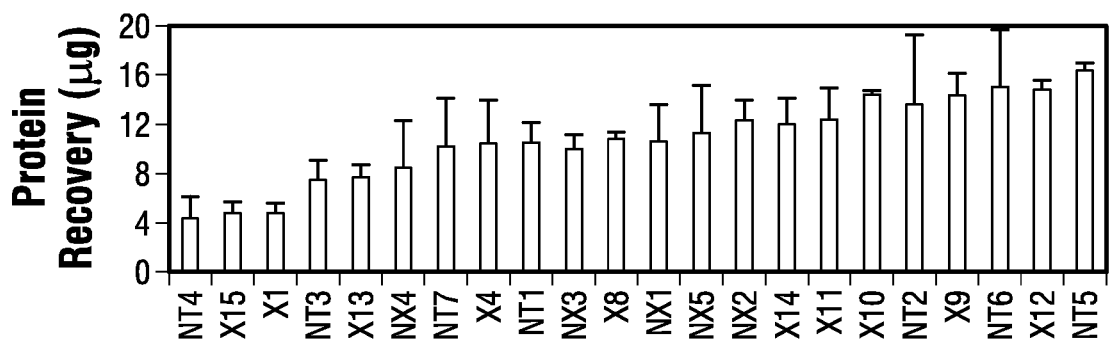
Figure 22C:
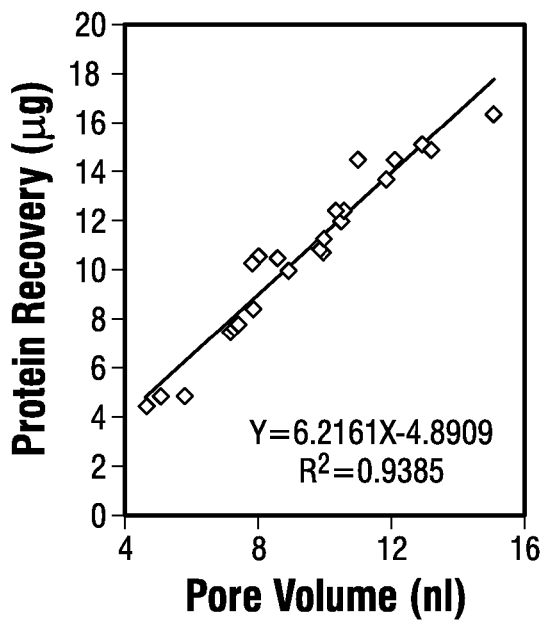
Figure 22D:
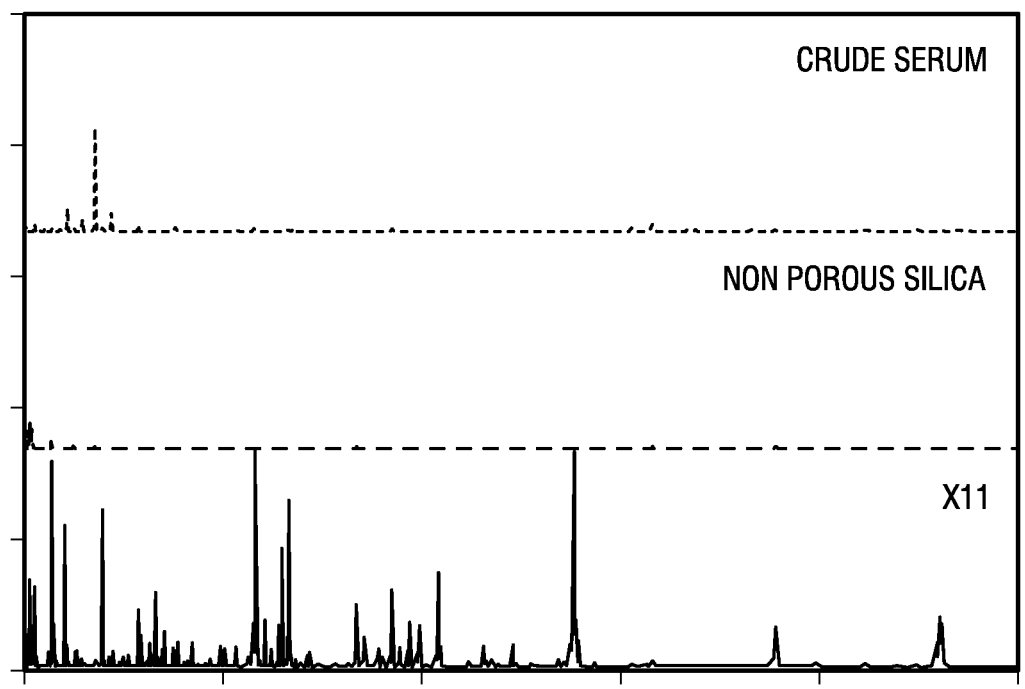
Figure 22E:
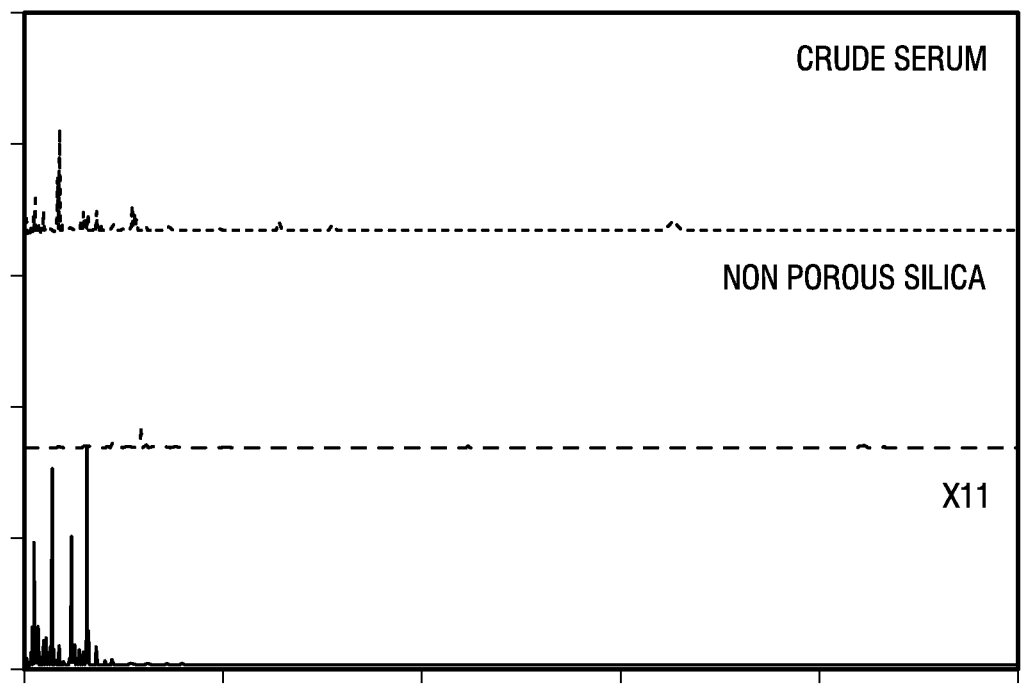
Figure 23A:
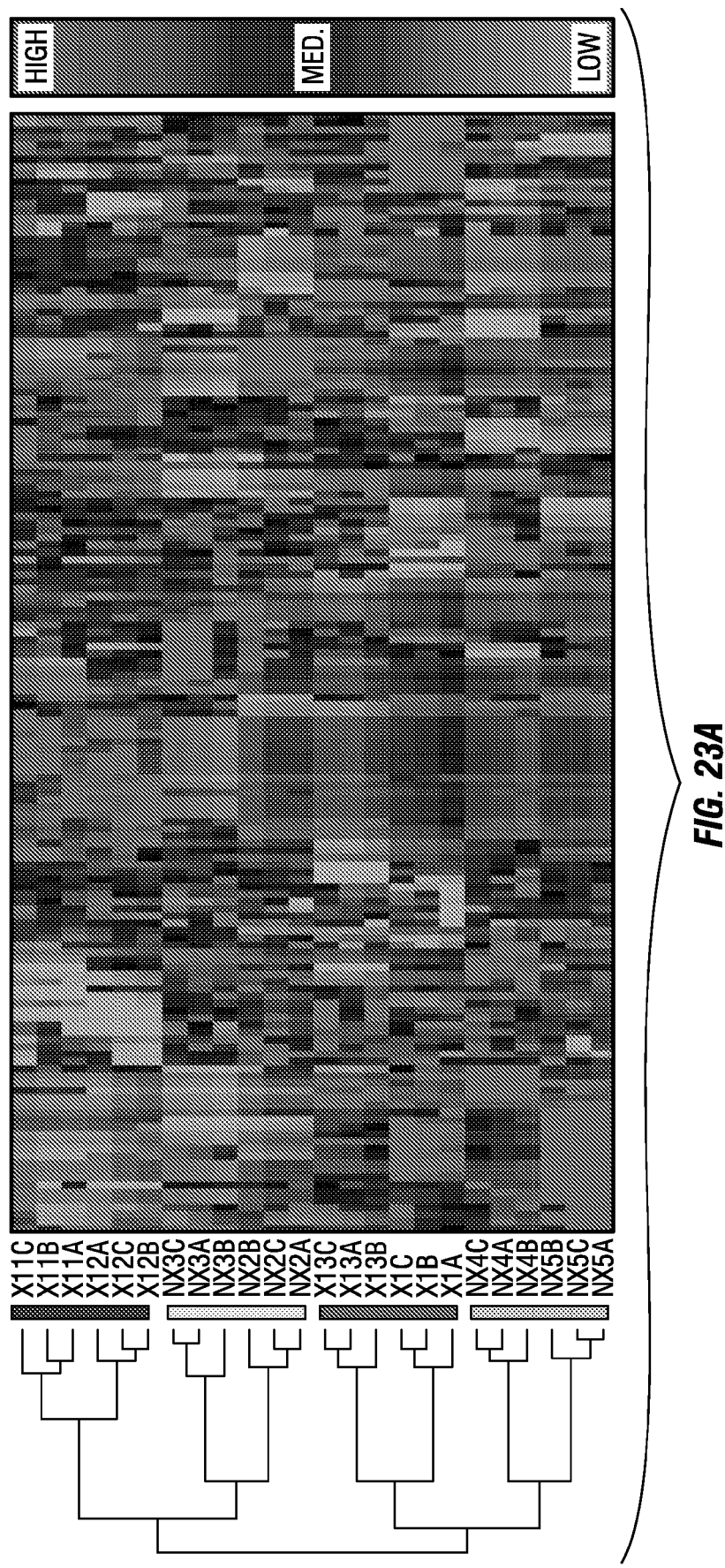
FIG. 23 shows the two-way hierarchical clustering analysis of fractionation of serum on different chips. In Panel a, unsupervised two-way hierarchical clustering analysis (two-dimensional complete linkage) was performed based on the intensity of detected proteomic features after fractionation on the different chips. The intensity of the red or green color indicates the relative protein concentration, that is, higher than or lower than the average value, respectively (black is the average value). Each row represents an individual peak signal and each column represents an individual sample (Chip). Each set of nanochips is clearly individualized. The dark and light blue rectangles represent large and small pores, respectively. The green and red rectangles represent the hydrophobic and TMB agent nanochips, respectively. Panel b shows supervised hierarchical clustering and specific recovery pattern for each set of nanochips as indicated in the figure (smaller vs. larger pores, hydrophobic vs. hydrophilic, TMB vs. PPG).
Figure 23B:
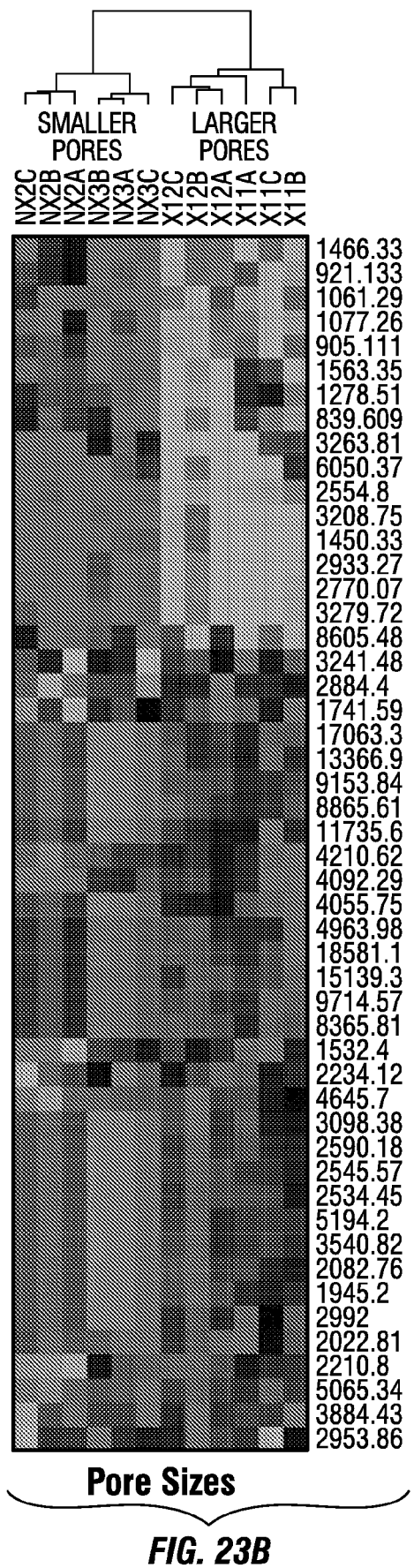
Figure 23C:
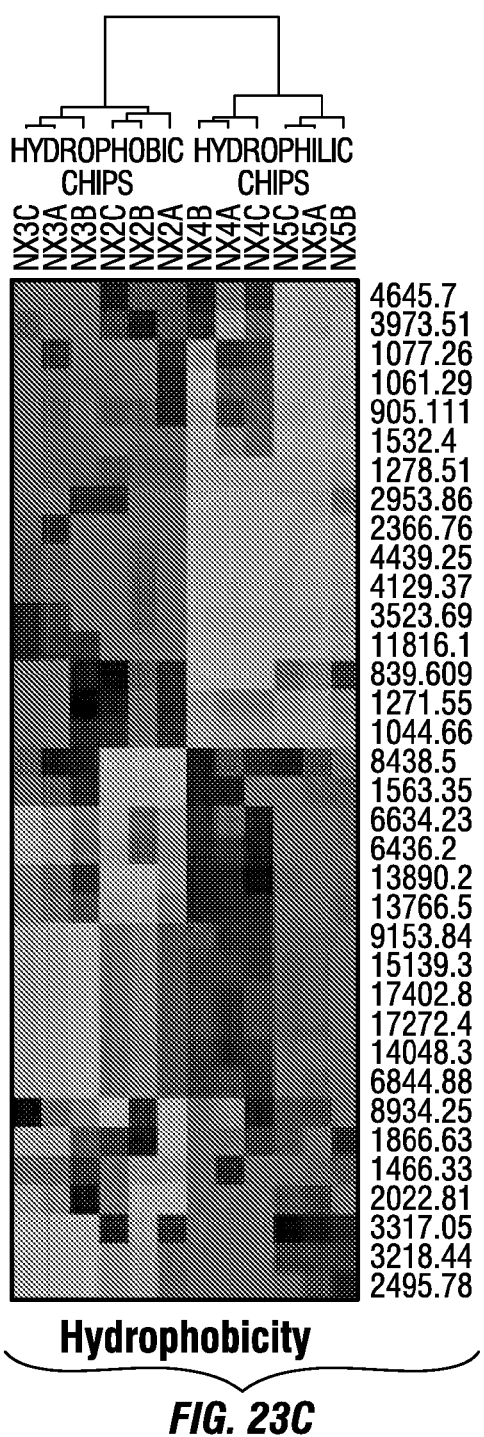
Figure 23D:
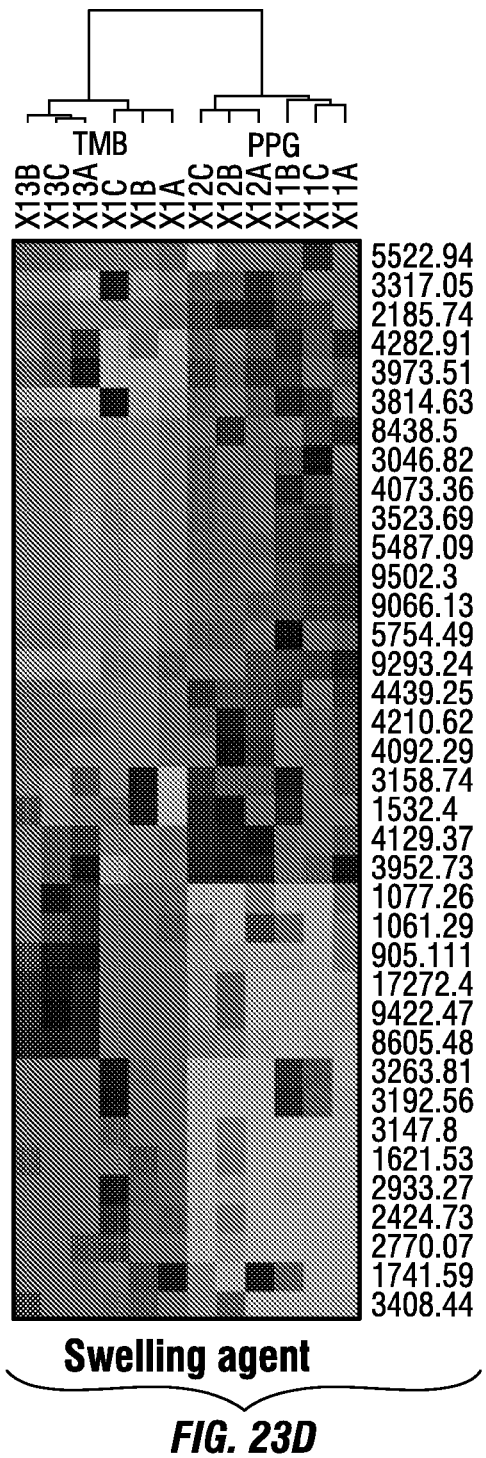

These results could be explained by the fact that more than the amount of serum, it was the binding capacity of the porous silica and the available volume of the pores, to be relevant for protein recovery. To better understand the mechanism underlying protein recovery, all the chips were characterized and the pore volume for each one of them was calculated. The complete list of the physico-chemical features of the chips is summarized in the table in FIG. 21. Using the same experimental protocol (fixed volume of serum: 10 µA; temperature: 25° C.; incubation time: 30 min; fractionating area: 6.5 mm), protein recovery was measured on each of the chips (FIG. 22b). By correlating protein recovery and pore volume (FIG. 22a), it was determined that there was a linear dependence between the efficiency of protein recovery and the total volume of the nanopores (FIG. 22c). This is a further demonstration that the physical properties of the nanoporous silica chips could be tuned and tailored to achieve the desired amount of protein to be recovered. As a control, the fractionation protocol was performed on non-porous silica and showed that neither proteins nor peptides were captured by the nonporous silica surface (FIG. 22 d and e, respectively).

Figure 9D:
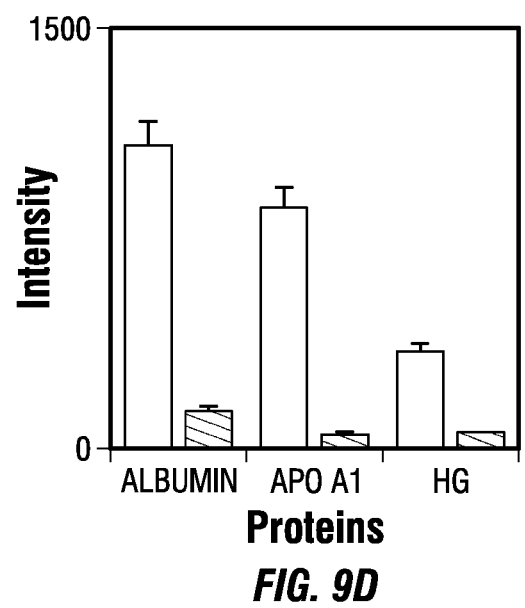
FIG. 9 shows the principle of MSC fractionation and LMW enrichment. Panel a shows that after serum spotting on the surface, LMW proteins and peptides are trapped into the pores while the larger species remained outside the pores and are removed during the washing steps. The enriched fractions are then eluted and analyzed by MALDI. Panel b shows the MALDI profiles of the different steps of the methodology demonstrate the depletion of most abundant HMW proteins in the washings and enrichment of LMW species in the elution. Panel c shows the comparison of the peptide/Albumin ratio, which illustrates the enrichment of LMW peptides detected in both serum (in red) and elution (in black). Panel d shows the comparison of the intensities of Albumin, Apolipoprotein A1, and Hemoglobin detected by MS in crude serum (in blue) and in the elution (in black).
Figure 9B:
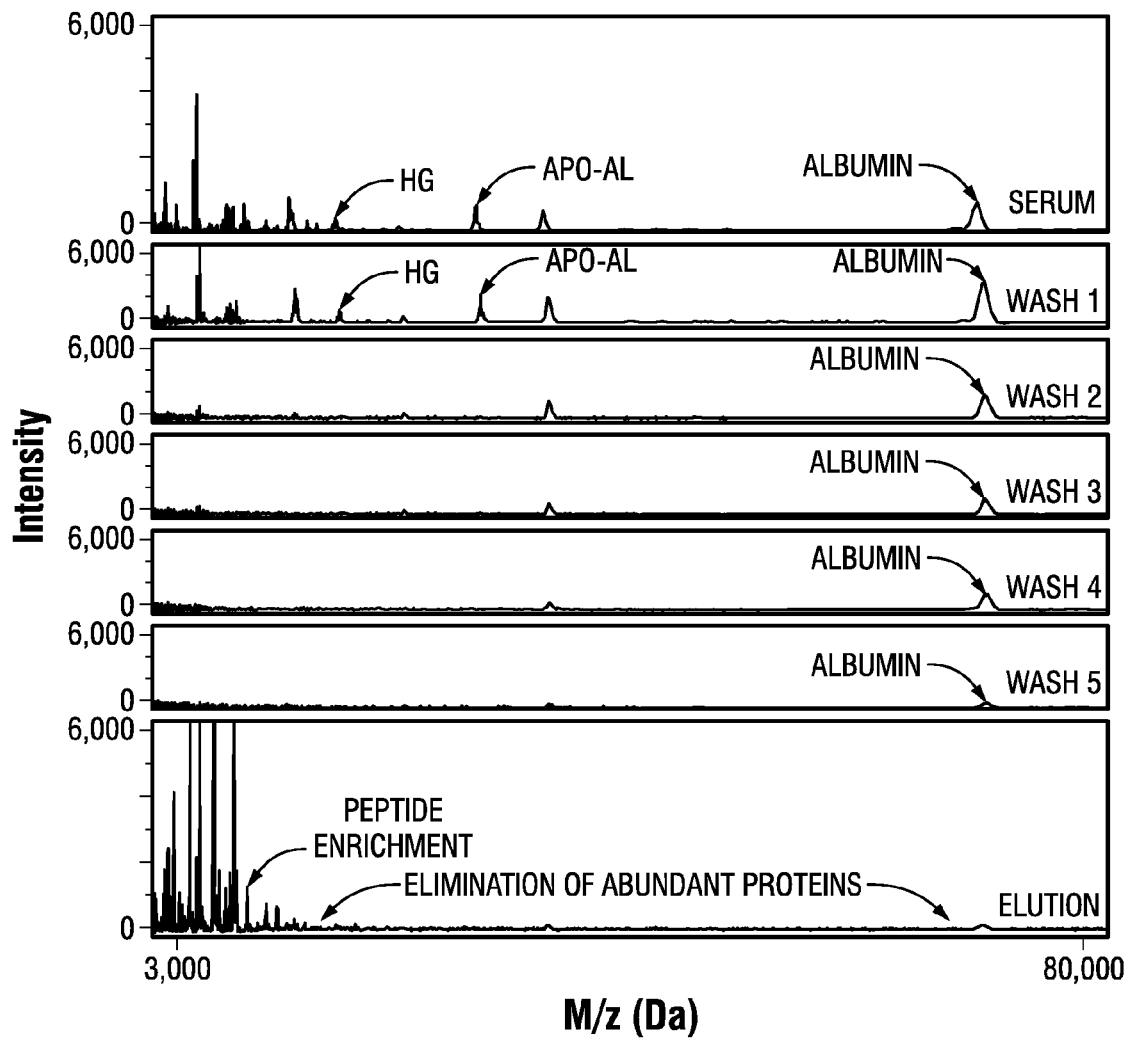
Figure 9C:
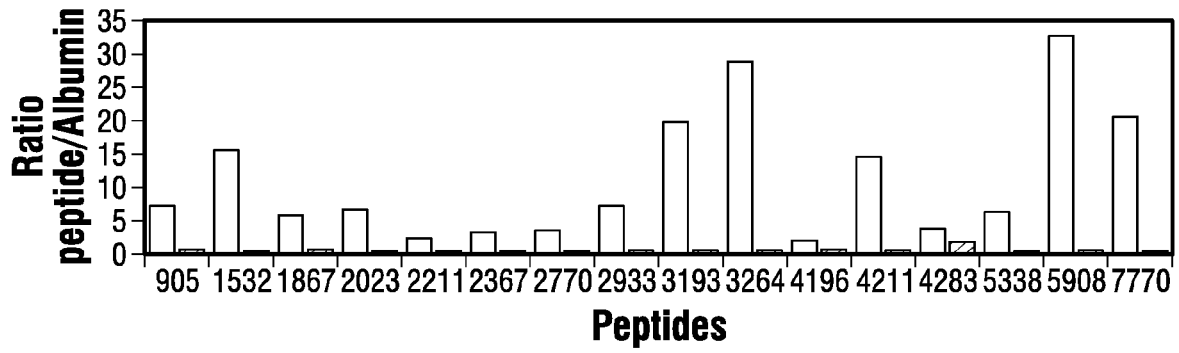

The MS profiles of human serum before and after fractionation on the MSCs were compared (FIG. 9b). The substantial enrichment of LMW species is illustrated in FIG. 9c by comparing the MALDI intensities of common peptides and proteins before and after the on-chip fractionation. The efficient removal of the most abundant HMW proteins (Albumin, Apolipoprotein AI and Hemoglobin) is shown in FIG. 9d by comparing their signal intensities in crude serum and after fractionation.

Figure 8C:
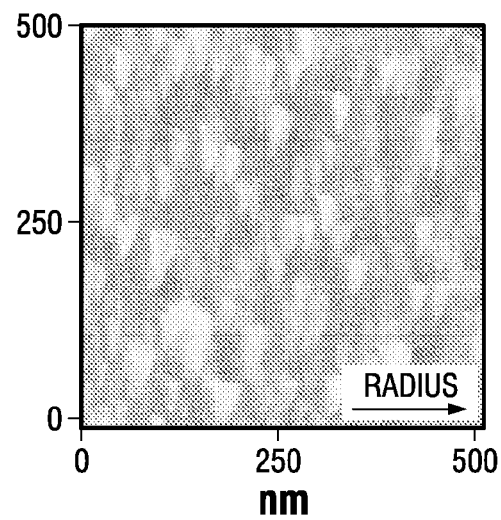
Figures 10I, 11:
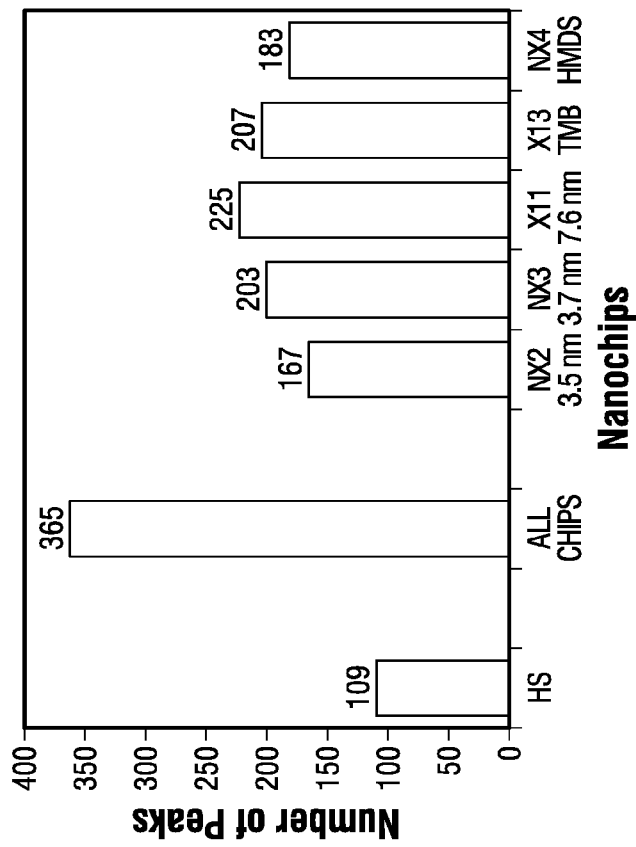
FIG. 11 is a table showing a summary of the chemical treatments and of the physical properties of the selected MSCs used for peptide and protein standard, and serum studies.

The physico-chemical properties of the chips correlated with their harvesting properties was characterized and the molecular cut-offs of each MSCs was identified. 26 peptides and proteins (See FIG. 22 and FIG. 5) were selected with a broad range of molecular weights (900-66,500 Da), isoelectric points (pI 4.0-10.2), and structures and used them to standardize the chips, the sample preparation, the MS analysis and the data processing. Each peptide and protein was verified by MS for its identity and purity (see FIG. 5). In order to assess size exclusion during the fractionation, 5 MSCs with pore sizes ranging from 2.7 nm to 8.9 nm were selected (FIG. 8 and FIG. 11). FIG. 24a shows the high detection signals of the standards when separated into two different solutions for the peptide range (16 markers from 900 to 8500 Da) and the protein range (16 markers from 3400 to 66500 Da). When combined in a unique solution, the detection signal in the peptide range dramatically decreased while the larger proteins remained well detected (FIG. 24b). The signal suppression in the LMW was due to the presence of large amount of well ionized HMW molecules such as Albumin and mimicked the limits of MS analysis of serum and plasma. The data presented in FIG. 25 demonstrate the ability to exclude the larger proteins and to increase significantly the detection of the LMW peptides and proteins. FIG. 26 gives a magnified view of the spectra illustrating the size-dependent removal of the larger proteins and the experimental molecular cut-off evaluated for each chip. FIG. 26c presents a two-way hierarchical clustering showing the positive correlation between pore size, the molecular weight of the trapped species and the enrichment of the LMW standards. MSCs with larger pores preferentially harvested bigger peptides (from 3600 to 8500 Da), while smaller peptides (from 900 to 3500 Da) were recovered more efficiently by the chips with smaller pores.

In the analysis of the fractionation and purification of LMW species from human serum, the chips were subdivided in 3 categories according to the properties of the material: 1—pore size; 2—hydrophobicity; 3—pore geometry and surface morphology. Unsupervised two-way hierarchical clustering (two-dimensional complete linkage) was performed to analyze the overall MALDI profiles of the different nanochips. FIG. 10a presents the resulting dendogram of samples clusters (the total hierarchical cluster is presented in FIG. 23). According to their harvesting characteristics, selective enrichment and specific recovery patterns, each of the MSCs identified unique proteomic signatures, as shown in the supervised hierarchical clustering (FIG. 10b-d; see also the hierarchical clusters with the mass list in FIG. 23b). The MS profiles of fractions obtained from the prototype device were combined (FIG. 10e-h) and demonstrated that the number of detected peptides and proteins in the LMW range was increased using the combinatorial multi-chip strategy (FIG. 10: 3 fold increase compared to untreated serum).

Example 4.5

Protein Fractionation Experimental Procedure

The MSC surface was wetted using isopropanol, washed with sterile $H_2O$ and air dried. For each experiment, a sample amount, which consisted of either plain human serum, or a solution containing different dilutions of recombinant peptides and proteins, was pipetted into the circular area defined by the different masks. Unless otherwise specified, for all the experiments shown in the paper 10 μA of sample were used for each analysis. The samples were incubated for 30 minutes in a wet chamber (100% humidity) to prevent sample evaporation. In order to identify the best working condition experiments were performed at either 4° C., 25° C. (RT), or 37° C. RT was selected as the optimal temperature and used for all the experiments showed in the paper. MSCs were washed 5 times with 154 of sterile, deionized water, allowing the droplets to rest on the surfaces for 0.5 minute for each wash. Peptides and proteins were eluted by using 10 μl of a 1:1 mixture of acetonitrile and 0.1% trifluoroacetic acid (TFA) (v/v) (Sigma) and pipetting the solution on the chip for approximately 1 minute. Aliquots of 1 μL of the mix of serum extracts and matrix solution were deposited on a MALDI sample plate and allowed to dry prior to mass spectrometric analysis. Protein content in samples was measured using a microBCA assay (Pierce, Rockford, Ill.) and read with the absorbance at 562 nm on a UV/Vis Spectrophotometer (Spectra Max M2, Molecular Devices). Absorbance values were converted into protein amounts using the formula calculated through a standardization curve. For the microBCA assay, 3, 5, 8, 10, and 12 μL of the sample for washes 1-5 respectively and 3 μL of the elution sample were diluted in water to make 500 μL. This diluted protein was mixed with 500 μL of the microBCA buffer and incubated for 1 hour at 60° C. The samples were allowed to cool to room temperature and then read on the spectrophotometer.

Example 4.6

Mass Spectrometry

A matrix solution of 5 mg/ml α-cyano-4-hydroxycinnamic acid (αCHCA, Sigma) in a 1:1 mixture of acetonitrile and 0.1% TFA(v/v) and a saturated matrix solution of trans-3,5-dimethoxy-4-hydroxycinnamic acid (SA, Sigma) in 2:1 mixture of acetonitrile and 0.1% TFA was used for Low Molecular Weight (LMW) and High Molecular Weight (HMW) peptides and proteins respectively. Each sample was mixed with the appropriate matrix in a 1:3 ratio, and spotted in duplicate onto the MALDI plate. Mass spectra were acquired on a Voyager-DE™-STR MALDI-TOF (Applied Biosystems, Framingham, Mass.) mass spectrometer in liner positive-ion mode, using a 337 nm nitrogen laser. Samples were evaluated at two m/z ranges. For the m/z range of 800-10,000 Da, settings were optimized at acceleration voltage 20 KV, grid voltage 19 KV, guide wire voltage 1 KV, delay time 180 ns, and low-mass gate 800. For the m/z range of 3,000-100,000 Da the instrument was optimized at acceleration voltage 25 KV, grid voltage of 23.25 KV, guide wire voltage 6.25 KV, delay time of 500 ns and low mass gate 3,000. Each spectrum was the average of 300 laser shots. The spectra were calibrated externally using the ProteoMass standards of peptides and proteins (Sigma) in each mass range.

Example 4.7

Data Processing and Statistics

The raw spectra were processed with the Voyager Data Explorer software version 4.0 (Applied Biosystems) and the data were exported to SpecAlign software for pretreatment. All spectra were aligned using the PAFFT correlation method and intensity was normalized to total ion current (TIC). The peak detection was performed with a height ratio of 2 with 0.3% of the mass window and the baseline was corrected and the negative values were removed prior to analysis.

Hierarchical clustering was performed using Cluster software and visualized with Treeview software. MALDI MS Data (M/z peak intensities) were log-transformed, normalized and median centered. Pearson correlation was used to calculate the distance between the samples, and complete linkage clustering was performed. For supervised hierarchical clustering, an independent Student t-test was used for comparison between groups (n=2 groups) for each detected MS peak. A P value of 0.02 or lower was considered significant to select differentially harvested peptides and proteins among the different mesoporous proteomic chips (Large pores vs. Small pores, Hydrophobic vs. Hydrophilic, TMB vs. PPG swelling agents).

Example 5

Methods and Materials

Example 5.1

Fabrication and Characterization of Mesoporous Silica Thin Films

Most of the procedures used for the synthesis of mesoporous silica films are similar to the ones described by Zhao et. al. (Science, 1998, vol 279: 548-553). The primary objective of this study was to tailor MPS thin film pore morphology and internal structure by adjusting synthetic parameters and to explore their efficacy for the specific harvesting of LMWP species from human serum. A consistent proteomic profiling approach requires that the MPS-based serum fractionation be performed with a well defined high purity substrate possessing good thermal stability as well as uniform nanostructure and film thickness throughout the entire mesoporous silica layer. The preparation of the precursor solution, involving the cooperative assembly of a polymer surfactant and soluble silicate species, play a dominant role in determining the molecular organization of the final product. The molar ratios of starting materials are listed in Table 1 for each block copolymer used. To prevent shrinkage of the MPS thin films, deposited film thickness did not exceed 1 μm. This was accomplished by maintaining the molar ratio of ethanol to silicate to between 12 and 14 and water to silicate at less than 6. The pH of the precursor solution was kept in the range of 1.2 to 1.5 in order to avoid the precipitation of silicate and to achieve equilibrium between the condensation of silicate onto the polymer micelles and its hydrolysis in solution. Porosity and pore structure were adjusted by changing the molar ratio of the polymers in the mixture. Spin coating, superior to other deposition techniques for achieving uniform thickness and porosity, was used to form the MPS thin films on a silicon substrate. The substrates were then cleaved to produce chips for quantitative proteomics analysis. Previous literature has demonstrated that mesoporous silica products can exhibit substantial non-uniformity as a result of inadequately controlled synthesis due to the weak interaction between molecules during the self-assembly process. Other experimental parameters, such as aging time of the precursor solution, coating speed during solution deposition, and calcination temperature were studied to understand their impact on the final features of the mesoporous structure. To reduce experimental complexity, only the amphiphilic structure of the block co-polymers and their concentration in the precursor solution were adjusted, with all other process parameters held constant, to investigate their effect on pore geometry, morphology, and connectivity.

To characterize the pore architectures and physico-chemical properties of MPS thin films, various techniques were employed, including ellipsometry, 1-dimensional X-ray diffraction (1D-XRD), $N_2$ adsorption/desorption, transmission electron microscopy (TEM), X-ray photoelectron spectroscopy (XPS) and surface contact angle goniometry. FIG. 29 depicts the overall purity and the atomic silicon-to-oxygen ratio of the MPS thin films prepared with L121 as the structure-directing template are determined by XPS using the Si2p, O1s and C1s regions of the spectra. The very weak signal for the C1s region can be attributed to minimal contamination (i.e. hydrocarbons) on the film surface. Both the Si2p and O1s regions consisted of a sharp and symmetric single peak at binding energies around 101.4 eV and 530.7 eV respectively, which strongly point to a silica framework with high condensation. By calculating the areas under the peaks for Si2p and O1s, an atomic silicon-to-oxygen ratio of 1:2.004 was obtained to further confirm the high purity of MPS thin films. Similar XPS results were acquired for MPS thin films synthesized using the alternative polymer templates.

Example 5.2

Serum Fractionation on Mesoporous Silica Thin Films

Figure 30A:
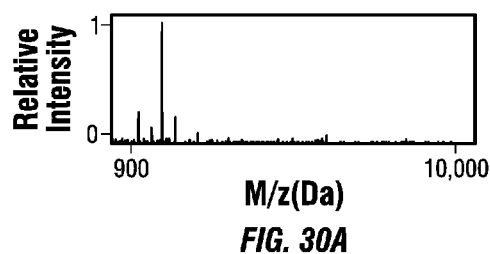
FIG. 30 shows the efficacy of serum fractionation using the mesoporous silica thin film chips. MALDI MS profiles are shown in both the low mass range (900 to 10,000 Da) and the high mass range (3,000 to 70,000 Da) before (a, b) and after (c, d) fractionation using the mesoporous silica thin films. The molecular recovery is significantly reduced when using blank non-porous silica surfaces for fractionation (e, f).
Figure 30B:
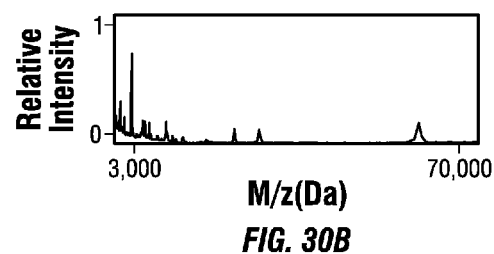
Figure 30C:
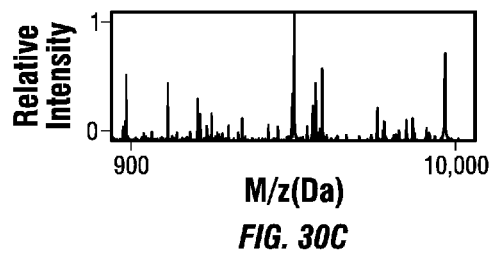
Figure 30D:
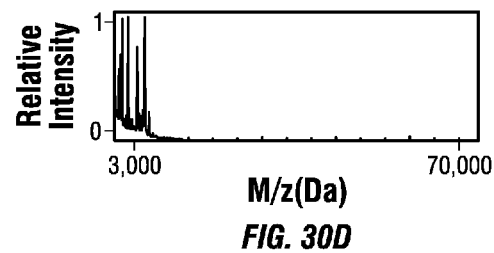
Figure 30E:
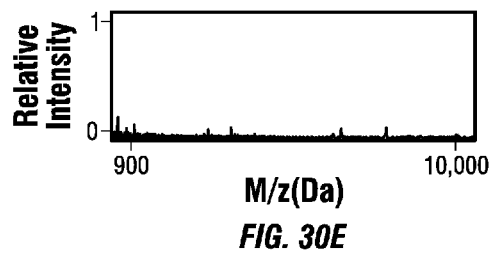
Figure 30F:
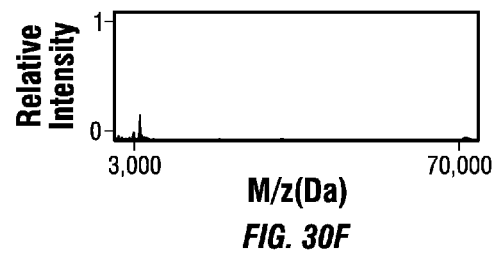

The protocol for serum fractionation using MPS thin films is described in the experimental section. Briefly, the serum sample was first spotted on the MPS chip and incubated at room temperature for 30 minutes. This procedure trapped LMW molecules in the pores while the larger proteins remained in solution on the MPS thin film surface. After multiple washings with deionized water to remove the large proteins from the surface, the trapped LMWP was eluted from the pores using an acidic solution. FIGS. 30a and 30b show the MS spectra of a serum sample with peptides in the range of 900 to 10,000 Da and proteins in the range of (3,000~70,000 Da) respectively which have not undergone fractionation by the MPS thin films. These spectra illustrate the signal suppression in the LMW region due to the presence of well ionized, highly abundant, high molecular weight (HMW) proteins (Albumin, ApoA1). FIGS. 30c and 30d depict the MALDI-TOF spectra of the serum sample after fractionation by the MPS thin films synthesized using L121 and swelling agent PPG at a molar ratio of 1:0.5. Enrichment of the LWM components is clearly evident as the majority of the large molecules in the serum sample haven been removed. As a control, the same serum sample was applied onto a nonporous pure silica surface to evaluate the specificity of MPS thin films for LMWP recovery. As can be seen in FIGS. 30e and 30f, there was no significant harvesting of peptides or proteins from the nonporous silica surface observed in the range of interest for both the peptide and protein mass. Thus it can be concluded that it was the mesoporous architecture and not the silica surface affinity that constitutes the predominate factor in the enrichment of LMWP.

Example 5.3

Reproducibility of Serum Fractionation on Mesoporous Silica Thin Films

Figure 31A:
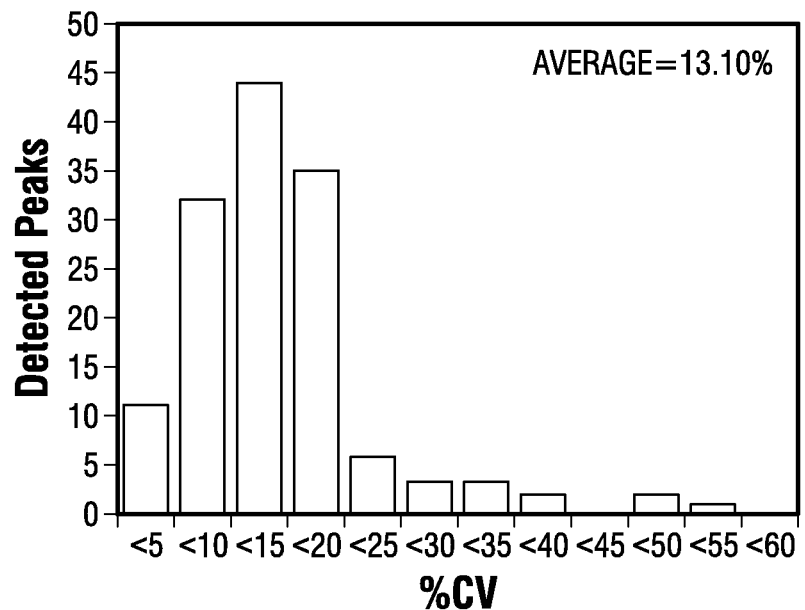
FIG. 31 shows a statistic study of reproducibility of onchip fractionation. Panel a shows the coefficient of variation (CV) distribution of MS intensities for detected peaks. The average CV is indicated in the figure. Panel b the linear regression analysis of average intensities of detected MS peak in each replicate compared to replicate 1. The equation and the coefficient of determination ($R^2$) are presented
Figure 31B:
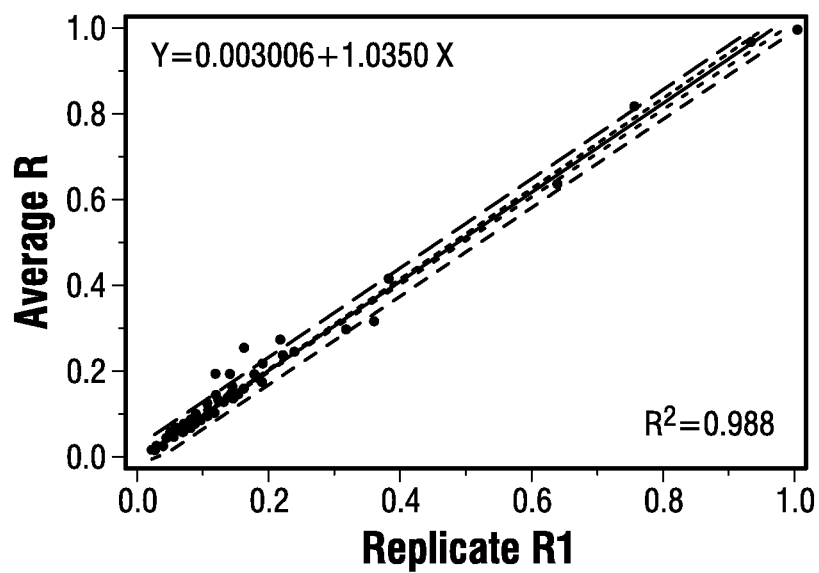

Due to the relative instability of blood samples, several publications have reported the importance of pre-analytical sample management to avoid the accumulation of artifacts and significant alterations in the proteomic profiles. Therefore, fractionation reproducibility and reliability are mandatory for any further development of a reliable proteomic and peptidomic screening techniques for clinical applications. To assess the consistency of the on-chip fractionation strategy, 6 replicates with 6 aliquots of the same human serum sample were screened using MPS thin films prepared by L121+PPG with a molar ratio of 1:0.5. The general variability of the peak signals is illustrated on the histogram displaying the reparation of the coefficients of variation (CV) measured for each detected peak (FIG. 31a). The average CV was estimated at 13.1%, which demonstrated a high reproducibility for the detected peaks over a wide mass range of 800 to 20,000 Da. The regression curve and equation comparing the peak intensities recovered from the replicates are illustrated in FIG. 31b and exhibit a coefficient of regression $R^2$=0.988. These results confirmed that the on-chip serum fractionation did not induce any significant variability in the sample and demonstrated the reliability of the MPS chips in the pre-treatment of complex biological samples. The minor statistical variations are due to the internal variability of the MALDI instrument.

Example 5.4

Effect of Pore Structure and Distributional Architecture on LMWP Recovery

Figure 32A:
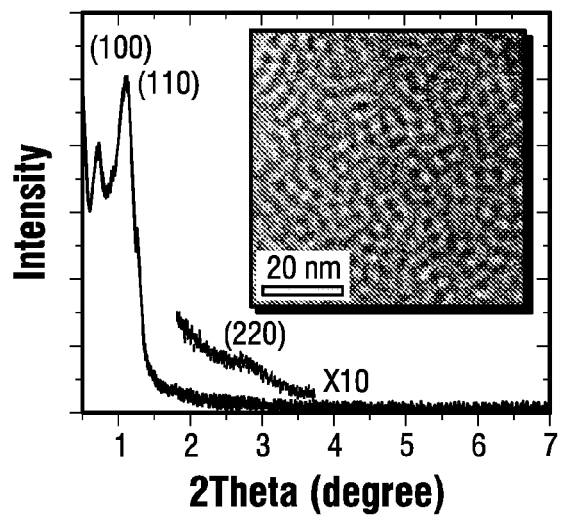
FIG. 32 shows the physical characterizations of MPS thin films. XRD patterns (a, c, e), TEM (inset a, c, e), and $N_2$ adsorption/desorption analysis (pore size distribution in b, d, f, isotherms in the insets of b, d, f), of the structural transformation of mesoporous thin films prepared using Pluronic F127 at different concentrations in the precursor solution: $4.0 \times 10^{-3}$ M (a, b), $6.0 \times 10^{-3}$ M (c, d) and $8.0 \times 10^{-2}$ M (e, f).
Figure 32B:
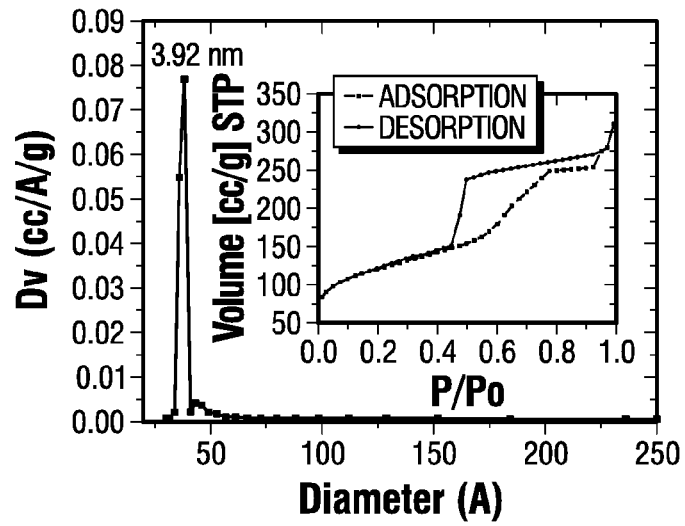
Figure 32C:
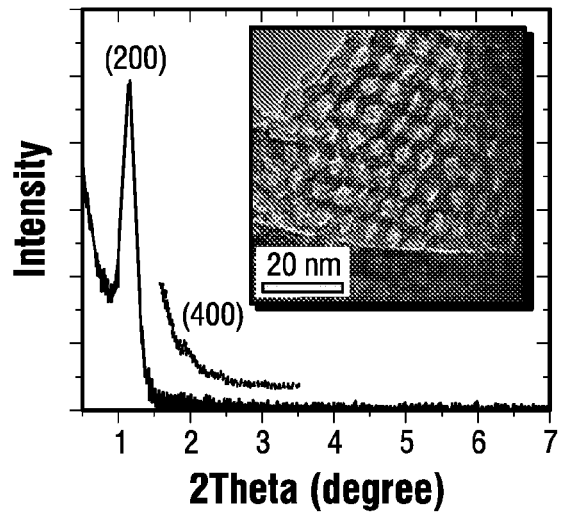
Figure 32D:
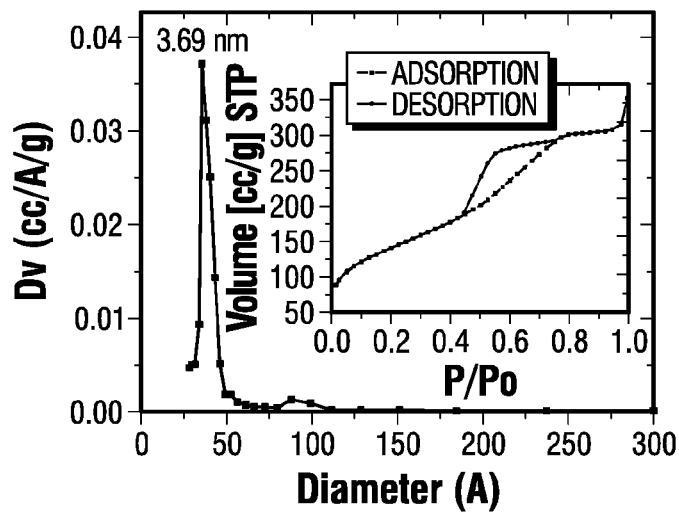
Figure 32E:
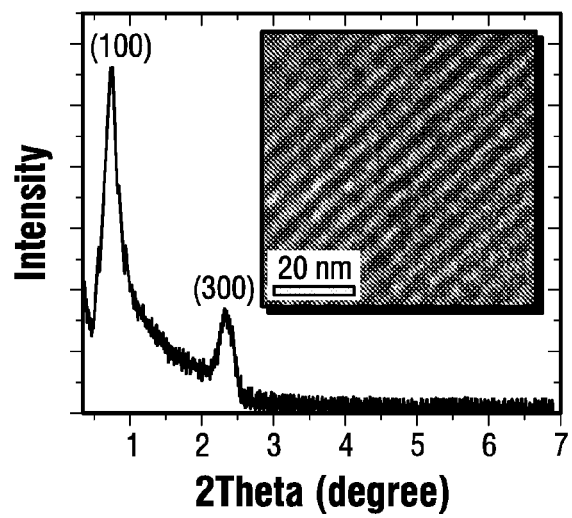
Figure 32F:
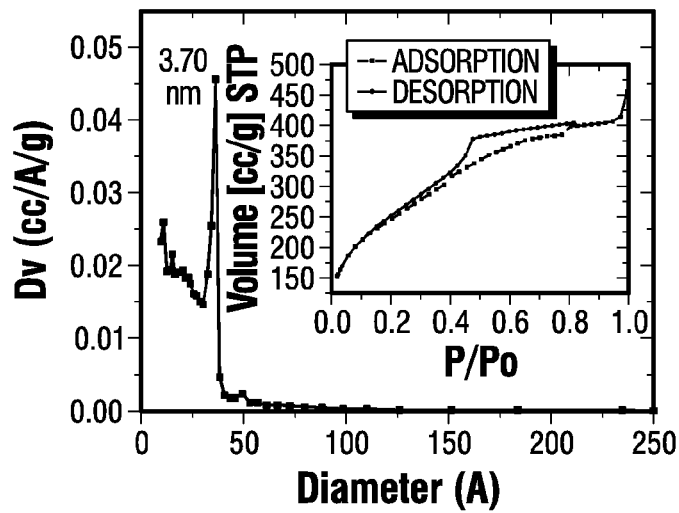

One main advantage of block copolymers with high molecular weight, in comparison to those of low molecular weight, is their ability to form a variety of structures by tuning experimental conditions during MPS thin film synthesis. The structural transformation of the mesoporous arrangement was carried out by tuning the concentration of the template polymer. Increasing the concentration of the template polymer resulted in a reduced interfacial curvature between the phases of the water, the copolymer, and the silicate, consequently initiating the interrelated progression from a spherical to a cylindrical structure. Pluronic F127, with its high molecular weight, possesses this high degree of structural periodicity. In this study, the concentrations of all starting materials, except F127, were kept constant. FIG. 32 demonstrates the changes in the nanostructure of the MPS by characterization through XRD pattern, TEM imaging and $N_2$ adsorption/desorption analysis. When the F127 concentration in the precursor solution was kept at $4.0 \times 10^{-3}$ M, the final MPS thin film acquired a 3D cubic structure with reflection peaks at (100) and (110) and a low intensity peak at (220) as indicated by the XRD pattern (FIG. 32a) and further verified through TEM imaging (inset of FIG. 32a). $N_2$ adsorption/desorption curves were generated using a Quantachrome Autosorb-3b BET Surface Analyzer (inset of FIG. 32b) and the pore size distribution was calculated using the Barrett-Joyner-Halenda (BJH) method (FIG. 32b). The adsorption/desorption isotherms describe a Type IV isotherm with a H2 hysteresis loop (sloping adsorption branch and nearly vertical desorption branch) indicating a nanoporous structure with interconnecting channels. Inflection points appearing at $0.40 \leq P/P_0 \leq 0.75$ in the figure indicated the formation of ink-bottle shape nanopores. Increasing the F127 concentration to $6.0 \times 10^{-3}$ M yields a 3D honeycomb like nanostructure hexagonally arranged on the substrate, as confirmed by XRD, with peaks at (200) and (400) (FIG. 32c), and TEM (FIG. 32c inset). The adsorption/desorption isotherms, depicted with the pore size distribution in the inset of FIG. 32d, vary slightly from the similar adsorption-desorption Type VI isotherms described for the lower concentration F127 MPS thin films due to the increased internal pore connectivity. A further increase of the F127 concentration to $8.0 \times 10^{-3}$ M resulted in a 2D hexagonal nanostructure parallel to the substrate surface. The sharp peaks at (100) and (300) in the XRD pattern (FIG. 32e) and TEM imaging (FIG. 32e inset) confirm this conclusion. The adsorption/desorption isotherms (FIG. 32f inset) displays a narrow hysteresis loop indicating significantly less inter-pore connectivity than either of the previous two MPS thin film morphologies. The similar pore size distributions of the 3 different nanostructure, with average pore sizes around 3.7 nm, illustrate that the change of pore size was minimally dependent on the molar ratios of the starting materials.

Figure 33A:
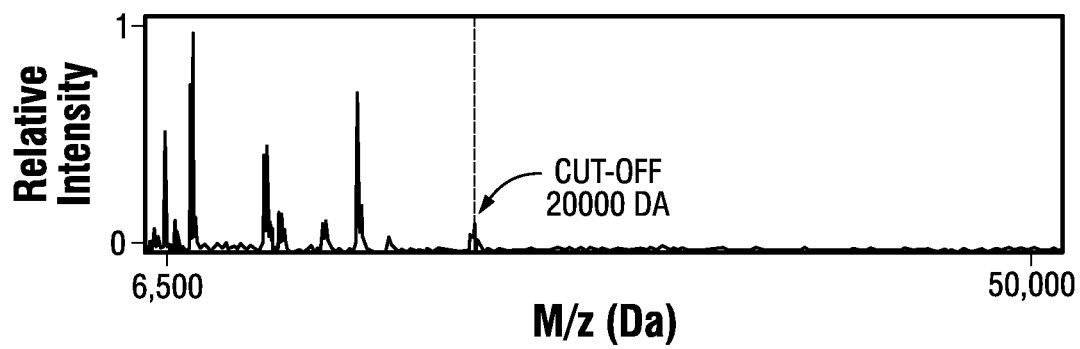
FIG. 33 shows the molecular cut-off for F127 chips. The molecular cut-off of recovered proteins is shown for the MPS thin films prepared by Pluronic F127 with different nanoscale morphologies: 3D cubic (a), 3D honeycomb hexagonal (b) and 2D hexagonal (c).
Figure 33B:
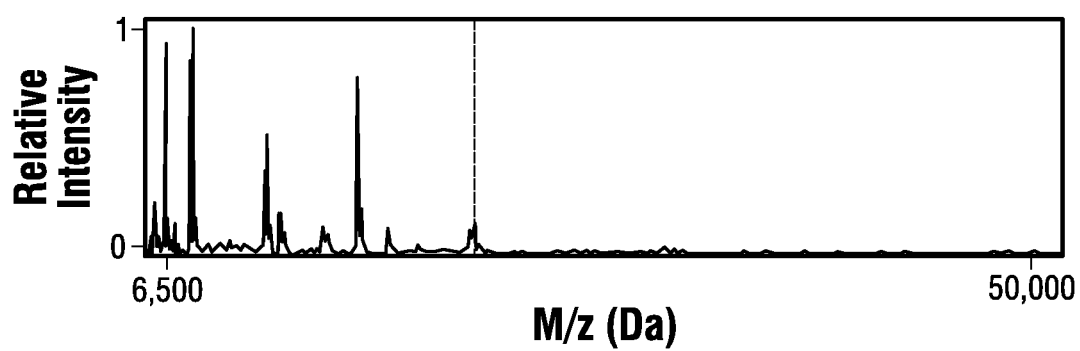
Figure 33C:
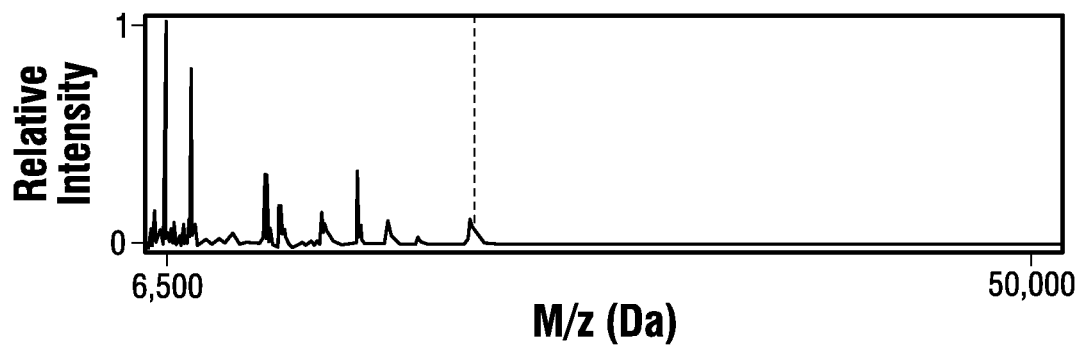
Figure 34A:
FIG. 34 shows the effect of pore structural transformation on LMWP recovery from F127 chips. The MALDI profiles for the 3D cubic (a), 3D honeycomb hexagonal (b) and 2D hexagonal (c) nanoscale morphologies, respectively. The coefficient of variation (CV) distributions of MS peak intensities for each of the MALDI profiles are also shown (d, e, f). The average CV and the number of detected peaks are indicated in each histogram.
Figure 34B:
Figure 34C:
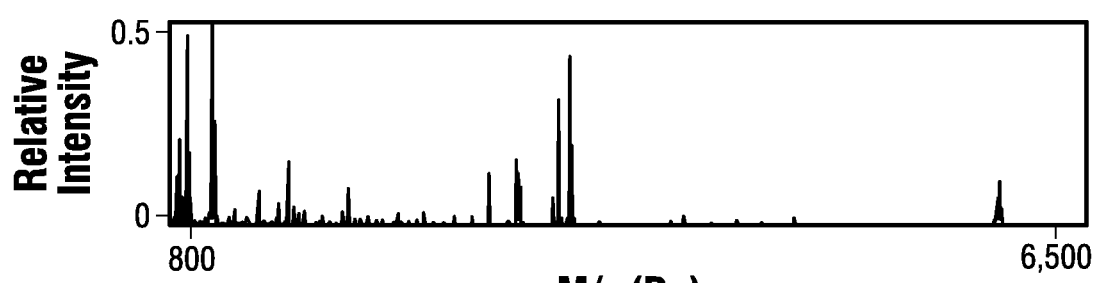
Figure 34D:
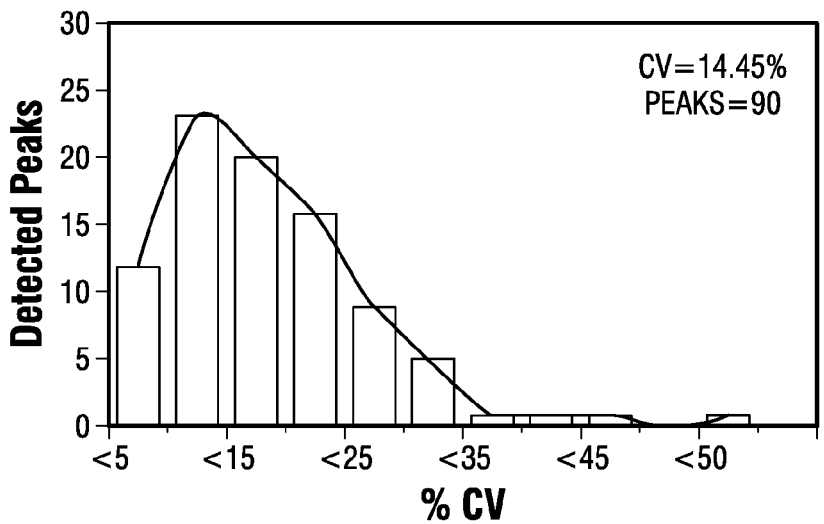
Figure 34E:
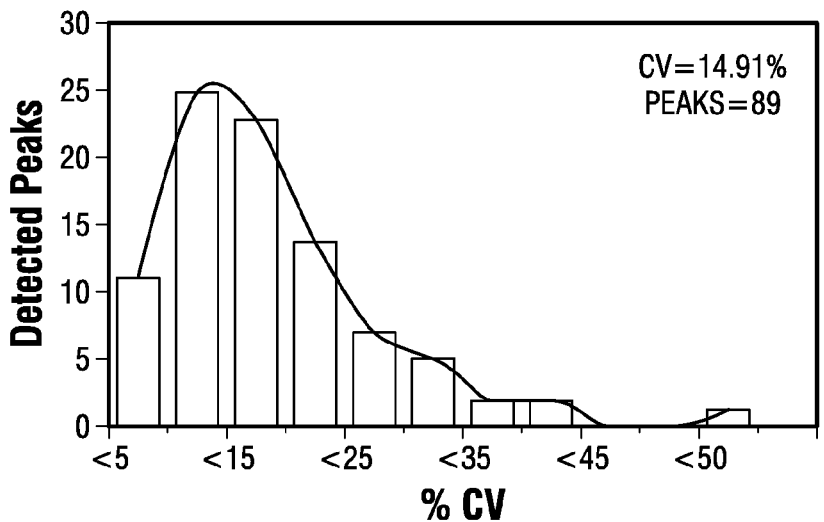
Figure 34F:
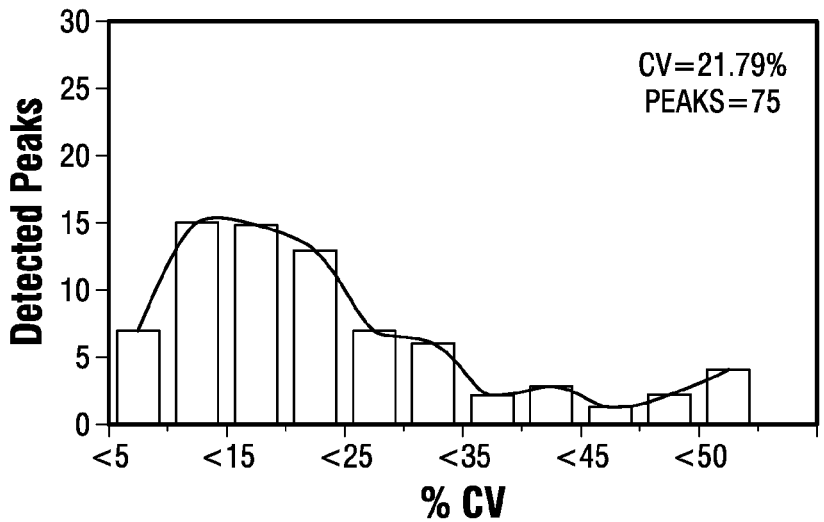

After demonstrating that it was possible to fabricate MPS thin films with different pore morphology, the effect of the structural variation of the mesoporous F127 nanochips (3D cubic, honeycomb hexagonal and 2D hexagonal) on the specific enrichment of LMW species was investigated. As shown in FIG. 33, MPS thin films with similar pore size distributions, around 3.7 to 3.9 nm, and the three different nanostructures (FIG. 33a for 3D cubic, FIG. 33b for 3D honeycomb-like hexagonal and FIG. 33c for 2D hexagonal) exhibit the same molecular cut-off for peptide and protein recovery from serum fractionation. For both 3D nanoporous morphologies, the increased pore connectivity and the reduced steric hindrance imposed on the diffusion of peptides and proteins resulted in higher recovery efficacy. The dramatic difference in the MS profiles for peptides recovery in the range of 800~10,000 Da between 3D nanostructures and 2D hexagonal framework was shown in FIG. 34a, c b and e. The average coefficient of variation (CV) determined from the histograms, for 3D cubic structure (FIG. 34b) or 3D honeycomb hexagonal structure (FIG. 34d) is considerably lower than that of the 2D hexagonal architecture (FIG. 34f), which shows a broader CV distribution. These results indicate that the serum fractionation on the MPS thin film with a 3D nanotexture possesses a comparatively lower variability because of the 3D structures' greater pore connectivity.

Example 5.5

Effect of Selecting Polymer Template on LMWP Recovery

Figure 35A:
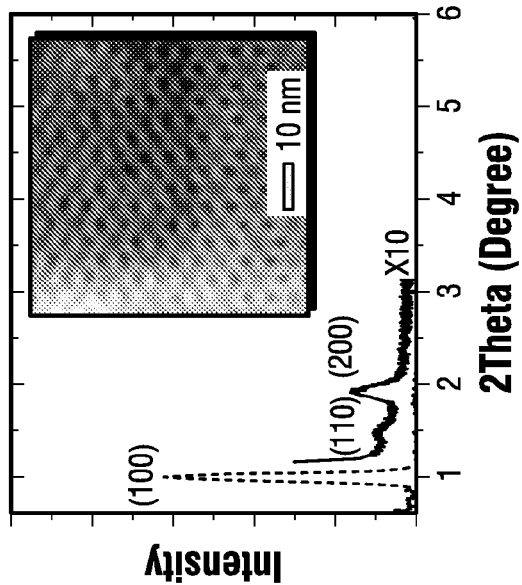
FIG. 35 shows XRD spectra and STEM images (inset) of mesoporous silica thin films prepared using a. P123 at P123/TEOS=5.9×10$^{-3}$, b. F127 at F127/TEOS=1.13><10$^{-2}$, c. L64 at L64/TEOS=2.14×10$^{-2}$, d. L121 at L121/TEOS=1.09×10$^{-2}$ with PPG at a molar ratio of 1:0.5. The STEM images are obtained normal to the thin film surface.
Figure 35B:
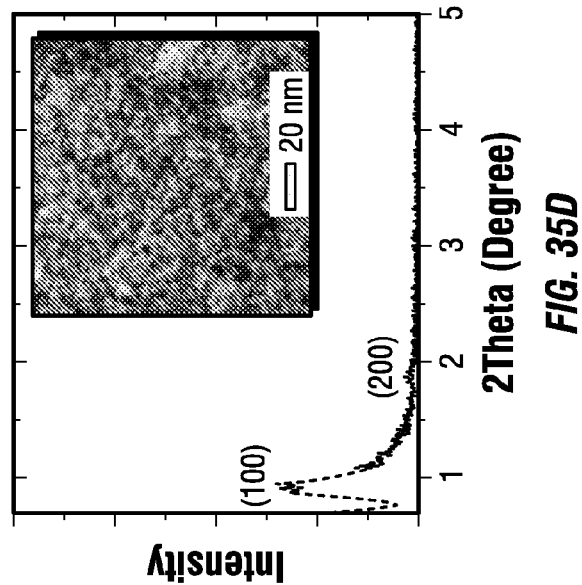
Figure 35C:
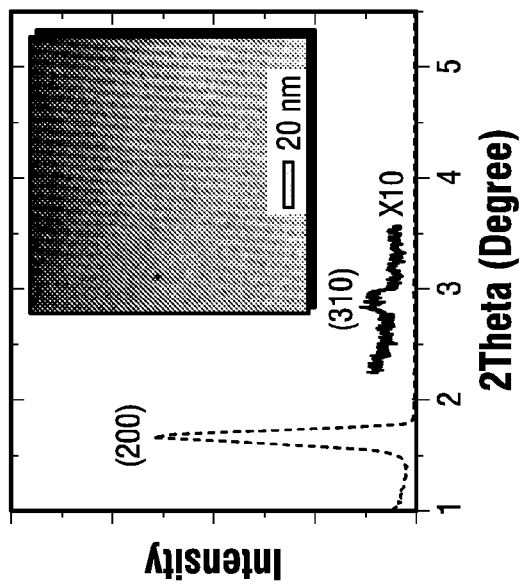
Figure 35D:
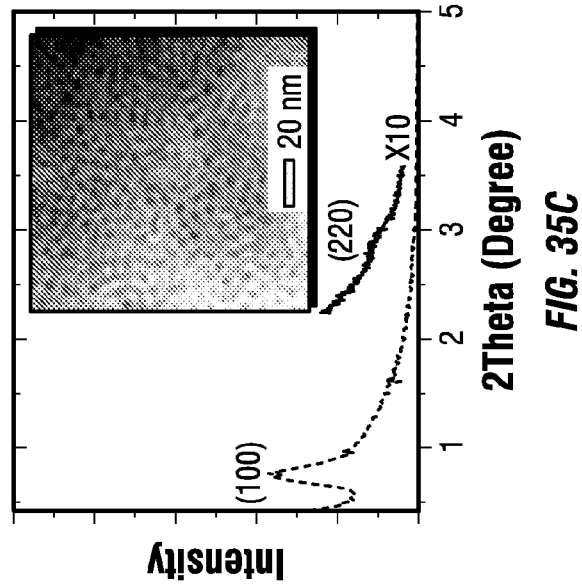

Another factor that influences the interfacial curvature between the polymer and the other solution components (TEOS, water, etc.), and thus determines the nanostructure and the pore size, is the hydrophilic/hydrophobic volume ratio of the copolymer. A series of tri-block copolymers with different hydrophobic (PPO) to hydrophilic (PEO) volume ratios were selected to synthesize the MPS thin films with different pore sizes and morphologies and subsequently investigated for their LMWP harvesting efficacy. Block copolymer compositions with longer PPO block lengths lead to increased pore size. Longer PEO block lengths for a given PPO block length (L121 versus P123 versus F127) lead to the formation of more highly ordered periodic nanostructures. L-type (liquid phase) block copolymers (such as L64 and L121) with lower PEO block lengths offer increased porosity due to their greater deforming performance but more chaotic nanostructure. FIG. 35 displays XRD patterns with the Scanning Transmission Electron Microscopy (STEM) imaging (insets) performed for MPS thin films prepared from P123, F127, L64 and L121+PPG (with molar ratio of 1:0.5) detailing their internal nanoscale organization. In the spectra for the MPS thin film prepared with P123 (molar ratio P123/TEOS=5.9×10$^{-3}$) (FIG. 35a), the appearance of an intense and narrow peak for the (200) reflection at 1.66° of 2θ and $d_{200}$=5.31 nm combined with a lower intensity (310) peak at 2θ=2.99° indicate the formation of a hexagonally arranged periodic silica nano-composite thin film after calcination at 425° C. The absence of the (110) reflection indicates that the (100) plane of the 2D hexagonal unit cell was parallel to the surface of the silicon substrate. The plane view of STEM imaging shows the continuous mesochannels on the top of the film and provides the direct evidence for the formation of a 2D hexagonal nanostructure. The MPS thin film prepared with F127 (FIG. 35b) (molar ratio F127/TEOS=1.13×10$^{-2}$) also exhibits an ordered nanoporous morphology indicated by the highly intense (100) reflection peak at 2θ=0.99° ($d_{100}$=8.89 nm). The lower intensity peaked at (110) with $d_{110}$=6.27 nm and (200) with $d_{200}$=4.80 nm points to the formation of a 3D honeycomb-like hexagonal nanostructure, which is confirmed by the STEM imaging (FIG. 35b inset). The XRD patterns and the STEM imaging (insets) for those fabricated by L-type block copolymers are shown in FIGS. 35c (for L64) and 35d (for L121 with PPG). Their low intensity and broad peaks in the small angle region were caused by the formation of unordered worm-like nanopores.

$N_2$ adsorption-desorption isotherms were measured to assess pore size distribution and total surface area of the MPS thin films. The BJH pore size distributions for chips prepared by P123 (FIG. 36a) and L121 (FIG. 36b) are provided, each depicting low pore size dispersion as denoted by their sharp distribution peaks, along with their adsorption/desorption isotherms (insets). FIG. 36a show Type IV adsorption/desorption isotherms with well-defined H2 hysteresis loops. The MPS thin films prepared using P123 and F127 possess similar mean pore size (~3.7 nm) due to their identical PPO block volume, but the MPS prepared with P123 possesses a poor connectivity indicated by its narrow hysteresis loop. Shown in FIG. 36b for chips prepared with L121, the pore diameter distribution peaks shift towards the right from 5.82 nm to 6.79 nm and became broader with increasing amounts of the swelling agent. Their adsorption/desorption isotherms were also Type IV but with a H1 hysteresis loop attributed to cylindrically shaped pores. Adding the certain amount of PPG did not result in any change in the loop shape, that indicates the inner pore connectivity is not destructed by the swelling agent used for the chips prepared with L121. Although the MPS thin films prepared with L64 possesses the similar adsorption/desorption isotherms with L121, its shorter hydrophobic chain (PPO) led to nanopores with smaller pore size (~3.2 nm).

The hydrophilicity of chip surface was another factor to consider in selecting LMWP from serum. The contact angles of MPS thin film surfaces were tested by captive bubble contact angle goniometry to characterize the hydrophilicity of the chips' surface. All mesoporous silica chips prepared with the four different tri-block copolymers were hydrophilic (contact angle <30°). FIG. 37a shows the image of a water droplet on the surface of a chip prepared with L121. This is a representative image to illustrate the high hydrophilicity of the MPS thin film surface. The chart in FIG. 37b details the contact angles of all MPS thin film chips that have been developed. The MPS thin films prepared from L121 exhibited the highest hydrophilicity due to the formation of their capillary condensation, increasing with the addition of the swelling agent. The MPS thin film surface prepared by P123 presented the lowest hydrophilicity among all the chips examined in this study resulting in the highest contact angle.

Figure 38C:
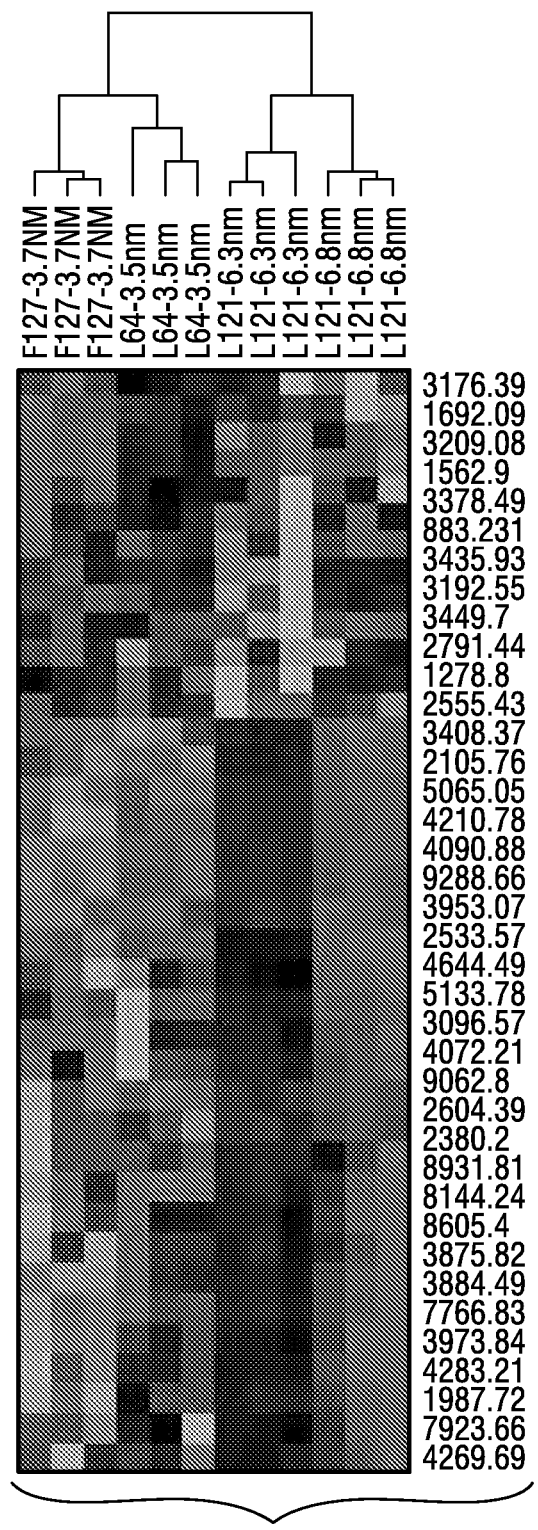
FIG. 38 shows the effect of pore size on LMWP recovery. a. Mass spectra of the proteins and peptides collected from samples fractionated using chips prepared with L64, F127, L121+50% PPG and L121+100% PPG (top to bottom), b. MS profiles of the samples fractionated using chips prepared with P123, c. The supervised hierarchical clustering analysis of peak intensities for samples fractionated using chips prepared with F127, L64, L121+50% PPG and L121+100% PPG. Red indicates peak intensities higher than the median value, green is for peak intensities lower than the median value, and black represents peak intensities equal to the median value. Each row represents an individual mass peak (MALDI MS peak) and each column represents a mesoporous thin film chip produced using a specific triblock copolymer.

The different LMW peptide and protein enrichment spectra are illustrated in FIG. 38a for the chips prepared with L64, F127, L121+50% PPG and L121+100% PPG. Though it possessed a similar pore size to the MPS thin film prepared from F127, the relatively higher hydrophobicity, smaller pore volume, and poor pore connectivity of the MPS thin film fabricated with polymer P123 presented limited harvesting capability, as shown in FIG. 38b. With the largest average pore size and the highest surface hydrophilicity, the mesoporous silica chip produced using L121+PPG captured peptides and proteins in a wider molecular mass range. The chips with small pore size prepared with F127 and L64 preferentially enriched the peptides in the lower mass range. To assess this size-dependant ability of the mesoporous silica chips to capture LMWP, a hierarchical clustering analysis of peptides extracted from four different mesoporous silica chips with various pore sizes was performed (FIG. 38c). The clustering algorithm clearly separates the samples into two major clusters representing specific proteomic patterns for smallest pore and largest pore chips. The high intensity of smaller LMWP was obtained with the chips prepared with L64 and F127 due to their preferred pore sizes, 3.20 nm and 3.71 nm respectively. However, the periodic pore structure and uniform small pore size provided by F127 chips demonstrate a more homogenous enrichment pattern. The mesoporous silica chips prepared by L121 with the pore sizes enlarged using the swelling agent (molar ratios of 50% to 100% PPG to template polymer) offer an increased selective capture of peptides and proteins with higher molecular weight. The larger pore size presented by the L121 with 100% PPG resulted in a more efficient recovery as illustrated by the higher intensity of the enrichment pattern observed on the hierarchical clustering.

Example 5.6

Improvement of Chemical Modification on MPS Thin Film and their Effect on Specific LMWP Recovery Another approach to improve the enrichment capacity of the MPS chips is to resolve the complexity of biological samples by separating peptides of interest according to their chemical properties. Herein described are MPS chips conjugated with chemical functional groups that provide cationic and anionic surfaces respectively. Post-grafting is a straightforward method to add organic groups onto the surface of the pores. MPS possesses many silanol (Si—OH) groups on the surface that can act as convenient anchoring points for organic functionalization. However, the high temperature during calcinations process may cause a portion of surface silanol groups to be extensively dehydrated, resulting in a substrate incompatible with potentially conjugating organosilane groups. Therefore, more research groups focus their attention on one-spot synthesis. This technology involves co-condensation of tetraalkoxysilanes and organotrialkoxysilanes in the presence of surfactants during synthesis, resulting in higher organic content and a more homogeneous organic distribution in the material. However, co-condensation in one-spot synthesis also caused several difficulties in addition to the control of the main parameters related to the EISA process. For instance, homogeneous solubility of the organic functionalities with silicate precursor in the medium limits the selection of surface modification. In the other hand, one-spot synthesis has a limited interest in our study due to the restricted selection of polymer templates, which must own a different melting point than organotrialkoxysilanes. Another influencing factor is the choice of co-solvents. The participation of organosilane into nanostructured films may also lead to the significant damage in the silica network.

Figure 40A:
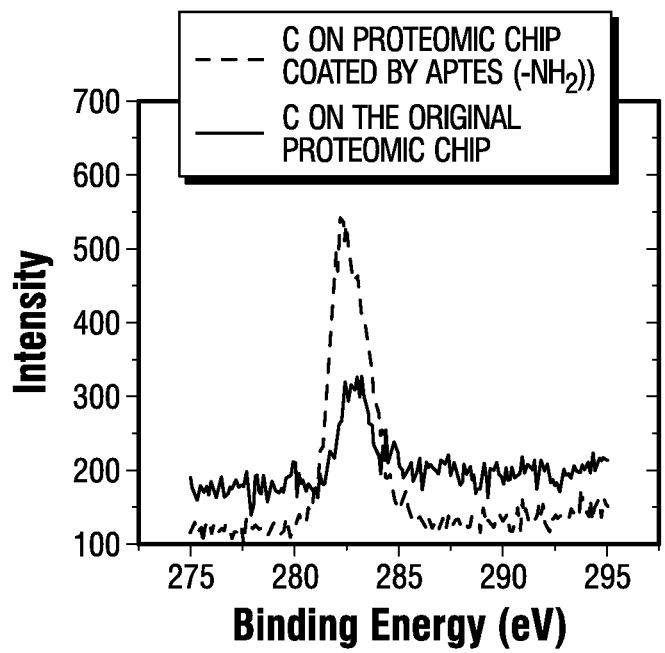
FIG. 40 shows the XPS spectra of mesoporous silica chips with APTES modification. Panel (a) present a comparison of C content in XPS on the mesoporous silica chips before and after APTES modification. Panel (b) presents a comparison of N content in XPS on the mesoporous silica chips modified with one-spot synthesis (black curve), modified with post-grafting without pre-treatment (red curve) and modified with post-grafting with oxygen plasma treatment (blue curve).
Figure 40B:
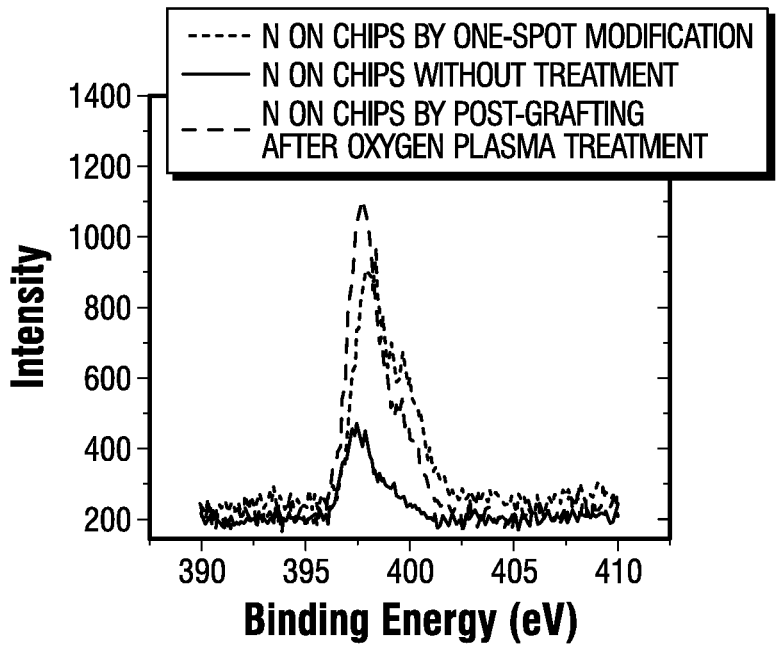

To break through the limitations aforementioned, the oxygen plasma ashing is used to treat the surface of mesoporous silica chip before the post-grafting. Plasma ashing is a technique for removing the photoresist in semiconductor manufacturing. Herein the oxygen plasma restored the defective points (Si—H) on MPS surface and generated a high-density Si—OH groups. FIG. 40a shows a comparison of XPS intensity of C content on the APTES modified chips before and after chemical modification. The significant increase of C 1s peak for the chips after modification, resulting from the alkyl chain on APTES, validates the efficacy of post-grafting on the chip surface treated with oxygen plasma. FIG. 40b exhibits the comparison for N 1s peak on the 3 mesoporous silica chips APTES-modified under different method (black curve: N 1s on the chips after one-spot modification, red curve: N 1s on the chips after post-grafting without any pre-treatment, blue curve: N 1s on the chips after post-grafting method with pre-treatment by oxygen plasma.) The difference for N1 s peak around the binding energy of 397 eV clearly implies the efficacy of oxygen plasma in grafting the functional groups on the pore surface. The chip that received pre-treatment of oxygen plasma is capable of conjugating four times the amino content than a chip without any surface treatment. Although the intensity for N1 s peaks are similar, the chip carried by post-grafting with oxygen plasma pre-treatment consisted of a sharper and more symmetric single peak at binding energies around 397 eV, which strongly points to a loading of APTES with high condensation on the pore surface.

Figure 41:
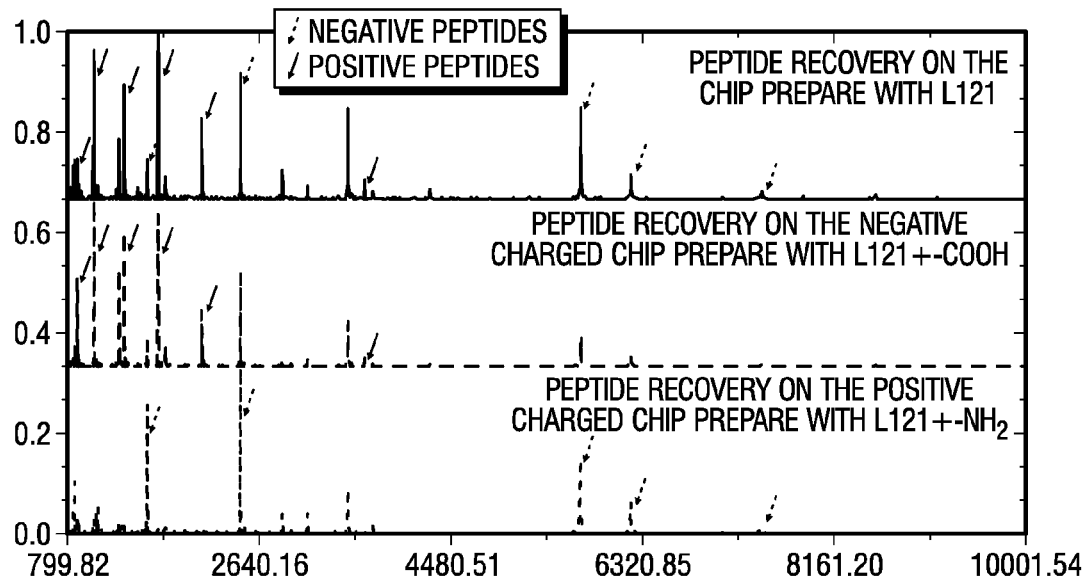
FIG. 41 shows the effects of chips functionalization on the LMW enrichment. MALDI-MS profiles of selectively captured peptides on the chemically modified chips. Positively and negatively charged mesoporous thin films specifically enrich negative and positive peptides respectively.
Figure 42A:
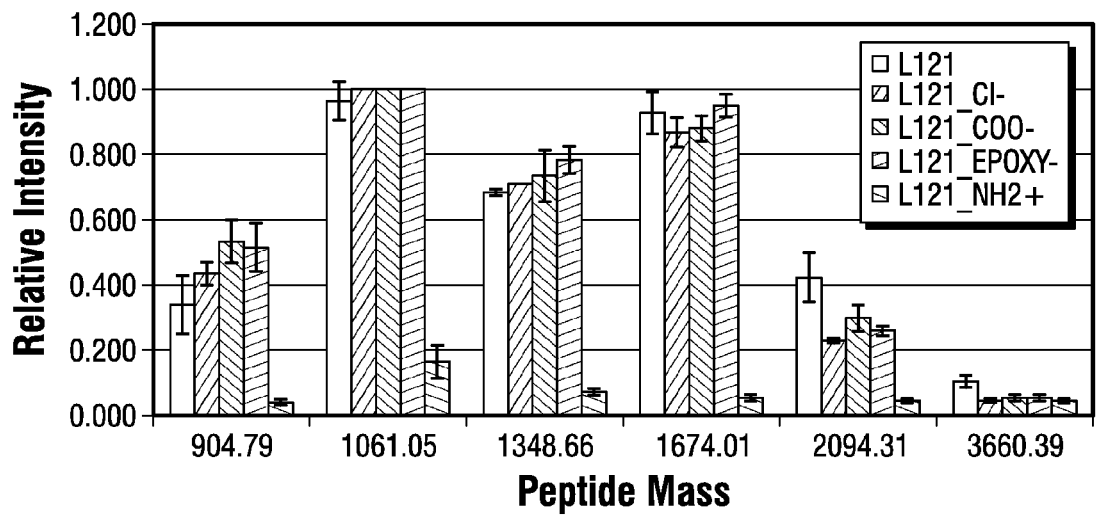
FIG. 42 shows the charge specific recovery for the chips with different surface functions. Bar graph of the MS intensity of detection of selectively captured peptides on the functionalized chips. According to their iso-electric point, the peptides are positively or negatively charged at pH 7.0. Panel (a) depicts positive peptides (1—des-Arg1-Bradykinin, 2—Bradykinin, 3—Substance P-amide, 4—Neurotensin, 5—ACTH(1-17), 6—ACTH(7-38)) are specifically enriched on the negatively charged surfaces. Panel (b) depicts negative peptides (7—Glu1-Fibrinopeptide B, 8—α-Endorphin, 9—ACTH(18-39), 10—Insulin, 11—EGF, 12—Insulin-like GFII) are specifically enriched on the positively charged surfaces.
Figure 42B:
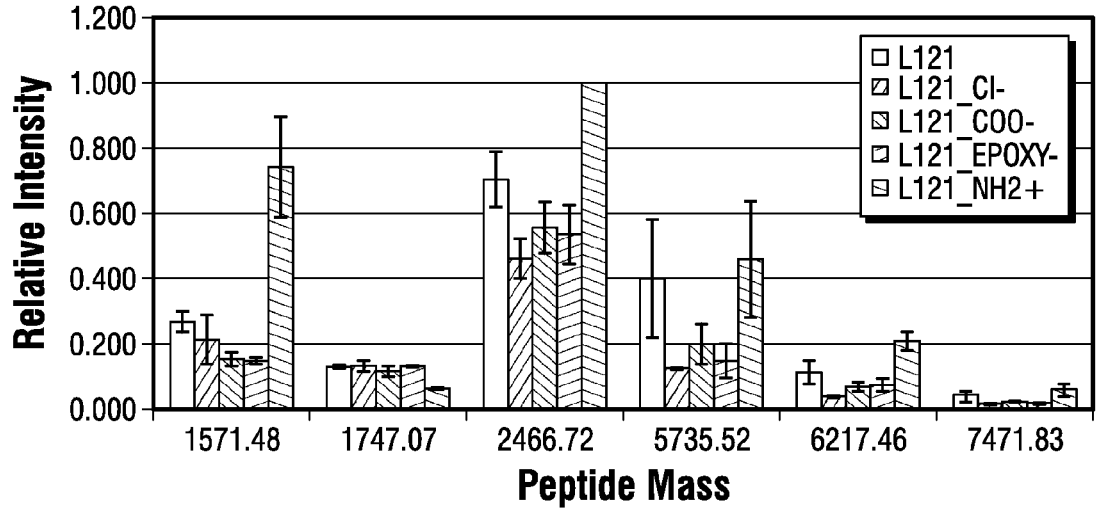

In order to qualitatively study the electrostatic effect on selective on-chip fractionation, 26 standard peptides and proteins were mixed with a wide range of molecular weights and isoelectric points. MS analysis of the proteomic standards solution fractionated on MPS chips prepared with L121 and conjugated with the chemical functional groups is presented in FIG. 41. The positively charged and negatively charged LMW peptides are captured on the anionic and the cationic chips respectively. HMW proteins remain excluded from the chips independently from their charge. For example, albumin has a net negative charge and remains excluded from the cationic chip. The quantitative comparison of multiple MPS chips in recovery the peptides with positive net charge is displayed in FIG. 42a. The chips with negative charge and the chip without any modification (with a minor negative charge originally) exhibit significantly higher enrichment for those peptides than the chip modified with APTES (—NH$_2$). Conversely, the positively charged MPS chips possess exceptional capability to recover those peptides with negative net charge, as demonstrated in FIG. 42b. These results and the identical molecular cut-off offer displayed by the chips demonstrate the dual properties of the functionalized MSC: 1—the size dependant depletion of HMW proteins by the porous surface; 2—the specific enrichment of differentially charged LMW peptides.

Evidence is mounting that the low molecular-weight region of the circulatory proteome is a rich source of diagnostic biomarkers for the early detection of disease. In this study, a series of mesoporous silica thin films with a variety of nanophase morphologies were fabricated and comprehensively explored their use in selective capturing and enriching LMW peptides and proteins from human serum.

Different MPS thin film periodic nanostructures, formed using high molecular weight triblock copolymers such as Pluronic F127 with similar pore size distributions, can be obtained by tuning the polymer concentration in the precursor solution. The 3D cubic and honeycomb hexagonal nanostructures, possessing more desirable nanopore interconnectivity and more accessible nanopore morphology, exhibit superior performance in selectively enriching LMW peptides than the 2D hexagonal structure, even though they share similar pore size distributions and the same molecular cut-off for serum fractionation. Precisely controlled variations in pore size can be achieved through the use of copolymers with differing hydrophobic block lengths. The effect of pore size on the LMW peptide and protein recovery efficacy was investigated using MPS thin films prepared from four Pluronic surfactants (F127, P123, L64, L121, and L121 plus swelling agent) with different volume ratios of the hydrophilic and hydrophobic components to form pore sizes of 3 nm, 4 nm, 6 nm, and 7 nm respectively. This range of pore sizes led to the recovery of a different repertoire of peptides and proteins from the same serum sample via size and shape exclusion. Moreover, the conjugation of organo-silane on MPS chips has been streamlined by introducing oxygen plasma ashing to pre-treat the chip surface. Further improvement in LMWP capture and identification can be achieved by studying 1) the impact of controlling the nanotexture of the chip surface on the enrichment of specific proteins, and 2) the effect of organic functional groups with various charges and polarities conjugated within the nanoporous matrix. The individual or integral use of different MPS thin films with carefully tailored characteristics provides a novel platform for the rapid and efficient analysis of the LMWP in human serum and may be implemented for the diagnosis of disease onset in many clinical settings.

Example 5.7

Fabrication of Mesoporous Silica Thin Films

As listed in FIG. 39, the molar ratios of starting materials are slightly different for various surfactants. A typical preparation of the coating sol was carried out as follows: the required amount of TEOS was dissolved in the mixture of ethanol, distilled water, and 2 M HCl and stirred for 1 hour at 75° C. to form a clear silicate sol. Separately, a portion of surfactant was dissolved in ethanol by stirring at room temperature. In the case of applying the swelling agent, the amount of PPG solution was put into the surfactant solution with vigorous stirring at room temperature. The coating solution was prepared by mixing the silicate sol into the triblock co-polymer solution followed by stirring of the resulting sol for 2 hrs at room temperature. The pH of the mixture solution remained around 1.5. The coating sol was deposited on a Si (1 0 0) wafer by spin-coating at the spin rate of 2500 rpm for 20 seconds. To increase the degree of polymerization of the silica framework in the films and to further improve their thermal stability, the as-deposited films were heated at 80° C. for 12 hrs. The films were calcinated at 425° C. to remove the organic surfactant. The temperature was raised at a heating rate of 1° C. per min, and the furnace was heated at 425° C. for 5 h. The films produced were transparent and crackless.

Example 5.8

Chemical Modification

Oxygen plasma ashing was performed in a Plasma Asher (March Plasma System) to pre-treat the MPS chip surface. The treatment was carried out with an O2 flow rate at 80 sccm and a power of 300 W for 10 minutes. Then silanate chips in a 3% organosilane in a Methanol:DI water (19:1) solution for 72 hours at room temperature in $N_2$ glovebox. Rinse sequentially with Methanol and DI water. Finally chips were cured at 110° C. for 15 min in a fan-operated oven.

Example 5.9

Characterization Techniques

Several characterization techniques to study the spin-coated mesoporous silica thin films were studied. By carrying out with a variable angle spectroscopic ellipsometer (J. A. Woollam Co. M-2000DI) and modeling with WVASE32 software, the thickness of thin films and their porosities were measured respectively in Cauchy model and Effective Medium Approximation (EMA) model. Ellipsometric optical quantities, the phase (A), and amplitude (V) were carried by requiring spectra for 65°, 70°, and 75° incidence angels using wavelengths from 300 to 1800 nm. In Cauchy model, the top layer's thickness, reflective index, and model fit parameters $A_n$, $B_{an}$ and $C_n$ were determined by fitting experimental data with the model and minimizing the mean square error (usually less than 10). Using the EMA model, the films' porosities were calculated by assuming a certain volume of void in the pure silica and setting the top layer's thickness obtained by the Cauchy model as the constant. X-ray diffraction (XRD) patterns were obtained on Philips X'Pert-MPD system with Cu Ka ray (45 kV, 40 mA). 0-20 scanning were recorded from all spin-coated films at Is/0.001° step over the angle range from 0.2° to 6°. Scanning transmission electron microscopy (STEM; FEI Technai; FEI Co.) was used in requiring micrographs of the plant view of mesoporous silica thin films at high tension of 200 kV. Contact angles of film surface were measured by goniometer with captive bubble contact angle measurement. $N_2$ adsorption/desorption analysis was applied in measuring surface area and pore size distribution. Quantachrome was used to record the $N_2$ adsorption/desorption isotherm at 77 K on the full range of relative $P/P_0$ pressures. Brunauer-Emmett-Teller (BET) surface areas were determined over a relative pressure range of 0.05 to 0.3. Nanopore size distributions were calculated from the desorption branch of the isotherms using Barrett-Joyner-Halenda (BJH) method. XPS spectra were recorded using a X-ray photoelectron spectrometer (Kratos Axis Ultra), utilizing a monochromated Al-$K_\alpha$ X-ray source (hv=1486.5 eV), hybrid optics (employing a magnetic and electrostatic lens simultaneously) and a multi-channel plate and delay line detector coupled to a hemispherical analyzer. The photoelectrons take off angle was 90°. All spectra were recorded using an aperture slot of 300×700 microns, and high resolution spectra were collected with a pass energy of 20 eV. The pressure in the analysis chamber was typically $2 \times 10^9$ Torr during data acquisition. Kratos XPS analysis software was used to determine the stoichiometry of samples from corrected peak areas and employing Kratos sensitivity factors for each element of interest.

Example 5.10

Serum Fractionation

For each experiment, a 10 µl of serum sample was pipetted onto the porous surface of the wafer square. The samples were incubated for 30 minutes at 25 degrees (room temperature) in a wet chamber (100% humidity) to prevent sample evaporation. The samples were washed 5 times with 15 µl of sterile, deionized water. Peptides and proteins were eluted from the pores using a 1:1 (v/v) mixture of acetonitrile and 0.1% trifluoroacetic acid (TFA) (Sigma).

Example 5.11

Mass Spectrometry

A matrix solution of 5 mg/ml α-cyano-4-hydroxycinnamic acid (CHCA, Sigma) in a 1:1 mixture of acetonitrile and 0.1% TFA (v/v) or a saturated solution of trans-3,5-dimethoxy-4-hydroxycinnamic acid (SA, Sigma) in 2:1 mixture of acetonitrile and water (v/v) containing 0.1% TFA was used for LMW and HMW analysis respectively. Each of the samples was mixed with the appropriate matrix in a ratio of 1:3, and spotted in duplicate onto the MALDI plate.

Mass spectra were acquired on a Voyager-DE™-STR MALDI-TOF (Applied Biosystems, Framingham, Mass.) mass spectrometer in liner positive-ion mode, using a 337 nm nitrogen laser. Samples were evaluated at two m/z ranges. For LMW peptides and proteins, m/z of 800-10,000 Da, using α-CHCA as matrix. Settings were optimized at an acceleration voltage 20 KV, grid voltage 19 KV, guide wire voltage 1 KV, delay time 180 ns, and low-mass gate 800. 300 laser shots crossed spot were averaged for each mass spectrum. For HMW proteins, parallel analysis using SA (Sinapinic Acid) as matrix and detection range of 3,000-100,000 Da was performed. The instrument was optimized at acceleration voltage 25 KV, grid voltage of 23.25 KV, guide wire voltage 6.25 KV, delay time of 500 ns and low mass gate 3,000.

The spectra were calibrated externally using the ProteoMass standards of peptides and proteins (Sigma) in each mass range. The raw spectra were processed with the Voyager Data Explorer software version 4.0 (Applied Biosystems).

Example 5.12

Statistical Analysis

The raw spectra were processed with the Voyager Data Explorer software version 4.0 (Applied Biosystems) and the data was exported to SpecAlign software for pretreatment. All spectra were aligned using the PAFFT correlation method and intensities were normalized to total ion current (TIC). The peak detection was performed with a height ratio of 2 with 0.3% of the mass window, and the baseline was corrected and the negative values were removed prior to analysis.

Hierarchical clustering was performed using Cluster software and visualized with MapleTree software. MALDI MS Data (M/z peak intensities) were log-transformed, normalized, and median centered. Pearson correlation was used to calculate the distance between the samples, and complete linkage clustering was performed. An independent Student t-test was used for comparison between groups (n=2 groups) for each detected MS peak prior to supervised hierarchical clustering analysis. A P-value of 0.02 or lower was considered significant to select differentially harvested peptides and proteins among the different mesoporous proteomic chips (Large pores vs. Small pores).

Example 6

Materials and Methods

Example 6.1

Fabrication of Mesoporous Silica (MPS) Chips

A typical preparation of a porous silica coating sol is as follows: 14 ml of tetraethyl orthosilicate (TEOS) (Sigma-Aldrich Co.) was dissolved in a mixture of 15 ml of ethanol, 6.5 ml of distilled water, and 0.5 ml of 6M HCl and stirred for 2 hours at 75° C. to form a clear sol. Separately, 1.8 g of Pluronic F127 (Gifted by BASF Co.) was dissolved in 10 ml of ethanol by stirring at room temperature followed by addition of 0.5 ml of DI water to form a homogeneous polymer solution. The coating solution was prepared by mixing 7.5 ml of the silicate sol into the F127 solution followed by stirring of this solution for 0.5 hours at room temperature. The pH of the mixture should remain around 1.5. The final sol was deposited on a silicon (1 0 0) wafer by spin-coating at a rate of 1500 rpm for 20 seconds. The thickness of the film was controlled by adjusting the concentration of polymer in the precursor solution, while the porosity mainly depends on the molar ratio of polymer and silicate in the starting material. To increase the degree of polymerization of the silica framework in the films and to further improve thermal stability, the as-deposited films were placed in an oven at 80° C. for 12 hours. For thermal calcination, the films were heated to 425° C. in air to remove the organic surfactant, at a heating rate of 1° C. per min, and the furnace was maintained at final temperature for 5 hours. Afterwards the oven was cooled to room temperature over 10 hours.

Example 6.2

Chemical Modification on Chip Surfaces

The mesoporous silica chip was pre-treated by oxygen plasma to establish a saturated hydroxyl-terminated surface. The treatment was performed in a Plasma Asher (March Plasma System) with an O2 flow rate at 80 sccm and a power of 300 W for 10 min. Surface phosphorylation was carried out via immersion of the chips in 80 ml of fresh 5 mM phosphorous oxychloride ($POCl_3$, Sigma-Aldrich Co.) and 10 mM triethylamine (Sigma-Aldrich Co.) in acetonitrile (Fisher Scientific Co.) for 6 hr at room temperature. The chips were spun dry via spin-coater at a spin speed of 2500 rpm following by immersion overnight in aqueous solution of 5 mM Zirconium (IV) oxychloride octahydrate/Titanium(IV) chloride (Sigma-Aldrich Co.) at room temperature (see Fig. S.1). $Ga^{3+}$ was immobilized on the pore surface by immersing MPS chip[35] in the aqueous solution of Gallium isopropoxide. The surfaces were rinsed with DI $H_2O$ and spun dry at a spin speed of 3000 rpm. Finally, the chips were heated at 120° C. for 30 minutes to remove residual water.

Example 6.3

Characterization Techniques

Several characterization techniques were utilized to study the spin-coated mesoporous silica thin films. The thicknesses of the thin films and their porosities were measured in Cauchy model and Effective Medium Approximation (EMA) model from spectra collected with a variable angle spectroscopic ellipsometer (J. A. Woollam Co. M-2000DI) and modeling with WVASE32 software. Ellipsometric optical quantities, the phase (A), and amplitude (y), were acquired from spectra at incident angles of 65°, 70°, and 75° using wavelengths from 300 to 1800 nm. In the Cauchy model, the top layer's thickness, reflective index, and model fit parameters $A_n$, $B_n$ and $C_n$ were determined by fitting experimental data with the model and minimizing the mean square error (usually less than 10). Using the EMA model, the film porosities were calculated by assuming a certain volume of void in the pure silica and setting the top layer's thickness obtained by the Cauchy model as the constant. X-ray diffraction (XRD) patterns were obtained on Philips X'Pert-MPD system with Cu Kα ray (45 kV, 40 mA). 0-20 scanning were recorded from all spin-coated films at 1 s/0.001° step over the angle range from 0.2° to 6°. Transmission electron microscopy (TEM; FEI Technai; FEI Co.) was used to acquire plan view micrographs of the mesoporous silica thin films at acceleration voltage of 200 kV. An EDX detector attached to the TEM was employed to analyze the chemical composition of the porous surface.

X-ray photonic spectroscopy (XPS) were recorded using a X-ray photoelectron spectrometer (Kratos Axis Ultra), with a monochromated $A_1$-$K_G$, X-ray source (hv=1486.5 eV), hybrid optics (employing a magnetic and electrostatic lens simultaneously) and a multi-channel plate and delay line detector coupled to a hemispherical analyzer. The photoelectrons take off angle was 90° normal to the surface.

Example 6.4

Phosphoproteins Sample Preparation

Phosvitin from egg yolk (Sigma-Aldrich Co) and α-casein from bovine milk (Sigma-Aldrich Co) were prepared per manufacture's instruction and 10 µg of each protein was trypsinized (Trypsin profile IGD kit, Sigma-Aldrich, Co) at 37° C. overnight. Then the trypsinized proteins solution was split into two halves and a 10 ul of phosphatase (Sigma-Aldrich Co) was added, followed by incubation at 30° C. for 30 minutes. 5 µg of phosvitin and α-casein were treated with same procedure as mentioned above as control. For serum enrichment, 10 µg phosphoproteins were add into human serum (The University of Texas, M. D Anderson Cancer Center).

Example 6.5

On-Chip Serum Fractionation

For each experiment, a 5 µl sample of serum or proteins was transferred by automatic pipette onto the porous surface of the chip. The samples were incubated for 30 minutes at 25° C. (room temperature) in a humidity chamber to prevent evaporation. The samples were washed 5 times with 10 µl of sterile, deionized water to remove surface bound material. Peptides and proteins were eluted from the pores using a 1:1 (v/v) mixture of acetonitrile and 0.1% trifluoroacetic acid (TFA) (Sigma).

Example 6.6

Matrix Assistant Laser Deposition/Ionization Mass Spectrometry (MALDI MS)

A matrix mixture (1:1) of 5 mg/ml α-cyano-4-hydroxycinnamic acid (CHCA, Sigma) in acetonitrile (Fluke) with 0.1% TFA (Sigma) was used for LMW peptide MALDI analysis. Each eluted sample was mixed in 2:3 ratio with matrix and spotted on MALDI plate in triplicate. All peptides and small proteins eluted from nanopores became positively charged during the interaction with TFA so positive mode is used to detect the signals of proteins. Mass spectra were acquired on an AB 4700 Proteomics TOF/TOF analyzer (Applied Biosystems, Framingham, Mass.) in both linear positive-ion and reflection modes, using 355 nm Nd-YAG laser. LMW proteins and peptides with m/z of 800-10000 Da and 700-5000 Da were selected for linear and reflection mode respectively. For linear mode, instrument setting was optimized at an acceleration voltage 20 kV, grid voltage of 18.8 kV, focus mass at 4000 Da, and low mass gate at 700. For reflector mode, instrument settings were optimized at an acceleration voltage 20 kV, grid voltage of 14 kV, focus mass at 2500 Da, and low mass gate at 700. Each spectrum was generated from 2000 (reflection) or 5000 (linear) laser shots per sample spot. External calibration was performed using 4700 Calibration standards mix of peptides and proteins (Applied Biosystems) in mass range of 800-10000 Da. Data Explorer software version 4.8 (Applied Biosystems) was used to process the raw spectra.

Example 6.7

Statistical Analysis

Processed data were imported into SpecAlign software for analysis. PAFFT correlation was used to align all spectra and their intensities normalized to total ion current (TIC). All spectra were smoothed and de-noised with factor of 4 and 0.5 respectively. Peaks were detected with a baseline of 0.5, mass window of 21 and height ratio 1.5, negative values were removed before analysis. Hierarchical clustering was performed using Cluster software and visualized with MapleTree. MALDI MS Data (M/z peak intensities) were log-transformed, normalized, and median centered. Pearson correlation was used to calculate the statistical distance between the samples, and complete linkage clustering was performed. An unsupervised clustering was performed for peaks automatically picked.

Results

Example 6.8

Synthesis and Characterization of Functionalized MPS Chips

By forming the layer structure of $MO_6$ octahedra, $Zr^{4+}$ and $Ti^{4+}$ are immobilized on mesopore surface with phosphate terminal groups, by which each metal cation shares oxygen atoms with monohydrogen phosphate groups, as shown below:

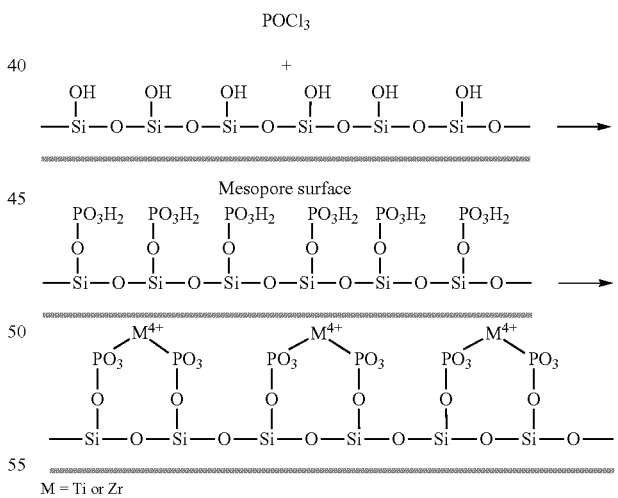

The strong coordination covalent bond between the metal ions and phosphate molecules provides a very stable and uniform interface of metal phosphate sites, whereby $Zr^{4+}$ or $Ti^{4+}$ maintains activity to react with the guest molecules with phosphate groups. $Ga^{3+}$ is immobilized on the pore surface by immersing oxygen plasma treated MPS chip in the aqueous solution of Gallium isopropoxide. Table 1 (below) list the ellipsometry, EDX and contact angle results of MPS chip and its functionalized chips. As shown, the respective thickness and surface hydrophilicity are relatively unchanged despite the application of varied surface modifications. Their porosities decrease however due to the conjugation of different metal ions and acid group. Because XPS only provides the elemental composition on the sample surface, the EDX results, by profiling at greater penetration depth, show the lower atomic percentages of all core elements immobilized on the chip surface versus that measured by XPS.

TABLE 1

The ellipsometry, EDX quantitative analysis and contact angle results of MPS chip and its different functionalized derivatives.

|  | Film thickness (nm) | Film porosity (%) | Atomic % of metal (EDX) | Atomic % of metal (XPS) | Surface contact angle (°) |
|---|---|---|---|---|---|
| MPS | 798.20 ± 8.22 | 55.27 ± 0.06 | 0 | 0 | 4.90 ± 0.24 |
| MPS/Ga$^{3+}$ | 801.97 ± 10.04 | 46.47 ± 0.05 | Ga: 0.45 ± 0.04 | Ga: 0.55 | 5.13 ± 0.39 |
| MPS/Ti$^{4+}$ | 813.01 ± 13.53 | 43.84 ± 0.06 | Ti: 0.55 ± 0.10 | Ti: 1.47 | 5.93 ± 0.27 |
| MPS/Zr$^{4+}$ | 810.11 ± 5.27 | 46.83 ± 0.03 | Zr: 1.01 ± 0.07 | Zr: 2.01 | 5.65 ± 0.54 |

(Each result is the average number from 15 spot tests.)

Figure 43A:
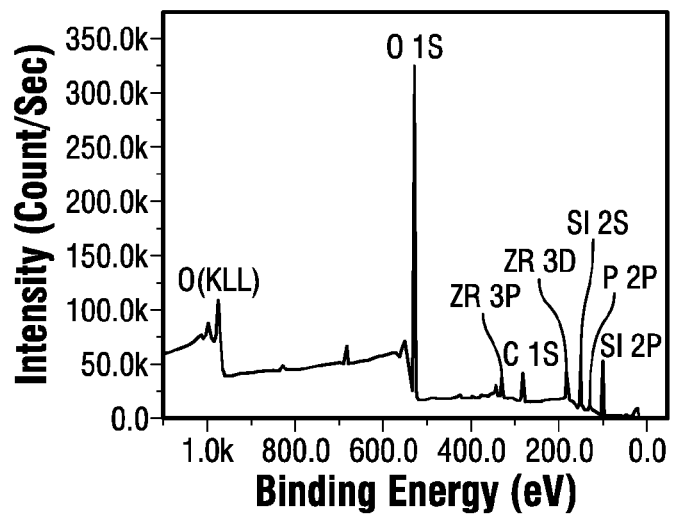
FIG. 43 is composed of a series of XPS survey scans providing the elemental composition of the functionalized pore surfaces (a, $Zr^{4+}$, c. $Ti^{4+}$ and e. $Ga^{3+}$), and XPS high resolution scans of the core elements providing information about the immobilized metal ions (b, $Zr^{4+}$, d. $Ti^{4+}$ and f. $Ga^{3+}$).
Figure 43B:
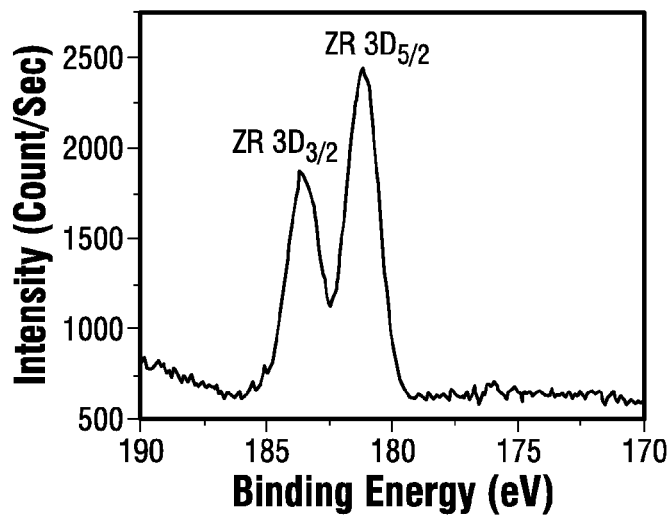
Figure 43C:
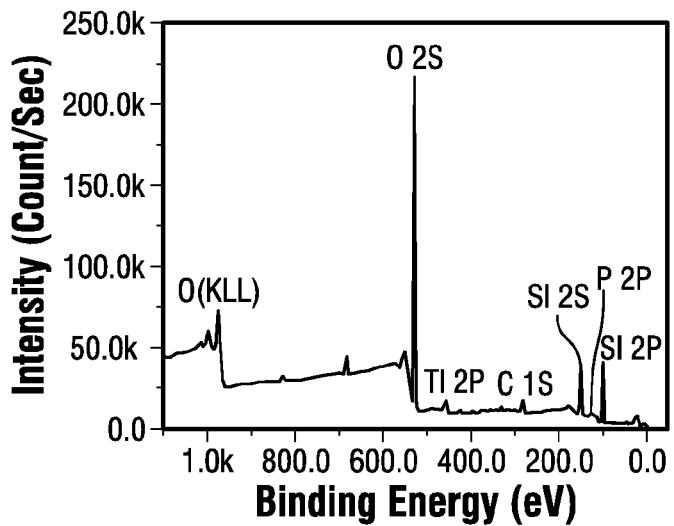
Figure 43D:
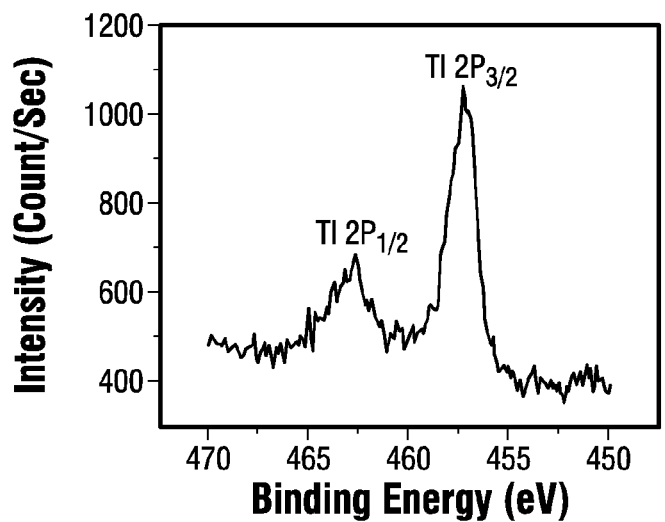
Figure 43E:
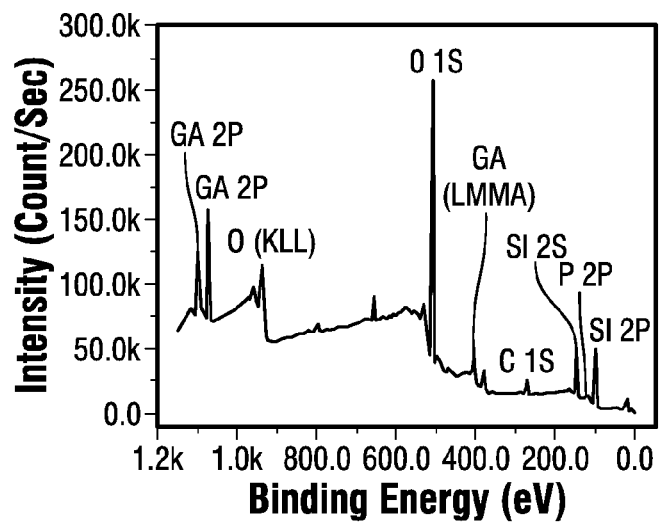
Figure 43F:
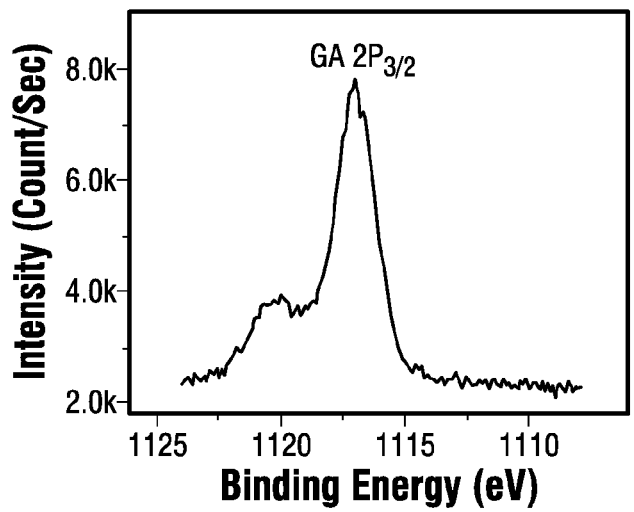

In order to confirm the successful functionalization of the mesoporous silica chips, elemental analysis was carried out using XPS for Zr$^{4+}$ (FIG. 43 and b), Ti$^{4+}$ (FIGS. 43c and d) and Ga$^{3+}$ (FIGS. 43e and f). As shown in FIGS. 43a, 43c and 43e, all of the collected survey spectra show strong peaks corresponding to O is (531 eV), Si 2p (99.3 eV), and Si 2s (151 eV); the strong peak at 981.5 eV is an oxygen Auger peak. Quantitative analysis of non-Auger peaks was conducted using high resolution spectra and reveals an oxygen-to-silicon ratio close to 2:1, indicative of the silica which constitutes our mesoporous silica thin film platform. Additionally, FIGS. 43a, 43c and 43e contain weak C is (284.5 eV) peaks, which can be attributed to the presence of surface contaminants, and a weak P 2p (131 eV) peak, which is due to the phosphate group used to link the hydroxy-terminated silica surface with desired metal ion species. FIG. 43b shows XPS core level spectrum of the immobilized zirconium ion by way of a phosphonate chelating linker, revealing a pair of sharp, symmetric Zr 3d peaks. The presence of these peaks, as well as secondary Zr 3p peaks at 330-340 eV, confirms the presence of zirconium on the surface of our modified MPS chips and validates our conjugation method. FIGS. 43d and 43f are high-resolution spectra of the characteristic peaks corresponding to titanium (Ti 2p$_{1/2}$: 464 eV, 2p$_{3/2}$: 457 eV) and gallium (Ga 2p: 1117 eV), respectively. Gallium's presence is also justified by an Auger peak at 420.5 eV which can be seen in FIG. 43e.

Figure 44:
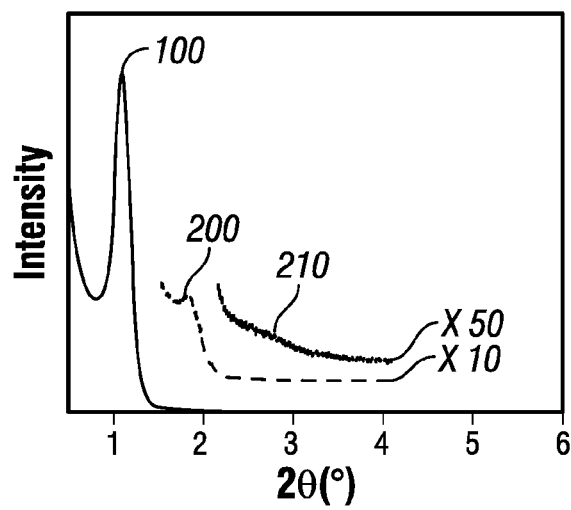
FIG. 44 depicts the small angle XRD patterns (0.2°-6°) for the MPS thin film of Example 6.

As shown in FIG. 44, calcined MPS chips templated with tri-block polymer F127 exhibited a well-resolved XRD pattern with a sharp diffraction peak and two low intensity diffraction peaks corresponding to d-spacing of 8.22, 4.10, and 3.10 nm, respectively. These three diffraction peaks can further be indexed as 100, 200, 210, which is a characteristic pattern for hexagonally arranged mesostructure. Functionalized MPS chips give a similar nanostructure with consistent cell parameters, indicating that the post-synthetic modification by metal ions preserve the hexagonal order of nanopores.

Figure 4A:
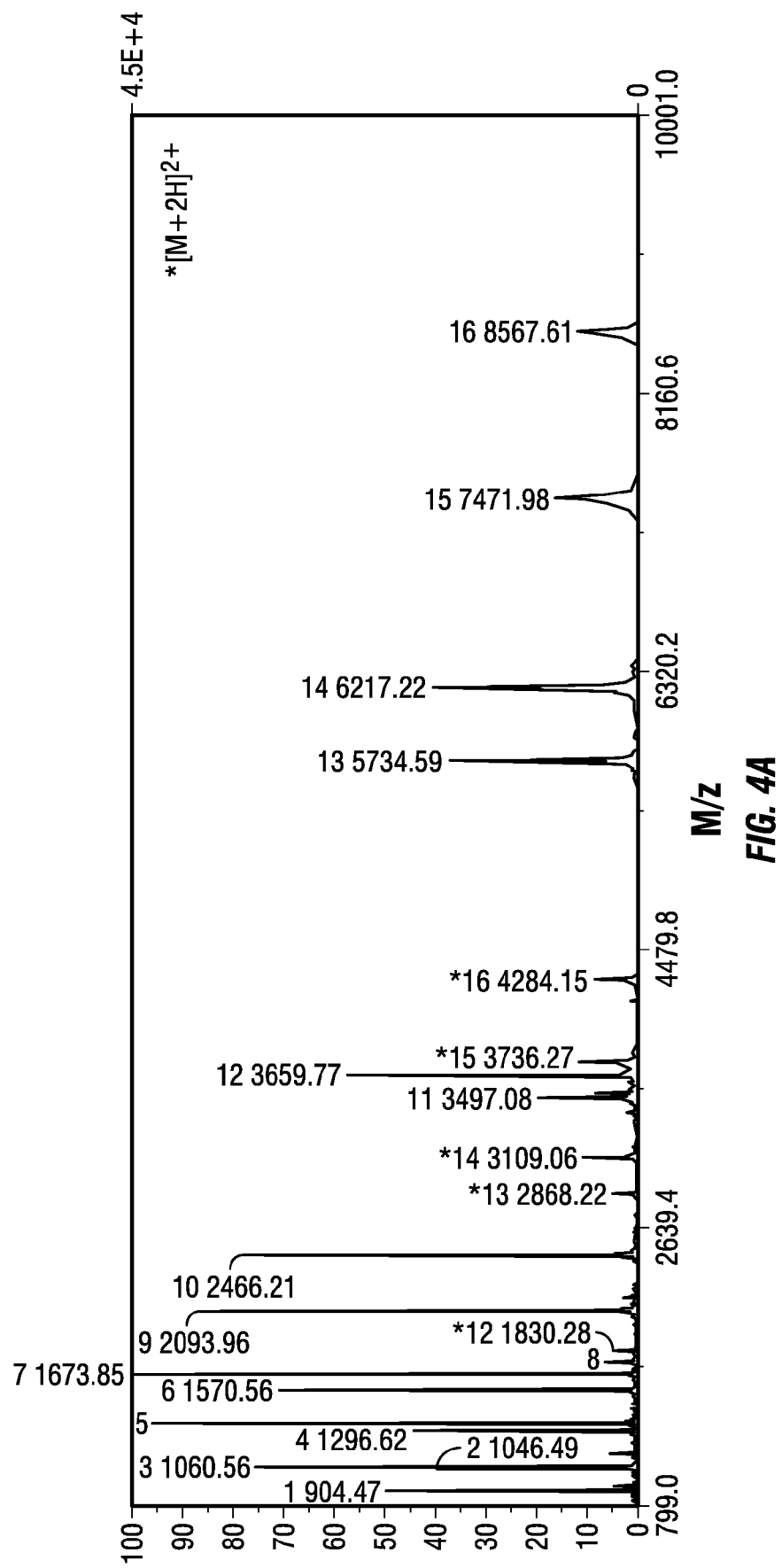
FIG. 4 shows the stability of peptide and protein standards. Panels a and b show representative MALDI profiles of the LMW and HMW standards, respectively. The stability of the set of peptide (16 weight markers from 900 to 8,500 Da) and protein (16 weight markers from 3,500 to 66,500 Da) in stock solution was investigated by MALDI-TOF MS after 1, 2, 3, 5, and 8 days storage at −20° C.
Figure 4B:
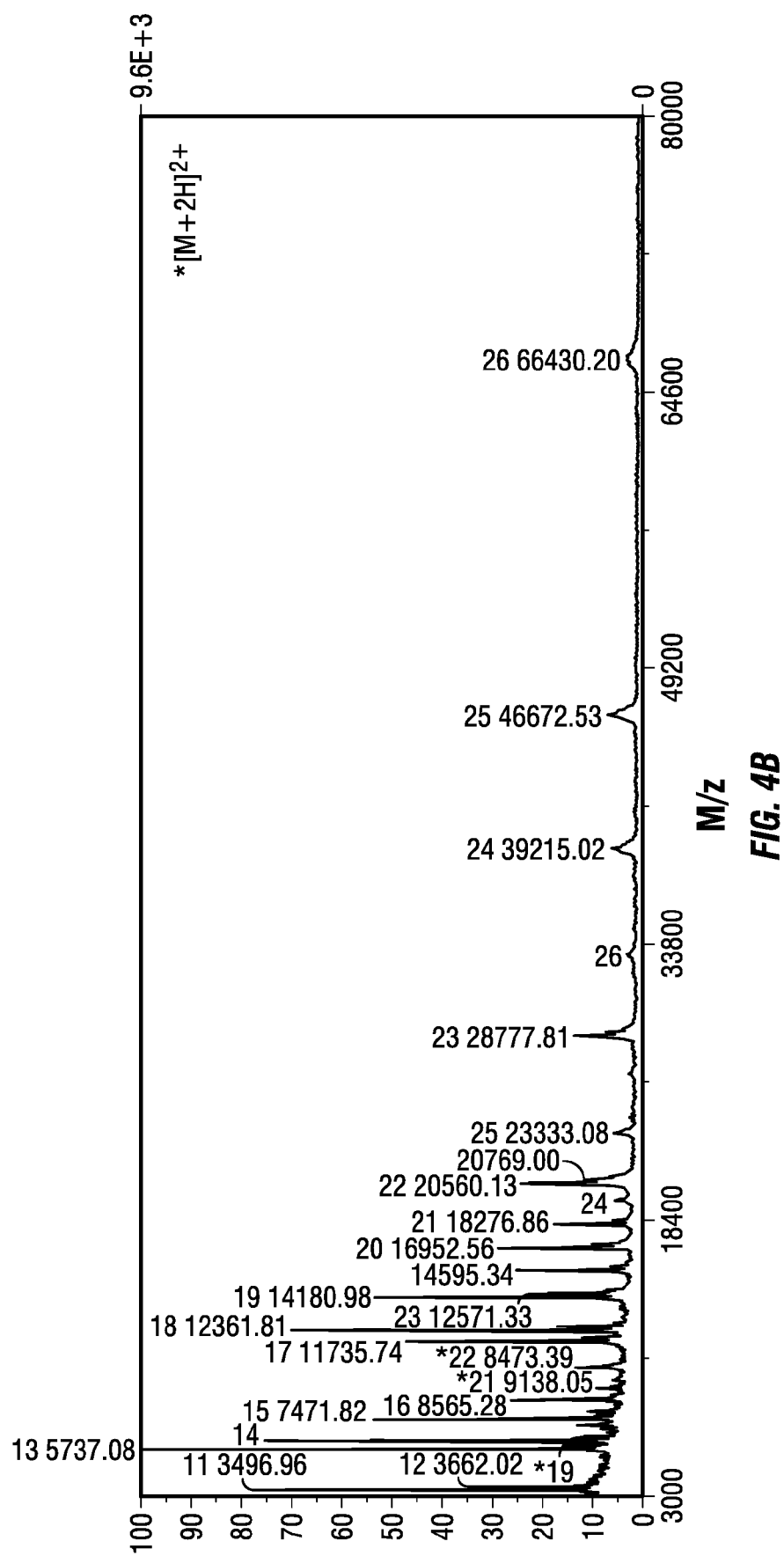
Figure 45A:
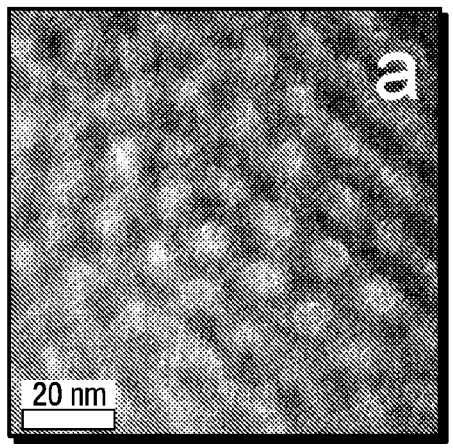
FIG. 45 depicts TEM images of the MPS thin film of Example 6, functionalized by (a) $Ga^{3+}$, (b) $Ti^{4+}$ and (c) $Zr^{4+}$ and their EDX spectra: (d) $Ga^{3+}$, (e) $Ti^{4+}$ and (f) $Zr^{4+}$.
Figure 45B:
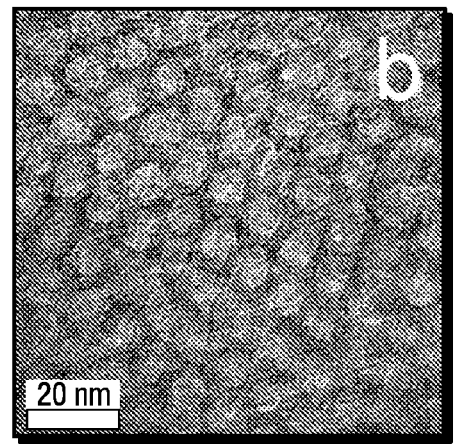
Figure 45C:
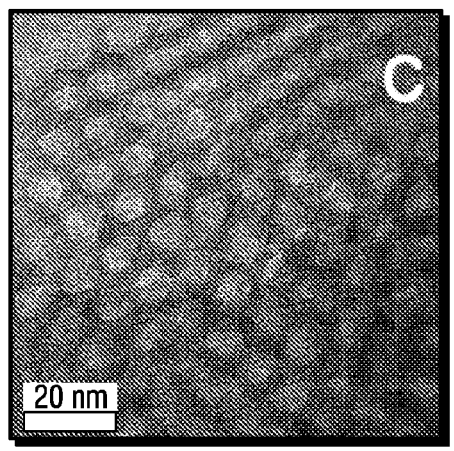
Figure 45D:
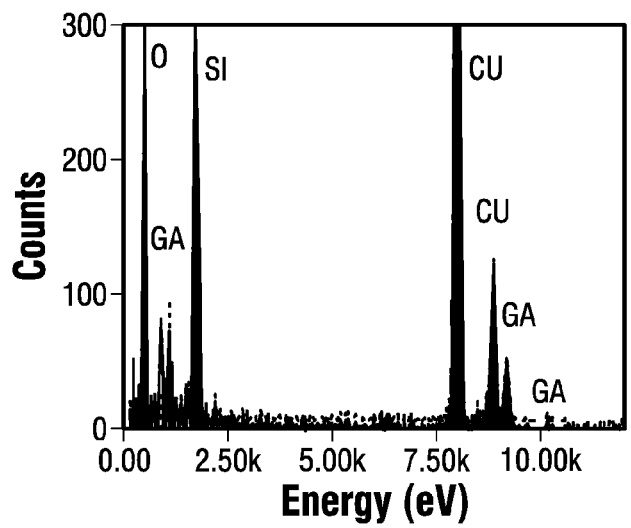
Figure 45E:
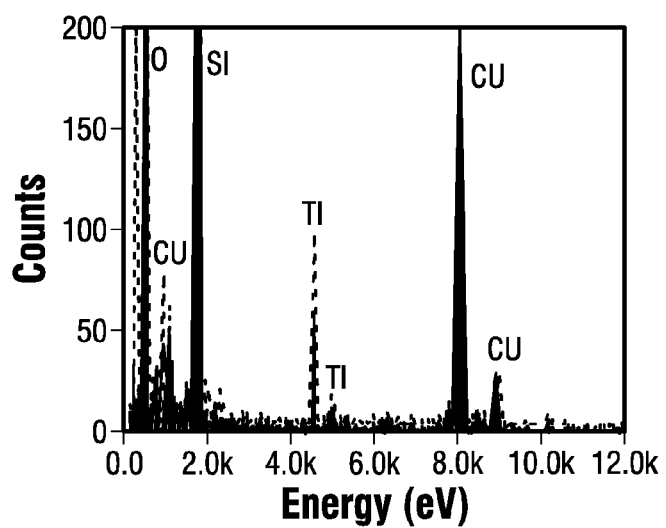
Figure 45F:
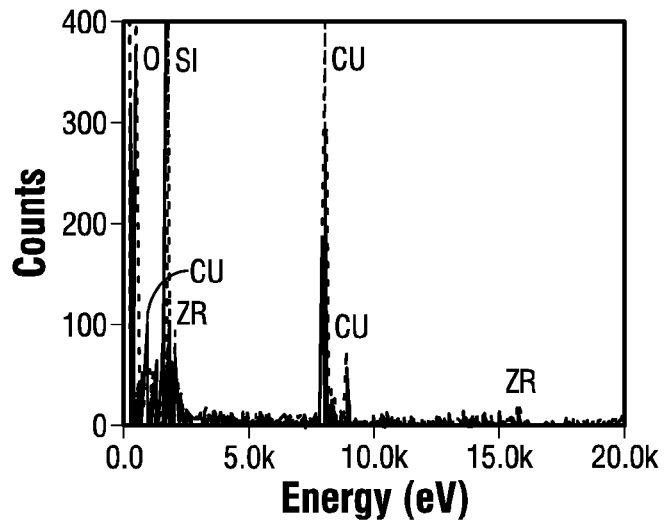

FIGS. 45a, 4b and 4c show TEM-obtained images of the metal ion immobilized MPS chips. The pores are shown to be uniformly distributed across the imaged area and, in accordance with the obtained XRD data, present themselves in a hexagonal nanoporous structure. FIGS. 45d, 45e and 45f show EDX spectra corresponding to each of the imaged TEM samples. EDX peaks for Si(1.740 KeV), O(0.523 KeV), C(0.282 KeV), and Cu(8.041 KeV) are seen on each of the displayed spectra, indicating the silica thin film and background of the TEM sample grid. More importantly, the EDX also detects peaks characteristic to each of the functionalizing metals: Ga (Kα: 9.243 KeV, Lα1: 1.096 KeV), Ti (Kα: 4.508 KeV), and Zr (Kα: 15.746 KeV, Lα1: 2.042 KeV) on FIGS. 45d, 45e, and 45f, respectively. Their atomic percentages have been listed in Table 1.

Example 6.9

Phosphoprotein Enrichment by Mesoporous Silica (MPS) Chips

Figure 46:
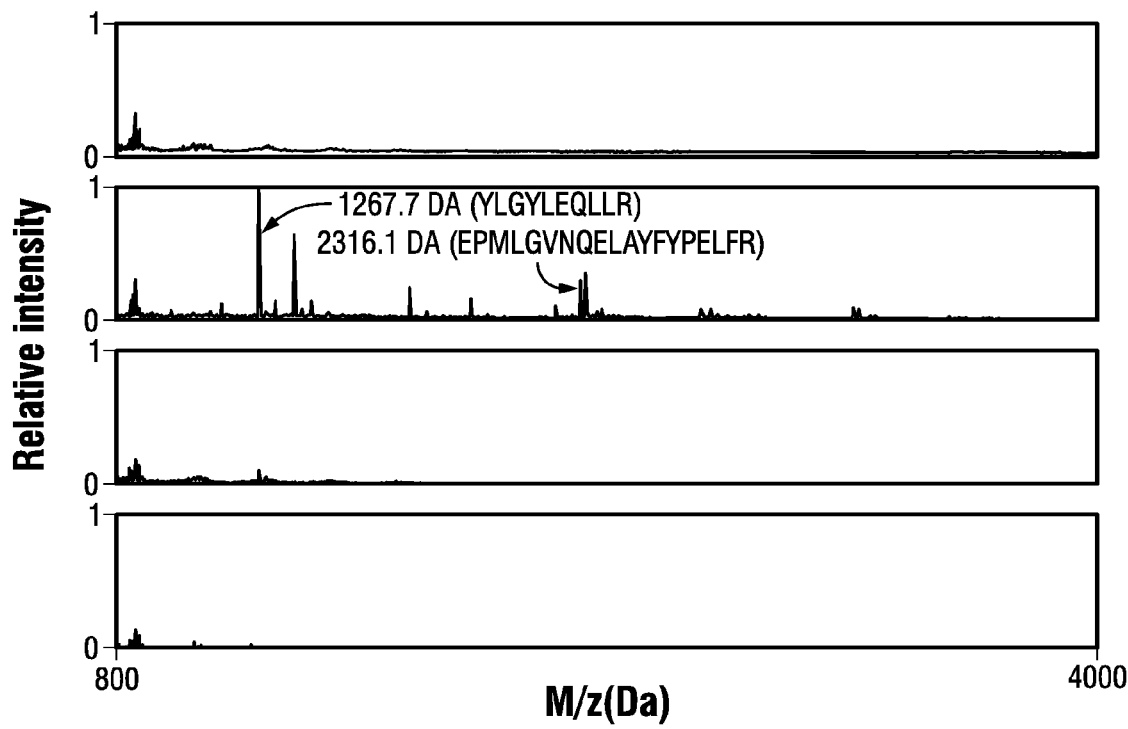
FIG. 46 depicts the MALDI TOF spectra of fractionated peptides processed by the $Zr^{4+}$ immobilized chip of Example 6, from (a) raw α-casein, (b) trypsinized α-casein, (c) trypsinized α-casein treated with phosphatase, and (d) raw α-casein treated with phosphatase.

The 23 kDa α-casein was used to test the effectiveness of the MPS chips. This protein was digested with trypsin which is a serine protease that specifically cleaves at the carboxylic side of lysine and arginine residues. The digestion mixture was then spotted on a Zr$^{4+}$ immobilized mesoporous silica thin film, and the captured peptides were recovered for MALDI TOF MS analysis. Peptides in the range of 800 to 4,000 Da were shown in FIG. 46. As anticipated, no peptide was detected from the undigested sample either in the low mass range (FIGS. 46a and 46d) or high mass range (10,000~30,000 Da). Several peaks were detected from the digested samples, indicating that peptides were effectively and selectively captured by the Zr$^{4+}$ immobilized chip (FIG. 46b). The amino acid sequences of the enriched phosphopeptides were labeled in the spectrum. In a parallel experiment, the trypsinized α-casein peptides were also treated with phosphatase to dephosphorylate. As shown in FIG. 46c, the same peaks in FIG. 46b could not be detected after phosphatase treatment, suggesting that the dephosphorylated peptides could not be captured by the same chip. This result further confirms the selectivity of the functionalized MPS chips in recovering phosphopeptides. Trypsin (24K Da) and phosphatase (69 K Da) were also treated with the same protocol and there were no peaks detected in the spectrum, indicating that both enzymes were removed during the washing steps. Tests with Ti$^{4+}$ and Ga$^{3+}$ immobilized chips showed similar results in the effectiveness of phosphopeptide enrichment (results not shown).

Figure 47:
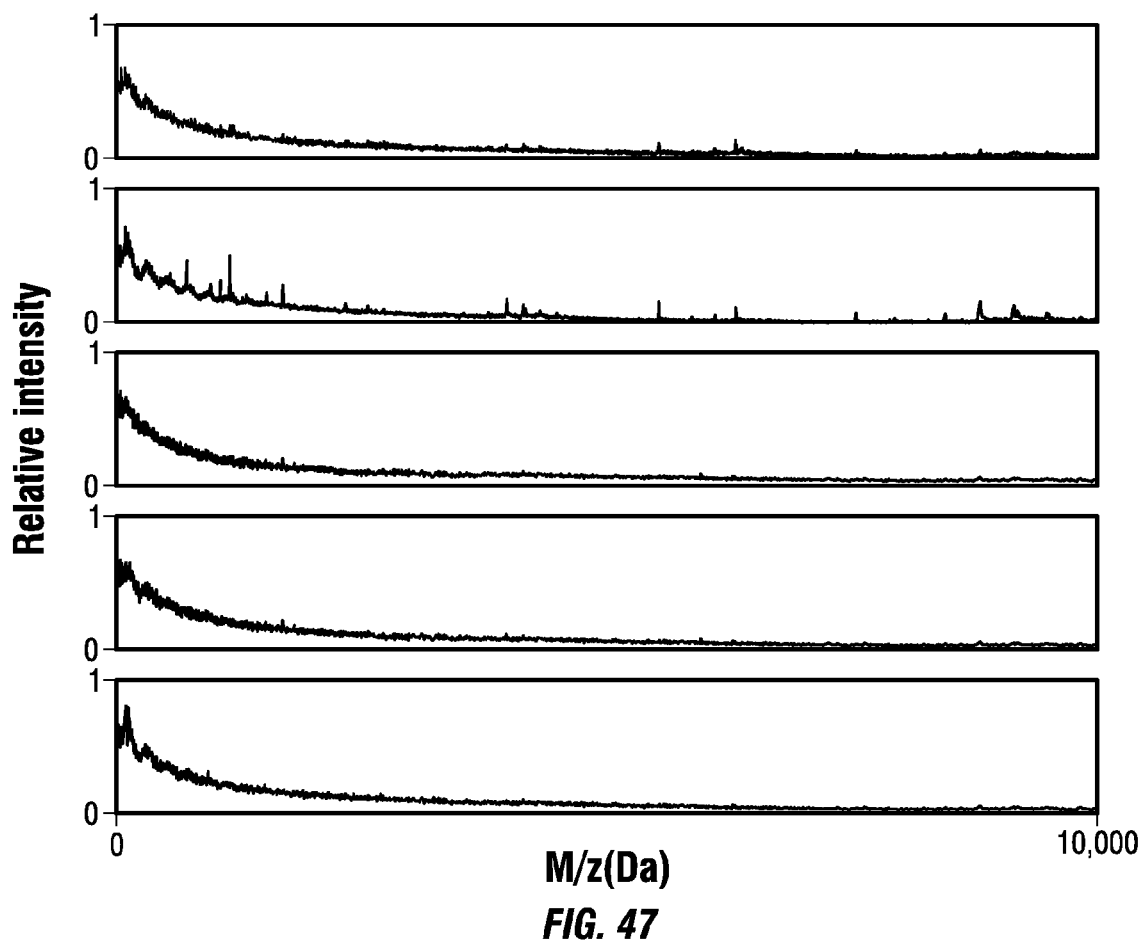
FIG. 47 depicts the MALDI TOF spectrum MS spectra of the fractionated samples on the $Zr^{4+}$ immobilized chip of Example 6, from (a) raw phosvitin in human serum, (b) trypsinized phosvitin in human serum, (c) trypsinized phosvitin, treated with phosphatase, in human serum (d) raw phosvitin treated with phosphatase in human serum and (e) human serum.

To test whether phosphopeptides could also be captured efficiently from complex samples such as human serum, trypsinized phosphoprotein phosvitin was mixed with serum, and processed the samples with the Zr$^{4+}$ immobilized MPS chips. No significant phosphopeptides were detected from human serum or serum mixed with undigested samples (FIGS. 47a, 47d and 47e). Peptides from trypsinized phosphoprotein phosvitin were captured and enriched by the Zr$^{4+}$ immobilized MPS chip (FIG. 47b), but no significant peaks were detected by MALDI TOF after dephosphorylation with phosphatase (FIG. 47c). The MS profiles demonstrated that the metal immobilized chips were able to specifically harvest the phosphopeptides from complex samples, and provided a platform to rapidly detect LMW peptides from serum or body fluids.

Example 6.10

Hierarchical Clustering Analysis

A hierarchical clustering analysis of peptides extracted from processed phosphopeptides as well as unprocessed peptides was performed. As shown in FIGS. 48A, B and C, their columns b representing trypsinized α-casein processed by the functionalized MPS chips exhibited a superior enrichment of LMW phosphopeptides, compared to α-casein without treatment or the dephosphorylated peptides. As show in FIG. 48D, the proteomic patterns fall into three clusters representing the ability of the MPS chips functionalized by $Zr^{4+}$, $Ga^{3+}$ and $Ti^{4+}$ to enrich phosphopeptides. The $Zr^{4+}$ and $Ti^{4+}$ chips show better enrichment at LMW mass range as compared to the $Ga^{3+}$ chip, which suggests that the unique coordination specificity of Zr or Ti ions immobilized on the MPS chips greatly improves the selectivity of phosphopeptide binding by preventing acidic peptide binding.

Example 6.11

Conclusion

Phosphopeptides are present in the serum proteome at concentrations that require accordingly low detection thresholds for early biomarker identification. Various metal ions ($Zr^{4+}$, $Ti^{4+}$ and $Ga^{3+}$) were immobilized on the mesoporous silica chips and their physico/chemical properties were fully characterized. The functionalized MPS chips, with high surface area, large pore volume and uniform pore size distribution, were used to efficiently isolate and enrich the low mass phosphopeptides from complex human serum samples. The use of functionalized MPS chips with engineered binding characteristics thus provides a novel platform for profiling the post-translational modification in the human proteome and potentially diagnosing early symptoms of cancer and other diseases.

What is claimed:

1. A method of analyzing a biological sample, the method comprising the steps of:
   a. providing the sample;
   b. providing a substrate comprising a silica-based mesoporous material, wherein:
      the pores of said mesoporous material have a pre-determined pore morphology;
      a surface of the substrate is functionalized with a phosphate moiety to which an inorganic metal ion is immobilized; and
      the inorganic metal ion is selected from the group consisting of gallium, titanium, and zirconium;
   c. exposing the mesoporous material to the sample such that a fraction of the sample is retained by the mesoporous material; and
   d. analyzing a fraction of the sample retained by the mesoporous material.

2. A method of detecting a marker of a physiological condition in a sample, the method comprising the steps of:
   a. providing a sample from a subject affected by the physiological condition;
   b. providing a substrate comprising a silica-based mesoporous material, wherein:
      the pores of said mesoporous material are substantially uniform and have a pre-determined pore morphology;
      a surface of the substrate is functionalized with a phosphate moiety to which an inorganic metal ion is immobilized; and
      the inorganic metal ion is selected from the group consisting of gallium, titanium, and zirconium;
   c. exposing the mesoporous material to the sample;
   d. analyzing a fraction of the sample retained by the mesoporous material; and
   e. comparing a result of the analyzing with a result of analyzing a control sample to detect the marker of the physiological condition.

3. A probe comprising a substrate that comprises a mesoporous material having a pre-determined morphology to separate a first component from a second component, wherein said probe is configured and arranged to be inserted into a mass spectrometer, wherein a surface of the substrate is functionalized with a phosphate moiety to which an inorganic metal ion is immobilized; and
   the inorganic metal ion is selected from the group consisting of gallium, titanium, and zirconium.

4. A mesoporous silica chip comprising multiple pores, wherein a surface of the mesoporous silica chip is functionalized with a phosphate moiety to which an inorganic metal ion is immobilized; and
   the inorganic metal ion is selected from the group consisting of gallium, titanium, and zirconium and wherein the pores on said chip are of different sizes and physiochemical properties.

5. The chip of claim 4, wherein said physiochemical properties are selected from the group consisting of surface area, pore size, the presence of functional groups, and the presence of an electrical charge.

6. The chip of claim 5, wherein said pores have a shape comprising cubic, hexagonal, honeycomb-like, tubular, circular, oblong, and combinations thereof.

* * * * *